United States Patent
Sahenk

(10) Patent No.: US 12,391,928 B2
(45) Date of Patent: Aug. 19, 2025

(54) RECOMBINANT ADENO-ASSOCIATED VIRUS PRODUCTS AND METHODS FOR TREATING LIMB GIRDLE MUSCULAR DYSTROPHY 2A

(71) Applicant: RESEARCH INSTITUTE AT NATIONWIDE CHILDREN'S HOSPITAL, Columbus, OH (US)

(72) Inventor: Zarife Sahenk, Columbus, OH (US)

(73) Assignee: Research Institute at Nationwide Children's Hospital, Columbus, OH (US)

( * ) Notice: Subject to any disclaimer, the term of this patent is extended or adjusted under 35 U.S.C. 154(b) by 1224 days.

(21) Appl. No.: 17/255,488

(22) PCT Filed: Jun. 28, 2019

(86) PCT No.: PCT/US2019/039893
§ 371 (c)(1),
(2) Date: Dec. 23, 2020

(87) PCT Pub. No.: WO2020/006458
PCT Pub. Date: Jan. 2, 2020

(65) Prior Publication Data
US 2021/0277362 A1    Sep. 9, 2021

Related U.S. Application Data

(60) Provisional application No. 62/865,081, filed on Jun. 21, 2019, provisional application No. 62/691,934, filed on Jun. 29, 2018.

(51) Int. Cl.
| | |
|---|---|
| *C12N 7/00* | (2006.01) |
| *A61K 48/00* | (2006.01) |
| *A61P 21/00* | (2006.01) |
| *C12N 9/64* | (2006.01) |
| *C12N 15/86* | (2006.01) |

(52) U.S. Cl.
CPC ............ *C12N 7/00* (2013.01); *A61K 48/0058* (2013.01); *A61P 21/00* (2018.01); *C12N 9/6472* (2013.01); *C12N 15/86* (2013.01); *C12N 2750/14131* (2013.01); *C12N 2750/14143* (2013.01)

(58) Field of Classification Search
CPC ... A61K 48/0058; A61P 21/00; C12N 9/6472; C12N 15/86; C12N 2750/14143
See application file for complete search history.

(56) References Cited

U.S. PATENT DOCUMENTS

| | | |
|---|---|---|
| 5,173,414 A | 12/1992 | Lebkowski et al. |
| 5,449,616 A | 9/1995 | Campbell et al. |
| 5,658,776 A | 8/1997 | Flotte et al. |
| 5,672,694 A | 9/1997 | Campbell et al. |
| 5,786,211 A | 7/1998 | Johnson |
| 5,871,982 A | 2/1999 | Wilson et al. |
| 6,204,059 B1 | 3/2001 | Samulski et al. |
| 6,258,595 B1 | 7/2001 | Gao et al. |
| 6,262,035 B1 | 7/2001 | Campbell et al. |
| 6,566,118 B1 | 5/2003 | Atkinson et al. |
| 6,632,800 B1 | 10/2003 | Russell et al. |
| 7,282,199 B2 | 10/2007 | Gao et al. |
| 7,759,314 B2 | 7/2010 | Fallon et al. |
| 7,790,449 B2 | 9/2010 | Gao et al. |
| 7,883,858 B2 | 2/2011 | Hood et al. |
| 9,061,059 B2 | 6/2015 | Chakraborty et al. |
| 9,434,928 B2 | 9/2016 | Mendell et al. |
| 10,105,453 B2 | 10/2018 | Mendell et al. |
| 11,358,993 B2 | 6/2022 | Rodino-Klapac et al. |
| 2001/0029040 A1 | 10/2001 | Toyo-Oka |
| 2003/0225260 A1 | 12/2003 | Snyder |
| 2006/0154250 A1 | 7/2006 | Morris et al. |
| 2007/0099251 A1 | 5/2007 | Zhang et al. |
| 2008/0249052 A1 | 10/2008 | Duan et al. |
| 2009/0054823 A1 | 2/2009 | Bridges et al. |
| 2009/0275107 A1 | 11/2009 | Lock et al. |
| 2009/0280103 A1 | 11/2009 | Flueck |
| 2010/0003218 A1 | 1/2010 | Duan et al. |
| 2010/0008979 A1 | 1/2010 | Tomatsu et al. |
| 2010/0026655 A1 | 2/2010 | Harley |
| 2010/0075866 A1 | 3/2010 | Hood et al. |
| 2010/0112694 A1 | 5/2010 | Marban |
| 2010/0120627 A1 | 5/2010 | Belouchi et al. |
| 2010/0247495 A1 | 9/2010 | Ichim et al. |
| 2010/0266551 A1 | 10/2010 | Richard et al. |
| 2011/0023139 A1 | 1/2011 | Weinstein et al. |
| 2011/0053221 A1 | 3/2011 | Chen et al. |

(Continued)

FOREIGN PATENT DOCUMENTS

| | | |
|---|---|---|
| CO | 20210000227 | 1/2021 |
| EP | 0 127 839 A2 | 12/1984 |

(Continued)

OTHER PUBLICATIONS

Wang, B., Li, J., Fu, F. et al. Construction and analysis of compact muscle-specific promoters for AAV vectors. Gene Ther 15, 1489-1499 (2008). (Year: 2008).*

(Continued)

*Primary Examiner* — Maria G Leavitt
*Assistant Examiner* — Michael Angelo Riga
(74) *Attorney, Agent, or Firm* — Foley & Lardner LLP

(57) ABSTRACT

Products and methods for treating limb girdle muscular dystrophy 2A are provided. In the methods, recombinant adeno-associated viruses deliver DNA encoding a protein with calpain 3 activity.

4 Claims, 11 Drawing Sheets
Specification includes a Sequence Listing.

(56) References Cited

U.S. PATENT DOCUMENTS

| | | |
|---|---|---|
| 2011/0070210 A1 | 3/2011 | Andrijauskas |
| 2011/0076744 A1 | 3/2011 | Wright et al. |
| 2011/0082192 A1 | 4/2011 | Milne et al. |
| 2011/0104120 A1 | 5/2011 | Xiao et al. |
| 2011/0266551 A1 | 11/2011 | Thompson et al. |
| 2011/0294193 A1 | 12/2011 | Amalfitano et al. |
| 2011/0301226 A1 | 12/2011 | Mendell et al. |
| 2012/0087862 A1 | 4/2012 | Hood et al. |
| 2013/0171172 A1 | 7/2013 | Richard et al. |
| 2014/0010861 A1 | 1/2014 | Bancel et al. |
| 2014/0147432 A1 | 5/2014 | Chakraborty et al. |
| 2014/0179770 A1 | 6/2014 | Zhang et al. |
| 2014/0234255 A1 | 8/2014 | Lai et al. |
| 2014/0249208 A1 | 9/2014 | Chakraborty et al. |
| 2014/0256802 A1 | 9/2014 | Boye et al. |
| 2014/0273231 A1 | 9/2014 | Zhang et al. |
| 2014/0323956 A1 | 10/2014 | Mendell et al. |
| 2015/0111955 A1 | 4/2015 | High et al. |
| 2015/0125429 A1 | 5/2015 | Perlingeiro et al. |
| 2015/0232883 A1 | 8/2015 | Dahlman et al. |
| 2015/0238627 A1 | 8/2015 | Leger et al. |
| 2016/0058890 A1* | 3/2016 | Buj Bello ............... C12N 9/16 435/320.1 |
| 2018/0256752 A1 | 9/2018 | Buj Bello et al. |
| 2019/0000998 A1 | 1/2019 | Mendell et al. |
| 2019/0202880 A1 | 7/2019 | Rodino-Klapac et al. |
| 2019/0343966 A1 | 11/2019 | Wang et al. |
| 2020/0339960 A1 | 10/2020 | Sahenk |
| 2021/0128749 A1 | 5/2021 | Rodino-Klapac et al. |
| 2021/0393801 A1 | 12/2021 | Rodino-Klapac et al. |
| 2023/0390417 A1* | 12/2023 | Sahenk ................. C12N 15/86 |

FOREIGN PATENT DOCUMENTS

| | | |
|---|---|---|
| EP | 0 155 476 A | 9/1985 |
| EP | 2 859 896 A1 | 4/2015 |
| JP | 2006-121961 A | 5/2006 |
| WO | WO-95/03392 A1 | 2/1995 |
| WO | 1995/13365 A1 | 5/1995 |
| WO | 1995/13392 A1 | 5/1995 |
| WO | 1996/17947 A1 | 6/1996 |
| WO | 1997/06243 A1 | 2/1997 |
| WO | 1997/08298 A1 | 3/1997 |
| WO | 1997/09441 A2 | 3/1997 |
| WO | 1997/21825 A1 | 6/1997 |
| WO | 1998/09657 A2 | 3/1998 |
| WO | WO-99/01176 A1 | 1/1999 |
| WO | 1999/11764 A2 | 3/1999 |
| WO | WO-99/43360 A1 | 9/1999 |
| WO | 2001/83692 A2 | 11/2001 |
| WO | 2002/53703 A2 | 7/2002 |
| WO | WO-03/074714 A1 | 9/2003 |
| WO | WO-2004/058146 A2 | 7/2004 |
| WO | WO-2007/057781 A2 | 5/2007 |
| WO | WO-2009/019505 A2 | 2/2009 |
| WO | WO-2009/054725 A2 | 4/2009 |
| WO | WO-2013/016352 A1 | 1/2013 |
| WO | WO-2013/078316 A1 | 5/2013 |
| WO | WO-2013/123503 A1 | 8/2013 |
| WO | WO-2013/151665 A2 | 10/2013 |
| WO | WO-2013/176772 A1 | 11/2013 |
| WO | WO-2014/037526 A1 | 3/2014 |
| WO | WO-2014/039916 A1 | 3/2014 |
| WO | WO-2014/093622 A2 | 6/2014 |
| WO | WO-2014/093712 A1 | 6/2014 |
| WO | WO-2014/204725 A1 | 12/2014 |
| WO | WO-2015/018503 A1 | 2/2015 |
| WO | WO-2015/021457 A2 | 2/2015 |
| WO | WO-2015/110449 A1 | 7/2015 |
| WO | WO-2015/158749 A2 | 10/2015 |
| WO | WO-2015/197232 A1 | 12/2015 |
| WO | WO-2016/115543 A2 | 7/2016 |
| WO | WO-2017087395 A1 * | 5/2017 ............. A61K 38/39 |
| WO | WO-2017/165859 A1 | 9/2017 |
| WO | 2017/180976 A1 | 10/2017 |
| WO | WO-2017/180857 A1 | 10/2017 |
| WO | WO-2017/181014 A1 | 10/2017 |
| WO | WO-2017/181015 A1 | 10/2017 |
| WO | WO-2017/221145 A1 | 12/2017 |
| WO | WO-2018/170408 A1 | 9/2018 |
| WO | WO-2019/012336 A1 | 1/2019 |
| WO | WO-2019/078916 A1 | 4/2019 |
| WO | WO-2019/118806 A1 | 6/2019 |
| WO | WO-2019/152474 A1 | 8/2019 |
| WO | WO-2019/195362 A1 | 10/2019 |
| WO | WO-2019/209777 A1 | 10/2019 |
| WO | WO-2019/245973 A1 | 12/2019 |
| WO | WO-2020/123645 A1 | 6/2020 |
| WO | WO-2020/176614 A1 | 9/2020 |
| WO | WO-2021/035120 A1 | 2/2021 |
| WO | WO-2021/257655 A1 | 12/2021 |

OTHER PUBLICATIONS

Roudaut, Carinne, et al. "Restriction of calpain3 expression to the skeletal muscle prevents cardiac toxicity and corrects pathology in a murine model of limb-girdle muscular dystrophy." Circulation 128.10 (2013): 1094-1104. (Year: 2013).*
NCBI BLAST Tool: Pairwise Similarity 1, Instant App ('488) SEQ ID No. 1 [1-3977]:: U.S. Pat. No. 9,981,049B2 SEQ ID No. 8 (CAPN3) (Year: 2024).*
NCBI BLAST Tool: Pairwise Similarity 2, Instant App ('488) SEQ ID No. 1 [1107-3572]:: U.S. Pat. No. 9,981,049B2 SEQ ID No. 8 (CAPN3) (Year: 2024).*
Wu, Zhijian, Aravind Asokan, and R. Jude Samulski. "Adeno-associated virus serotypes: vector toolkit for human gene therapy." Molecular therapy 14.3 (2006): 316-327. (Year: 2006).*
Yalvac et al., Impaired regeneration in calpain-3 null muscle is associated with perturbations in mTORC1 signaling and defective mitochondrial biogenesis, Skelet. Muscle, 7:27, (2017).
Bartoli et al., Safety and efficacy of AAV-mediated calpain 3 gene transfer in a mouse model of limb-girdle muscular dystrophy type 2A, Mol. Ther., 13(2):250-259 (2006).
Carinne et al: Restriction of Calpain3 Expression to the Skeletal Muscle Prevents Cardiac Toxicity and Corrects Pathology in a Murine Model of Limb-Girdle Muscular Dystrophy, Musc. Skel. Gen. Cell. Ther., 128(10):1094-1104 (2013).
Carter, Adeno-associated virus vectors, Current Opinions in Biotechnology, 3(5):533-539 (1992).
Clark et al., A stable cell line carrying adenovirus-inducible rep and cap genes allows for infectivity titration of adeno-associated virus vectors, Gene Therapy, 3(12):1124-1132 (1996).
Clark et al., Highly purified recombinant adeno-associated virus vectors are biologically active and free of detectable helper and wild-type viruses, Hum. Gene. Ther., 10(6):1031-1039 (1999).
Cserjesi et al., Myogenin induces the myocyte-specific enhancer binding factor MEF-2 independently of other muscle-specific gene products, Mol. Cell. Biol., 11(10):4854-4862 (1991).
De et al., High levels of persistent expression of alpha1-antitrypsin mediated by the nonhuman primate serotype rh.10 adeno-associated virus despite preexisting immunity to common human adeno-associated viruses, Mol. Ther., 13(1):67-76 (2006).
Flotte et al., Gene expression from adeno-associated virus vectors in airway epithelial cells, Am. J. Respir. Cell Mol. Biol., 7:349-356 (1992).
Gao et al., Clades of adeno-associated viruses are widely disseminated in human tissues, J. Virol., 78:6381-6388 (2004).
Hermonat et al., Use of adeno-associated virus as a mammalian DNA cloning vector: transduction of neomycin resistance into mammalian tissue culture cells, Proc. Natl. Acad. Sci. U.S.A., 81(20):6466-6470 (1984).
International Application No. PCT/US19/39893, International Preliminary Report on Patentability, mailed Jan. 7, 2021.
International Application No. PCT/US19/39893, International Search Report and Written Opinion, mailed Sep. 25, 2019.

(56) References Cited

OTHER PUBLICATIONS

Johnson et al., Muscle creatine kinase sequence elements regulating skeletal and cardiac muscle expression in transgenic mice, Mol. Cell. Biol., 9(8):3393-3399 (1989).
Klapac et al., Micro-dystrophin and follistatin co-delivery restores muscle function in aged DMD model, Hum. Mol. Genet., 22(24):4929-4937 (2013).
Kramerova et al., Null mutation of calpain 3 (p94) in mice causes abnormal sarcomere formation in vivo and in vitro, Hum. Mol. Genet., 13(13):1373-1388 (2004).
Laughlin et al., Cloning of infectious adeno-associated virus genomes in bacterial plasmids, Gene., 23(1):65-73 (1983).
Lebkowski et al., Adena-associated virus: a vector system for efficient introduction and integration of DNA into a variety of mammalian cell types, Mol. Cell. Biol., 7:3988-96 (1988).
Mader et al., A steroid-inducible promoter for the controlled overexpression of cloned genes in eukaryotic cells, Proc. Natl. Acad. Sci. U.S.A., 90(12):5603-5607 (1993).
Marsic et al., Vector design tour de force: integrating combinatorial and rational approaches to derive novel adeno-associated virus variants, Mol. Ther., 22(11):1900-1909 (2014).
McCarty, Self-complementary AAV vectors; advances and applications, Mol. Ther., 16(10):1648-1656 (2008).
McLaughlin et al., Adeno-associated virus general transduction vectors: analysis of proviral structures, J. Virol., 62(6):1963-73 (1988).
Mori et al., Two novel adeno-associated viruses from cynomolgus monkey: pseudotyping characterization of capsid protein, Virology, 330(2):375-383 (2004).
Muscat et al., Multiple 5'-flanking regions of the human alpha-skeletal actin gene synergistically modulate muscle-specific expression, Mol. Cell. Biol., 7(11):4089-4099 (1987).
Muzyczka, Use of adeno-associated virus as a general transduction vector for mammalian cells, current topics in microbiology and immunology, 158:97-129 (1992).
Paul et al., Increased viral titer through concentration of viral harvests from retroviral packaging lines, Human Gene Therapy, 4(5):609-615 (1993).
Perrin et al., An experimental rabies vaccine produced with a new BHK-21 suspension cell culture process: use of serum-free medium and perfusion-reactor system, Vaccine, 13(13):1244-1250 (1995).
Rabinowitz et al., Cross-packaging of a single adeno-associated virus (AAV) type 2 vector genome into multiple AAV serotypes enables transduction with broad specificity, J. Virol., 76(2):791-801 (2002).
Richard et al., Mutations in the Proteolytic Enzyme Calpain 3 Cause Limb-Girdle Muscular Dystrophy Type 2A, Cell., 81(1):27-40 (1995).
Rodino-Klapac et al., A translational approach for limb vascular delivery of the micro-dystrophin gene without high volume or high pressure for treatment of Duchenne muscular dystrophy, J. Transl. Med., 5:45-55 (2007).
Sambrook et al., Molecular cloning: A laboratory manual, 2nd Ed., Cold spring harbor laboratory, (1989).
Samulski et al., Cloning of adeno-associated virus into pBR322: rescue of intact virus from the recombinant plasmid in human cells, Proc. Natl. Acad. Sci. U.S.A., 79(6):2077-2081 (1982).
Samulski et al., Helper-free stocks of recombinant adeno-associated viruses: normal integration does not require viral gene expression, J. Virol., 63(9):3822-3828 (1989).
Schenpp et al., Highly purified recombinant adeno-associated virus vectors. Preparation and quantitation, Methods Mol. Med., 69:427-443 (2002).
Semenza et al., Hypoxia-inducible nuclear factors bind to an enhancer element located 3' to the human erythropoietin gene, Proc. Natl. Acad. Sci. U.S.A., 88(13):5680-5684 (1991).
Senapathy et al., Molecular cloning of adeno-associated virus variant genomes and generation of infectious virus by recombination in mammalian cells, J. Biol. Chem., 259:4661-4666 (1984).

Srivastava et al., Nucleotide sequence and organization of the adeno-associated virus 2 genome, J. Virol., 45:555-564 (1983).
Tratschin et al., A human parvovirus, adeno-associated virus, as a eucaryotic vector: transient expression and encapsidation of the procaryotic gene for chloramphenicol acetyltransferase, Mol. Cell. Biol., 4(10):2072-2081 (1984).
Tratschin et al., Adeno-associated virus vector for high-frequency integration, expression, and rescue of genes in mammalian cells, Mol. Cell. Biol., 5(11):3251-3260 (1985).
Wang et al., Construction and analysis of compact muscle-specific promoters for AAV vectors, Gene. Therapy, 15(22):1489-1499 (2008).
Wang et al., The potential of adeno-associated viral vectors for gene delivery to muscle tissue, Exp. Opin. on Drug. Del., 11(3):345-364 (2014).
Wein et al., Translation from a DMD exon 5 IRES results in a functional dystrophin isoform that attenuates dystrophinopathy in humans and mice, Nature Medicine, 20(9):992-1000 (2014).
Weintraub et al., The myoD gene family: nodal point during specification of the muscle cell lineage, Science, 251:761-766 (1991).
Roudaut et al., Restriction of Calpain3 Expression to the Skeletal Muscle Prevents Cardiac Toxicity and Corrects Pathology in a Murine Model of Limb-Girdle Muscular Dystrophy, Circulation, 128(10): 1094-1104, (Sep. 2013).
Rodino-Klapac, et al., Micro-dystrophin and follistatin co-delivery restores muscle function in aged DMD model, Hum. Mol. Genet., 22(24): 4929-4937, (Dec. 2013).
Yalvac et al., Impaired regeneration in calpain-3 null muscle is associated with perturbations in mTORC1 signaling and defective mitochondrial biogenesis, Skelet. Muscle, 7:27, 18 pages (2017).
Abadi et al., Supplementation with alpha-lipoic acid, CoQ10, and vitamin E augments running performance and mitochondrial function in female mice, PLoS One, 8(4):e60722 (2013).
ABSS (Sequence Alignment; WO2020006458, SEQ ID #1; accessed Mar. 12, 2024) (Year: 2024).
ABSS2 (Sequence Alignment; U.S. Appl. No. 17/255,488, SEQ ID #1; accessed Mar. 12, 2024) (Year: 2024).
Allamand et al., Early adenovirus-mediated gene transfer effectively prevents muscular dystrophy in alpha-sarcoglycan-deficient mice, Gene Ther., 7(16):1385-91 (2000).
Anderson et al., "Nucleic acid hybridisation: A practical approach," Ch. 4, IRL Press Limited, Oxford, England (1 page) 1985.
Anderson et al., "Quantitative Filter Hybridisation—Chapter 4", Nucleic acid hyridisation a practical approach, 1985, pp. 73-111.
Angelini et al., The clinical spectrum of sarcoglycanopathies, Neurology, 52:176-179 (1999).
Araishi et al., Loss of the sarcoglycan complex and sarcospan leads to muscular dystrophy in beta-sarcoglycan-deficient mice, Hum. Mal. Genet. 8: 1589-1598 (1999).
Arnold et al., Electrophysiological Biomarkers in Spinal Muscular Atrophy: Preclinical Proof of Concept, Ann. Clin. Transl. Neural., 1 (1 ):34-44 (Jan. 2014).
Asokan et al., The AAV Vector Toolkit: Poised at the Clinical Crossroads; Molecular Therapy, 20(4):699-708 (2012).
Au et al., "Gene therapy advances: a meta-analysis of AAV Usage in Clinical Settings," Frontiers in Medicine, Feb. 9, 2022, vol. 8 (pp. 1-14).
Bang et al., The complete gene sequence of titin, expression of an unusual approximately 700- kDa titin isoform, and its interaction with obscurin identify a novel Z-line to I-band linking system, Gire. Res. 89:1065-72 (2001).
Barresi et al., Disruption of heart sarcoglycan complex and severe cardiomyopathy caused by beta sarcoglycan mutations, J. Med. Genet. 37: 102-107 (2000).
Bearzi et al., Human cardiac stem cells, Proc. Natl. Acad. Sci. USA. 104:14068-73 (2007).
Beastrom et al., mdx(5cv) mice manifest more severe muscle dysfunction and diaphragm force deficits than do mdx Mice, Am. J. Pathol., 179(5):2464-74 (2011).
Behlke, Chemical modification of siRNAs for in vivo use, Oligonucleotides. 18:305-319 (2008).

(56) References Cited

OTHER PUBLICATIONS

Belfort et al., Homing endonucleases: from genetic anomalies to programmable genomic clippers Methods Mal. Biol. 1123:1-26 (2014).
Boch et al., Breaking the code of DNA binding specificity of TAL-type III effectors, Science. 326:1509-12 (2009).
Boissel et al., "megaTALs a rare-cleaving nuclease architecture for therapeutic genome engineering," Nucleic Acids Research, 2014, vol. 42, No. 4 (pp. 2591-2601).
Boissel et al., Assembly and characterization of megaTALs for hyperspecific genome engineering applications, Methods Mal. Biol. 1239:171-96 (2015).
Bolduc et al., "Recessive Mutations in the Putative Calcium-Activated Chloride Channel Anoctamin 5 Cause Proximal LGMD2L and Distal MMD3 Muscular Dystrophies", The American Journal of Human Genetics, 86, Feb. 12, 2010, (pp. 213-221).
Bonnemann et al., Betasarcoglycan (A3b) mutations cause autosomal recessive muscular dystrophy with loss of the sarcoglycan complex, Nat. Genet., 11(3):266-273 (1995).
Bonnemann et al., Genomic screening for beta-sarcoglycan gene mutations: missense mutations may cause severe limb-girdle muscular dystrophy type 2E (LGMD 2E), Hum. Mol. Genet. 5:1953-1961 (1996).
Bouquet et al., Miyoshi-like distal myopathy with mutations in anoctamin 5 gene, Rev. Neural. (Paris), 168(2):135-41 (Feb. 2012).
Bramsen et al., Development of therapeutic-grade small interfering RNAs by chemical engineerinq, Front. Genet. 20:154 (2012).
Ceccadi et al., Homologous recombination-deficient tumors are hyper-dependent on POLQ mediated repair, Nature. 518:258-262 (2015).
Cekaite et al., Gene expression analysis in blood cells in response to unmodified and 2'-modified siRNAs reveals TLR-dependent and independent effects, J. Mal. Biol. 365:90-108 (2007).
Centner et al., Identification of muscle specific ring finger proteins as potential regulators of the titin kinase domain, J. Mal. Biol. 306:717-26 (2001).
Cermak et al ., "Efficient design and assembly of custom TALEN and other TAL effector-based constructs for DNA targeting," Nucleic Acids Research, 2011, (pp. 1-11).
Cermak et al., Efficient design and assembly of custom TALENs using the Golden Gate platform, Methods Mal. Biol. 1239:133-59 (2015).
Ceyhan-Birsoy et al., Recessive truncating titin gene, TTN, mutations presenting as centronucleal myopathy, Neuroloov. 81:1205-14 (2013).
Chandrasekharan et al., Genetic defects in muscular dystrophy, Methods Enzymol. 479:291-322 (2010).
Chao et al., "Several log increase in therapeutic transgene delivery by distinct adeno-associated viral serotype vectors," Molecular therapy: the journal of the American Society of Gene Therapy, 2000, vol. 2, Issue 6, pp. 619-623.
Chao et al., "Sustained and complete phenotype correction of hemophilia B mice following intramuscular injection of AAV1 serotype vectors," Molecular therapy: the journal of the American Society of Gene Therapy, 2001, vol. 4, Issue 3, pp. 217-222.
Chauveau et al., A rising titan: TTN review and mutation update, Human Mutation. 35:1046-59 (2014).
Chernolovskaya et al., Chemical modification of siRNA, Curr. Opin. Mal. Ther. 12:158-67 (2010).
Chicoine et al., "Plasmapheresis eliminates the negative impact of AAV antibodies on microdystrophin gene expression following vascular delivery," Molecular therapy: the journal of the American Society of Gene Therapy, 2014, vol. 22, Issue 2, pp. 338-347.
Chicoine et al., "Vascular delivery of rAAVrh74.MCK.GALGT2 to the gastrocnemius muscle of the rhesus macaque stimulates the expression of dystrophin and laminin a2 surrogates", Mol. Ther., 22:713-24 (2014).
Chiorini et al., Cloning and characterization of adeno-associated virus type 5, J. Viral., 73(2):1309-19 (Feb. 1999).

Chiorini et al., Cloning of adeno-associated virus type 4 (AAV4) and generation of recombinant AAV4 particles, J. Viral., 71 (9):6823-33 (Sep. 1997).
Cho et al., DNA repair: Familiar ends with alternative endings, Nature. 518:174-6 (2015).
Chu et al., "SV40 DNA transfection of cells in suspension: analysis of the efficiency of transcription and translation of T-antigen", Gene, 13, (1981) 197-202.
Clark et al., "Recombinant adeno-associated viral vectors mediate long-term transgene expression in muscle," Human gene therapy, 1997, vol. 8, Issue 6, pp. 659-669.
Cordier et al., "Muscle-Specific Promoters May be Necessary for Adeno-Associated Virus-Mediated Gene Transfer in the Treatment of Muscular Dystrophies," Human Gene Therapy, Jan. 20, 2001, vol. 12, pp. 205-215.
Cordier et al., "Rescue of Skeletal Muscles of gamma-Sarcoglycan-Deficient Mice with Adeno-Associated Virus-Mediated Gene Transfer," Molecular Therapy, Feb. 2000, vol. 1, No. 2 pp. 119-129.
Cox et al., "Therapeutic genome editing: prospects and challenges," Nature Medicine, Feb. 21, 2015, vol. 2 (pp. 121-131).
D'Amario et al., Functionally competent cardiac stem cells can be isolated from endomyocardial biopsies of patients with advanced cardiomyopathies, Gire. Res. 108:857-61 (2011).
Database Genbank [online], Accession No. AJ277892.2, Nov. 14, 2006 issue.
Daya et al., "Gene Therapy Using Adeno-Associated Virus Vectors," Clinical Microbiology Reviews, Oct. 2008, vol. 21, No. 4 (pp. 583-593).
Deleavey et al., Chemical modification of siRNA, Curr. Protoc. Nucleic Acid Chem. Chapter 16:Unit 16.3 (2009).
Doench et al., "Optimized sgRNA design to maximize activity and minimize off-target effects of CRISPR-Cas9", Nature Biotechnology, Feb. 2016, vol. 34, No. 2 (pp. 184-191).
Draviam et al., The beta-Ii-core of sarcoglycan is essential for deposition at the plasma membrane, Muscle and Nerve. 34:691-701 (2006).
Dreier et al., "Development of Zinc Finger Domains for Recognition of the 5'-ANN-3' Family of DNA Sequences and Their Use in the Construction of Artificial Transcription Factors," The Journal of Biological Chemistry, Aug. 3, 2001, vol. 276, No. 31 (pp. 29466-29478).
Dreier et al., Insights into the molecular recognition of the 5'-GNN-3' family of DNA sequences by zinc finger domains, J. Mal. Biol. 303:489-502 (2000).
Dreier, B. et al., "Development of zinc finger domains for recognition of the 5'-CNN-3' family DNA sequence and their use in the construction of artificial transcription factors", The Journal of Biological Chemistry, vol. 280, No. 42, Oct. 21, 2005, pp. 35588-3597.
Dressman et al., Delivery of alpha- and beta-sarcoglycan by recombinant adeno-associated virus: efficient rescue of muscle, but differential toxicity, Hum. Gene. Ther., 13(13):1631-1646 (2002).
Dressman, AAV-Mediated gene transfer to models of muscular dystrophy: Insights into assembly of multi-subunit membrane proteins, University of Pittsburgh (1997).
Durbeej et al., Disruption of the beta-sarcoglycan gene reveals pathogenetic complexity of limb-girdle muscular dystrophy type 2E, Mol. Cell. 5:141-151 (2000).
Fanin et al., Gender difference in limb-girdle muscular dystrophy: a muscle fiber morphometric study in 101 patients, Clin. Neuropathology, 33:179-801 (2014).
Fanin et al., LGMD2E patients risk developing dilated cardiomyopathy, Neuromuscl. Disord., 13(4):303-309 (2003).
Fonfara et al., "Phylogeny of Cas9 determines functional exchangeability of dual-RNA and Cas9 among orthologous type II CRISPR-Cas systems", Nucleic Acids Research, vol. 42, No. 4, Nov. 22, 2013, pp. 2377-2590 (14 pages).
Forbes et al., "Skeletal muscles of ambulant children with Duchenne muscular dystrophy: validation of multicenter study of evaluation with MR imaging and MR spectroscopy", Radiology, 269:198-207 (2013).

(56) References Cited

OTHER PUBLICATIONS

Fowler, et al., Improved knockdown from artificial microRNAs in an enhanced miR-155 Backbone: a designer's guide to potent multi-target RNAi, Nucleic Acids Research, 44(5): e48, (Nov. 2015).

Foye, Whole Genome Sequencing Solved Our Family's Genetic Mystery: Titin, Narrat. Inq. Bioeth 5:206-8 (2015).

Francois, et al., Accurate Titration of Infectious AAV Particles Requires Measurement of Biologically Active Vector Genomes and Suitable Controls. Molecular Therapy—Methods & Clinical Development, Sep. 21, 2018, vol. 10, pp. 223-236.

Fucini et al., Adenosine modification may be preferred for reducing siRNA immune stimulation, Nucleic Acid Ther. 22:205-210 (2012).

Gaglione et al., Recent progress in chemically modified siRNAs, Mini. Rev. Med. Chem. 10:578-9t (2010).

Gao et al., A novel and efficient model of coronary artery ligation and myocardial infarction in the mouse, Gire. Res. 107:1445-53 (2010).

Gao et al., A novel and efficient model of coronary artery ligation in the mouse, Methods Mal. Bic 1037:299-311 (2013).

Gao et al., Adeno-associated viruses undergo substantial evolution in primates during natural infections, Proc. Natl. Acad. Sci. U.S.A., 2003, vol. 100, pp. 6081-6086.

Gautel et al., The central Z-disk region of titin is assembled from a novel repeat in variable copy numbers, Journal of Cell Science. 109:2747-2754 (1996).

Gebeyehu, et al., "Novel biotinylated nucleotide—analogs for labeling and colorimetric detection of DNA," Nucleic Acids Research, vol. 15, No. 11, (Jun. 11, 1987), p. 4513-4534.

GenBank Accession No. AF028704.1, Adena-associated virus 6, complete genome, Jan. 12, 1998.

GenBank Accession No. AF028705.1, Adeno-associated virus 3B, complete genome, Jan. 12, 1998.

GenBank Accession No. AF085716.1, Adeno-associated virus 5 DNA binding trs helicase (Rep22) and capsid protein (VP1) aenes, complete eds, Feb. 9, 1999.

Genbank Accession No. AX753246, Sequence 1 from Patent EP1310571, Jun. 23, 2003.

GenBank Accession No. AX753249, Sequence 4 from Patent EP1310571, Jun. 23, 2003.

GenBank Accession No. AX753250.1, Sequence 5 from Patent EP1310571, Jun. 23, 2003.

GenBank Accession No. AY631965.1, Adena-associated virus 10 nonstructural protein and caps protein genes, complete eds, Nov. 30, 2004.

GenBank Accession No. AY631966.1, Adena-associated virus 11 nonstructural protein and caps protein genes, complete eds, Nov. 30, 2004.

GenBank Accession No. DO813647.1, Adena-associated virus 12 Rep78 and VP1 genes, complete eds, Feb. 20, 2008.

GenBank Accession No. EU285562.1, Adena-associated virus 13 nonstructural protein and capsid protein genes, complete eds, Sep. 23, 2008.

GenBank Accession No. NC_001401.0, Adeno-associated virus-2, complete genome, Aug. 13, 2018.

GenBank Accession No. NC_001401.2, Adeno-associated virus—2, complete genome, Aug. 13, 2018.

Genbank Accession No. NC_001729.1, Adeno-associated virus- 3, complete genome, Aug. 13, 2018.

GenBank Accession No. NC_001829.1, Adeno-associated virus-4, complete genome, Aug. 13, 2018.

GenBank Accession No. NC_001862, Adeno-associated virus 6, complete genome, Jan. 12, 2004, located at <https:www.ncbi.nlm.nih.gov/nuccore/NC_001862.1?report=genbank>.

GenBank Accession No. NC_002077.1, Adeno-associated virus—1, complete genome, Aug. 13, 2018, located at <https://www.ncbi.nlm.nih.gov/nuccore/NC_002077>.

GenBank Accession No. NC_006152.1, Adeno-associated virus 5 complete genome, Aug. 13, 2018.

GenBank Accession No. NC_006260.1, Adeno-associated virus—7, complete genome, Aug. 13, 2018.

GenBank Accession No. NC_006261.1, Adeno-associated virus—8, complete genome, Aug. 13, 2018.

Genbank Accession No. NM_00232.4, *Homo sapiens* sarcoglycan beta {SGCB}, Mma, Feb. 20, 2019.

Genbank Accession No. NP 000233.1, Beta Sarcoglyan {43kD dystrophin-associated glycoprotein) *Homo sapiens*, Mar. 19, 1999.

GenBank Accession No. J01901, Adeno-associated virus 2, complete genome, Apr. 27, 1993.

GenBank Accession No. U89790.1, Adeno-associated virus 4, complete genome, Aug. 21, 2017.

GenBank Registered No. NG_011618, *Homo sapiens* titin (TTN), RefSeqGene (LRG_391) on chromosome 2, Apr. 5, 2020.

Genbank Synthetic construct *Homo sapiens* clone IMAGE:100069183, MGC:199194 anoctamin 5 (ANO5) mRNA, encodes complete protein GenBank: BC172489.1, Mar. 16, 2009.

GenBank: Accession No. NP 000223.1: beta-sarcoglycan sequence, dated Mar. 3, 1999.

Georganopoulou et al., "A Journey with LGMD: From Protein Abnormalities to Patient Impact", The Protein Journal, Kluwer Academic/Plenum Publishers, Dordrecht, NL, vol. 40, No. 4, Jun. 10, 2021, pp. 466-488.

Gerull et al., Identification of a novel frameshift mutation in the giant muscle filament titin in a large Australian family with dilated cardiomyopathy, J. Mal. Med. (Berl). 84:478-83 (2006).

Gerull et al., Mutations of TTN, encoding the giant muscle filament titin, cause familial dilated cardiomyopathy, Nat. Genet. 30:201-4 (2002).

Gibertini et al., Fibrosis and inflammation are greater in muscles of beta-sarcoglycan-null mouse than mdx mouse, Cell Tissue Res. 356:427-443 (2014).

Goeddel, "Gene Expression Technology: Methods in Enzymology," Academic Press, vol. 185, Jun. 11, 1990, pp. 3-7.

Gombash et al., Adeno-Associated Viral Vector Delivery to the Enteric Nervous System: A Review, Postdoc J., 2015, vol. 3, Issue 8, pp. 1-12.

Govoni et al., "Ongoing therapeutics trials and outcome measures for Duchenne muscular dystrophy", Cell Mol. Life Sci., 70:4585-602 (2013).

Graham et al., A new technique for the assay of infectivity of human adenovirus 5 DNA, Virology, 1973, vol. 52, Issue 2, pp. 456-467.

Gramlich et al., "Antisense-mediated exon skipping: a therapeutic strategy for titin-based dilated cardiomyopathy," EMBO Molecular Medicine, 7(5): 562-76 (2015).

Gramlich et al., "Stress-induced dilated cardiomyopathy in a knock-in mouse model mimicking human titin-based disease", J. Mal. Cell Cadiol. 47:352-8 (2009).

Granzier et al., "Deleting titin's I-band/A-band junction reveals critical roles for titin in biomechanica sensing and cardiac function", Proc. Natl. Acad. Sci. USA. 111:14589-94 (2014).

Greig et al., "Impact of intravenous infusion time on AAV8 vector pharmacokinetics, safety, and liver transduction in cynomolgus macaques," Molecular Therapy—Methods & Clinical Develop, 3:16079, 7 pages (2016).

Grieger et al., "Production and characterization of adeno-associated viral vectors", Nat. Protoc. 1 :1412-1428 (2006).

Griffin et al. Preclinical systemic delivery of adeno-associated [alpha]-sarcoglycan gene transfer for limb-qirdle muscular dystrophy, Human Gene Therapy, 32(7-8): 390-404, (Apr. 2021 ).

Griffin et al., Defective Membrane Fusion and Repair in Anoctamin5-Deficient Muscular Dystrophy, Human Molecular Genetics, vol. 25, No. 10, pp. 1900-1911 (Feb. 23, 2016).

Griffin et al., "Dose-Escalation of Systemically Delivered Adeno-Associated Virus-Mediated alpha-Sarcoglycan in a Mouse Model With Limb-Girdle Muscular Dystrophy Type 2D," Presented at the 2019 Muscular Dystrophy Association Clinical and Scientific Conference, Apr. 13-17, 2019. (Retrieved from: investorrelations.sarepta.com/staticfiles/8b00e773-3b86-4769-83dc-4d2bf22ffb0c).

Griffin et al., "Systemic Dose Escalation Study of Alpha-Sarcoglycan Provides Functional Improvement in SGCA (I-) Mouse Model of LGMD2D," Molecular Therapy, vol. 26, No. 5S1, May 2018, p. 166.

(56) References Cited

OTHER PUBLICATIONS

Grose et al., "Homologous Recombination Mediates Functional Recovery of Dysferlin Deficiency following AAV5 Gene Transfer", PLoS One, Jun. 2012, vol. 7, Issue 6, e39233.

Guilinger et al., "Fusion of catalytically inactive Cas9 to FokI nuclease improves the specificity of genome modification," Nature Biotechnology, vol. 32, No. 6, Jun. 2014 (pp. 577-582).

Gutschner et al., "Genome engineering—Matching supply with demand," Cell Cycle, 15(11): 1395-96 2016.

Hafez et al., "Homing endonucleases: DNA scissors on a mission", Genome. 55:553-69 (2012).

Hagan, "When are mice considered old?" The Jackson Laboratory, https://www.jax.org/news-and-insights/jax-blog/2017/november/when-are-mice-considered-old# Nov. 7, 2017 (8 pages).

Hakim et al., Monitoring murine skeletal muscle function for muscle gene therapy, Methods Mal. Biol., 2011, vol. 709, pp. 75-89.

Hakim et al., The passive mechanical properties of the extensor digitorum longus muscle are compromised in 2- to 20-mo-old mdx mice, J. Appl. Physiol. 110: 1656-1663 (2011).

Handschin et al., Peroxisome proliferator-activated receptor gamma coactivator 1 coactivators, energy homeostasis, and metabolism, Endocrine reviews, 27:728-735 (2002).

Herman et al., "Truncations of titin causing dilated cardiomyopathy", N. Engl. J. Med. 366:619-28, 2012.

Herson et al., A phase I trial of adeno-associated virus serotype 1-gamma-sarcoglycan gene therapy for limb girdle muscular type 2C, Brain, 2012, vol. 135, Pt 2, pp. 483-492.

Herzog et al., Stable gene transfer and expression of human blood coagulation factor IX after intramuscular injection of recombinant adeno-associated virus, Proc. Natl. Acad. Sci. USA, 1997, vol. 94 (pp. 5804-5809).

Hicks et al., A founder mutation in Anoctamin 5 is a major cause of limb-girdle muscular dystrophy, Brain, 134 (Pt. 1):171-82 (Jan. 2011).

Horii et al., Validation of microinjection methods for generating knockout mice by CRISPR/Cas-mediated genome engineering, Sci Rep. 4:4513 (2014).

Inouye et al., "Codon optimization of genes for efficient protein expression in mammalian cells by selection of only preferred human codons," Protein Expression and Purification, 2015, vol. 109, pp. 47-54.

International Application No. PCT/US20/47339, International Preliminary Report on Patentability, mailed Mar. 3, 2022, 8 pages.

International Application No. PCT/US2016/061703, International Preliminary Report on Patentability, mailed May 15, 2018, 10 pages.

International Application No. PCT/US2020/019892, International Preliminary Report on Patentability, mailed Sep. 10, 2021 (8 pages).

International Preliminary Report on Patentability for Appl. Ser. No. PCT/US2016/062052 dated May 22, 2018, 9 pages.

International Preliminary Report on Patentability for Appl. Ser. No. PCT/US2017/027583 dated Oct. 25, 2018, 5 pages.

International Preliminary Report on Patentability on PCT Appl. No. PCT/US2012/066265 dated May 27, 2014 (9 pages).

International Search report and Written Opinion for Appl. Ser. No. PCT/US2017/027583 dated Jul. 14, 2017 (8 pages).

International Search Report and Written Opinion for Appl. Ser. No. PCTUS2016/061703 dated Feb. 2, 2017 (13 pages).

International Search Report and Written Opinion on PCT Appl. No. PCT/US2012/066265 dated Mar. 28, 2013 (7 pages).

International Search Report and Written Opinion on PCT Appl. No. PCT/US2020/047339 dated Dec. 10, 2020 (12 pages).

International Search Report for Appl. Ser. No. PCT/US2016/062052 dated Feb. 7, 2017 (5 pages).

International Search Report issued in connection with PCT/US2020/019892 dated May 14, 2020 (4 pages).

Itoh-Satoh et al., Titan mutations as the molecular basis for dilated cardiomyopathy, Biochem. Biophys. Res. Commun. 291:385-93 (2002).

Jaber et al., Titin isoforms, extracellular matrix, and global chamber remodeling in experimental dilated cardiomyopathy: functional implications and mechanistic insight, Circ. Heart Fail. 1:192-9 (2008).

Jinek et al., "A Programmable Dual-RNA-Guided DNA Endonuclease in Adaptive Bacterial Immunity," Science, Aug. 17, 2012, 337(6096):816-821.

John Hopkins Medicine, "Types of Muscular Dystrophy and Neuromuscular diseases," 2023, 6 pages.

Judge et al., "Design of noninflammatory synthetic siRNA mediating potent gene silencing in vivo", Mol. Ther. 13:494-505 (2006).

Justison et al., Percutaneous assisted venous return isolated limb perfusion, J. Extra Corpor. Technol., 2009, vol. 41, Issue 4, pp. 231-234.

Kajigaya et al., Self-assembled B19 parvovirus caps ids, produced in a baculovirus system, are antigenically and immunogenically similar to native virions, Proc. Natl. Acad. Sci. USA, 88(11):4646-50 (Jun. 1991).

Kariko et al., "Suppression of RNA recognition by Toll-like receptors: the impact of nucleoside modification and the evolutionary origin of RNA," Immunity, Aug. 2005, vol. 23 (pp. 165-175).

Kennell, "Principles and Practices of Nucleic Acid Hybridization," Progress in Nucleic Acid Research and Molecular Biology, Academic Press, vol. 11, 1971, (pp. 259-301).

Kent et al., "Mechanism of microhomology-mediated end-joining promoted by human DNA polymerase theta", Nat. Struct. Mol. Biol. 22:230-237 (2015).

Kessler et al., "Gene delivery to skeletal muscle results in sustained expression and systemic delivery of a therapeutic protein," PNAS, 1996, vol. 93, pp. 14082-14087.

Kirnbauer et al., Virus-like particles of bovine papillomavirus type 4 in prophylactic and therapeutic immunization, Virology, 219(1):37-44 (May 1996).

Kleinstiver et al., The I-TevI nuclease and linker domains contribute to the specificity of monomerh TALENs, G3 (Bethesda). 4:1155-65 (2014).

Kobayashi et al., Sarcolemma-localized nNOS is required to maintain activity after mild exercise, Nature. 456:511-5 (2008).

Kole et al., "RNA therapeutics: beyond RNA interference and antisense oligonucleotides", Nat Rev Drug Discov. Jan. 20, 2012;11(2):125-40. doi: 10.1038/nrd3625.

Kolmerer et al., "Genomic organization of M line titin and its tissue-specific expression in two distinct isoforms", J. Mol. Biol. 256:556-63 (1996).

Kormann et al., "Expression of therapeutic proteins after delivery of chemically modified mRNA in mice," Nature Biotechnology, Feb. 2011, vol. 29, No. 2 (pp. 154-157).

Kornberg et al., "The early history of DNA polymerase: a commentary by Arthur Kornberg", Biochimica et Biophysica Acta. 1000:53-56 (1989).

Kotin et al., "Manufacturing Clinical Grade Recombinant Adeno-Associated Virus Using Invertebrate Cell Lines," Human Gene Therapy, 28(4):Abstract Only, (Apr. 1, 2017).

Kotin et al., Manufacturing Clinical Grade Recombinant Adeno-Associated Virus Using Invertebrate Cell Lines, Hum. Gene Ther., 28(4):350-360 (2017).

Kramerova et al., Failure to up-regulate transcription of genes necessary for muscle adaptation underlies limb girdle muscular dystrophy 2A calpainopathy, Hum. Mol. Genet., 25(11):2194-2207 (2016).

Labeit et al., "Titins: giant proteins in charge of muscle ultrastructure and elasticity", Science. 270:293-6 (1995).

Laws et al., Progression of kyphosis in mdx mice, J. Appl. Physiol. 97:1970-7 (2004).

Lewinter et al., Cardiac titin and heart disease, J. Cardiovasc. Pharmacol. 63:207-12 (2014).

Lewinter, "Titin isoforms in heart failure: are there benefits to supersizing", Circulation. 110:109-11 2004.

Lewis et al., "Generation of neutralizing activity against human immunodeficiency virus type 1 in serum by antibody gene transfer," Journal of virology, 2002, vol. 76, Issue 17, pp. 8769-8775.

(56) References Cited

OTHER PUBLICATIONS

Li et al., "Modularly assembled designer TAL effector nucleases for targeted gene knockout and gene replacement in eukaryotes," Nucleic Acids Research, 2011, vol. 39, No. 14 (pp. 6315-6325).

Li et al., Electrical impedance myography for the in vivo and ex vivo assessment of muscular dystrophy (mdx) mouse muscle, Muscle Nerve, 49(6):829-35 (Jun. 2014).

Li et al., Electrophysiologic biomarkers for assessing disease progression and the effect of riluzole in SOD1 G93A ALS mice, PLoS One, 8(6):e65976 (Jun. 2013).

Li et al., Intracoronary administration of cardiac stem cells in mice: a new, improved technique for cell therapy in murine models, Basic Res. Cardiol. 106:849-64 (2011).

Lin et al., Transcriptional co-activator PGC-1 alpha drives the formation of slow-twitch muscle fibres, Nature, 418:797-801 (2002).

Liu et al., "Adeno-associated virus-mediated microdystrophin expression protects young mdx muscle from contraction-induced injury," Molecular therapy: the journal of the American Society of Gene Therapy, 2005, vol. 11, Issue 2, pp. 245-256.

Liu et al., "Validated Zinc Finger Protein Designs for All 16 GNN DNA Triplet Targets," The Journal of Biological Chemistry, Feb. 8, 2002, vol. 277, No. 6 (pp. 3850-3856).

Louis et al., "EM_EST:BE676391", Jan. 27, 2011 (Jan. 27, 2011), XP055708767, Retrieved from the Internet: URL:http://ibis.internal.epo.org/exam/dbfetch.jsp?id=EM_EST:BE676391 [retrieved on Jun. 25, 2020].

Ma et al., Pol III Promoters to express small RNAs: Delineation of transcription initiation, Mol. Ther. Nucleic Acids. 3:e161 (2014).

Mahmood et al., "Limb-girdle muscular dystrophies: Where next after six decades from the first proposal (review)," Molecular Medicine reports, 2014, vol. 9 (pp. 1515-1532).

Mak et al., "The crystal structure of TAL effector PthXo1 bound to its DNA target," Science, Feb. 10, 2012, vol. 335, No. 6069 (pp. 716-719).

Makarenko et al., Passive stiffness changes caused by upregulation of compliant titin isoforms in human dilated cardiomyopathy hearts, Gire. Res. 95:708-16 (2004).

Martin et al., Overexpression of Galgt2 in skeletal muscle prevents injury resulting from eccentric contractions in both mdx and wild-type mice, Am. J. Physiol. Cell Physiol., vol. 296, pp. 476-488, Dec. 24, 2008.

Mashiko et al., Generation of mutant mice by pronuclear injection of circular plasmid expressing Cas9 and single guided RNA, Sci. Rep. 3:3355 (2013).

Mateos-Gomez et al., Mammalian Polymerase theta promotes alternative-NHEJ amd suppresses recombination, Nature. 518:254-257 (2015).

Matsuda et al., Visualization of dystrophic muscle fibers in mdx mouse by vital staining with Evans blue: evidence of apoptosis in dystrophin-deficient muscle, J. Biochem., 118(5):959-964 (1995).

McCarty et al., "Adeno-associated virus terminal repeat (TR) mutant generates self-complementary vectors to overcome the rate-limiting step to transduction in vivo", Gene Therapy, vol. 10, May 30, 2003, pp. 2112-2118.

McCarty et al., "Self-complementary recombinant adeno-associated virus (scAAV) vectors promote efficient transduction independently of DNA synthesis", Gene Therapy, May 22, 2001, vol. 8, pp. 1248-1254.

McNally et al., "Mild and Severe Muscular Dystrophy Caused by a Single gamma-Sarcoglycan Mutation", American Journal of Human Genetics, Nov. 1996, vol. 59, No. 5, pp. 1040-1047.

McNally et al., The genetic landscape of cardiomyopathy and its role in heart failure, Cell. Metab. 21:174-182 (2015).

Meadows et al., Micro-RNA-29 Overexpression by adeno-associated virus suppresses fibrosis in mdx: utrn+/− Mice (S61.003), Neurology, 82:S61.003 (Abstract) (2014).

Meadows et al., Reducing Skeletal Muscle Fibrosis with AAV-Delivered miR-29, 2012, Neurology, vol. 78, Issue 1, Supplement PO4.089.

Melacini et al., Heart involvement in muscular dystrophies due to sarcoglycan gene mutations, Muscle Nerve. 22:473-479 (1999).

Mendell et al., "A phase 1/2a follistatin gene therapy trial for becker muscular dystrophy," Molecular therapy : the journal of the American Society of Gene Therapy, 2015, vol. 23, Issue 1, pp. 192-201.

Mendell et al., "Gene Therapy for Muscular Dystrophy: Lessons Learned and Path Forward", Neuroscience Letters, vol. 527, No. 2, Oct. 2012, 21 pages.

Mendell et al., "Limb-girdle muscular dystrophy type 2D gene therapy restores alpha-sarcoglycan and associated proteins," Ann. Neural., 2009, vol. 66 Issue 3, pp. 290-297.

Mendell et al., "Sustained alpha-sarcoglycan gene expression after gene transfer in limb-girdle muscular dystrophy, type 2D," Annals of neurology, 2010, vol. 68, Issue 5, pp. 629-638.

Mendell et al., Gene Delivery for Limb-Girdle Muscular Dystrophy Type 2D by Isolated Limb Infusion, Human Gene Therapy, 2019, vol. 30, Issue 7, pp. 794-801.

Mendell et al., Gene Therapy for Spinal Muscular Atrophy Type 1 Shows Potential to Improve Survival and Motor Functional Outcomes, Mol. Ther. 24:S190 (2016).

Mendell et al., Single-Dose Gene-Replacement Therapy for Spinal Muscular Atrophy, N. Engl. J. Med., 377:1713-1722 (2017).

Merten, O.W., AAV vector production: state of the art developments and remaining challenges. Cell and Gene Therapy Insights, Dec. 1, 2016, vol. 2, No. 5, pp. 521-551.

Mingozzi et al. "Therapeutic in vivo gene transfer for genetic disease using AAV: progress and challenges", Nature Reviews Genetics, May 2011, vol. 12 (pp. 341-355).

Monjaret et al., "The Phenotype of Dysferlin-Deficient Mice is not Rescued by Adeno-Associated Virus-Medicated Transfer of Anoctamin 5," Human Gene Therapy Clinical Development, 24(2):65-76 (Jun. 1, 2013).

Moore et al., Limb-girdle muscular dystrophy in the United States, J. Neuropathol. Exp. Neural., 65(10):995-1003 (2006).

Moorwood et al., Isometric and eccentric force generation assessment of skeletal muscles isolated from murine models of muscular dystrophies, Journal of Visualized Experiments. 71 :e50036 (2013).

Moscou et al., "A Simple Cipher Governs DNA Recognition by TAL Effectors", Science, Dec. 11, 2009, vol. 326 (p. 1501).

Murphy et al., "Long-term correction of obesity and diabetes in genetically obese mice by a single intramuscular injection of recombinant adeno-associated virus encoding mouse leptin," Proceedings of the National Academy of Sciences of the United States of America, 1997, vol. 94, Issue 25, pp. 13921-13926.

Narayanaswami et al., Evidence-based guideline summary: diagnosis and treatment of limb-girdle and distal dystrophies: report of the guideline development subcommittee of the American Academy of Neurology and the practice issues review panel of the American Association of Neuromuscular & Electrodiagnostic Medicine, Neurology, 83:1453-1463 (2014).

NCBI Accession No. NG_051363.1, Homo sapiens TTN antisense RNA 1 (TTN-AS1), RefSeqGene on chromosome 2, dated Feb. 17, 2020.

NCBI Accession No. XM_012650762.1, Predicted:Propithecus coquereli titin (TTN), mRNA, dated Jun. 1, 2015.

NCBI Accession No. XM_024453100.1, Predicted:Homo sapiens titin (TTN), transcript variant X12, mRNA, dated Mar. 1, 2020.

NCBI Reference Sequence: "anoctamin-5 isoform a [Homo sapiens]", GenPept, Mar. 15, 2015, NP_998764.1.

NCBI, GenBank accession No. U34976.1 (Nov. 8, 1995), 2 pages.

Noguchi S, "Human gamma-sarcoglycan mRNA, complete cds.", NCBI, (Nov. 8, 1995), Database accession No. U34976, 2 pages.

Obermann et al., Molecular structure of the sarcomeric M band: mapping of titin and myosin binding domains in myomesin and the identification of a potential regulatory phosphorylation site in myomesin, EMBO J. 16:211-20 (1997).

Pacak et al., Long-term Skeletal Muscle Protection After Gene Transfer in a Mouse Model of LGMD-2D, Molecular Therapy, 2007, vol. 15, Issue 10, pp. 1775-1781.

Pavlovicova et al., Structure and composition of tubular aggregates of skeletal muscle fibres, Gen. Physiol. Biophys., 22(4):425-40 (Dec. 2003).

(56) References Cited

OTHER PUBLICATIONS

Payne et al., Nutritional therapy improves function and complements corticosteroid intervention in mdx mice. Muscle Nerve. Jan. 2006; 33(1):66-77.
Peer et al., Special delivery: targeted therapy with small RNAs, Gene. Ther. 18:1127-33 (2011).
Peled et al., Titin mutation in familial restrictive cardiomyopathy, Int. J. Cardiol. 171:24-30 (2014).
Penttila et al., Eight new mutations and the expanding phenotype variability in muscular dystrophy caused by ANOS, Neurology, 78(12):897-903 (Mar. 2012).
Powers et al., Exercise-induced oxidative stress in humans: cause and consequences, Free Radic. Biol. Med., 51 (5):942-50 (Sep. 2011).
Pozsgai et al., "Beta-Sarcoglycan gene transfer decreases fibrosis and restores force in LGMD2E mice," Gene Therapy, 2016, vol. 23 (pp. 57-66).
Pozsgai et al., "Beta-Sarcoglycan Gene Transfer Leads to Functional Improvement in a Model of LGMD2E," Molecular Therapy vol. 22, Supplement 1, May 2014 (p. S199).
Pozsgai et al., "Pre-Clinical Efficacy Study of Beta-Sarcoglycan Gene Transfer," Molecular Therapy, May 1, 2013, vol. 21, No. 1 (p. S68).
Pozsgai et al., "Systemic AAV-Mediated [beta]-Sarcoglycan Delivery Targeting Cardiac and Skeletal Muscle Ameliorates Histological and Functional Deficits in LGMD2E Mice," Molecular Therapy, The Journal of the American Society of Gene Therapy, Apr. 2017, vol. 25, No. 4 (pp. 855-869).
Rafael-Fortney et al., Early treatment with lisinopril and spironolactone preserves cardiac and skeletal muscle in duchenne muscular dystrophy mice, Circulation. 124:582-8 (2011).
Raj et al., "Self-complementary adeno-associated viral vectors for gene therapy of hemophilia B: progress and challenges" Expert Review of Hematology, Oct. 2011, vol. 4, No. 5 (pp. 539-549).
Ran et al., "In vivo genome editing using *Staphylococcus aureus* Cas9," Nature, Apr. 9, 2015, vol. 520, (18 pages).
Roberts et al., Integrated allelic, transcriptional, and phenomic dissection of the cardiac effects of titin truncations in health and disease, Sci. Transl. Med. 7:270ra6 (2015).
Rodino-Klapac et al., "Persistent expression of FLAG-tagged micro dystrophin in nonhuman primates following intramuscular and vascular delivery," Molecular therapy: the journal of the American Society of Gene Therapy, 2010, vol. 18, Issue 1 (pp. 109-117).
Rodino-Klapac et al., Demonstration of SGCA Expression and Related Outcomes in Phase I/IIa Safety Isolated Limb Perfusion Trial in LGMD2D Subjects, Molecular Theerapy, 2018, vol. 26, Issue 5, Supplemental 1, p. 1, Abstract No. 250.
Rodino-Klapac et al., Lack of toxicity of alpha-sarcoglycan overexpression supports clinical gene transfer trial in LGMD2D, Neurology, 2008, vol. 71, Issue 4, pp. 240-247.
Rose, comprehensive Virology 3:1-61 (1974).
Ruffing et al., "Mutations in the carboxy terminus of adeno-associated virus 2 capsid proteins affect viral infectivity: lack of an RGD integrin-binding motif," Journal of General Virology, 1994, vol. 75, pp. 3385-3392.
Rutledge et al., Infectious clones and vectors derived from adeno-associated virus (AAV) serotypes other than AAV type 2, J. Viral., 7291):309-19 (Jan. 1998).
Sahenk et al., Systemic delivery of AAVrh74.tMCK.hCAPN3 rescues the phenotype in a mouse model for LGMD2A/R1, Mol. Ther. Methods Clin. Dev., 22:401-414 (2021).
Salva et al., "Design of Tissue-specific Regulatory Cassettes for High-level rAAV-mediated Expression in Skeletal and Cardiac Muscle," Mol. Ther., 2007, vol. 15, Issue 2, pp. 320-329.
Sambrook et al., Cold spring harbor laboratory press, cold Spring Harbor, N.Y., (2001).
Sambrook et al., Molecular Cloning: A Laboratory Manual, 2 edition (1989).
Sander et al., CRISPR-Cas systems for editing, regulating and targeting genomes, Nat. Biotechnol. 32:347-55 (2014).

Sandona et al., Sarcoglycanopalhies: molecular pathogenesis and therapeutic prospects, Exp Rev. Mol. Med. 11:e28 (2009).
Sanganalmath et al., Cell therapy for heart failure: a comprehensive overview of experimental and clincal studes, current challenges, and future directions, Gire. Res. 113:810-34 (2013).
Sarepta Therapeutics: "Sarepta Therapeutics' Investigational Gene Therapy SRP-9003 for the Treatment of Limb-Girdle Muscular Dystrophy Type 2E Shows Sustained Expression and Functional Improvements 2 Years After Administration", Mar. 18, 2021, pp. 1-3, Retrieved from the Internet: URL: https://investorrelations.sarepta.com/news--releases/news-release-details/sarepta-therapeutics-investigational-gene-therapy-srp-9003-0 [retrieved on Jun. 23, 2023].
Schreiber et al., The transcriptional coactivator PGC-1 regulates the expression and activity of the orphan nuclear receptor estrogen-related receptor alpha (ERRalpha), J. Biol. Chem., 278: 9013-9018 (2003).
Segal et al., "Toward controlling gene expression at will: Selection and design of zinc finger domains recognizing each of the 5'-GNN-3' DNA target sequences," Proceedings of the National Academy of Sciences, USA, Mar. 1999, vol. 96 (pp. 2758-2763).
Semplicini et al., Clinical and genetic spectrum in limb-girdle muscular dystrophy type 2E, Neurology, 84:1772-81 (2015).
Shield et al., E-box sites and a proximal regulatory region of the muscle creatine kinase gene differentially regulate expression in diverse skeletal muscles and cardiac muscle of transgenic mice, Mal. Cell. Biol., 16(9):5058-5068 (1996).
Shih et al., Finding the Achilles' heel of Muscle Giant-TALEN-mediated Gene-editing in Zebrafish Titin, Circulation Research, Oct. 21, 2015, vol. 117, No.(suppl_1), pp. A344. DOI: https://doi.org/10.1161/res.117.suppl_1.344.
Siu et al., Familial dilated cardiomyopathy locus maps to chromosome 2q31, Circulation. 99:1022-6 (1999).
Smith et al., Modification and secretion of human interleukin 2 produced in insect cells by a baculovirus expression vector, Proc. Natl. Acad. Sci. USA, 82(24):8404-8 (1985).
Sondergaard et al., "AAV.Dysferlin Overlap Vectors Restore Function in Dysferlinopathy Animal Models," Annals of Clinical and Translational Neurology, 2015, vol. 2, Issue 3, pp. 256-270.
Sonntag et al., A viral assembly factor promotes AAV2 capsid formation in the nucleolus, PNAS,2010, vol. 107, Issue 22, pp. 10220-10225.
Sorimachi et al., Tissue-specific expression and alpha-actinin binding properties of the Z-disc titin: implications for the nature of vertebrate Z-discs, J. Mal. Biol. 270:688-95 (1997).
Soutschek et al., "Therapeutic silencing of an endogenous gene by systemic administration of modified siRNAs," Nature, Nov. 2004, pp. 173-178, vol. 432.
Steentoft et al., Precision genome editing: a small revolution for glycobiology, Glycobiology. 24:663-80 (2014).
Straub et al., Animal models for muscular dystrophy show different patterns of sarcolemmal disruption, J. Cell Biol. 139:375-385 (1997).
Strobel, et al. "Antioxidant Supplementation Reduces Skeletal Muscle Mitochondrial Biogenesis", Official Journal of the American College of Sports Medicine, 2011, pp. 1017-1024.
Sun et al., Correction of Multiple Striated Muscles in Murine Pompe Disease Through Adena-Associated Virus-mediated Gene Therapy, Mal. Ther., 16(8):1366-71 (2008).
Sveen et al., Cardiac involvement in patients with limb-girdle muscular dystrophy type 2 and Becker muscular dystrophy, Arch. Neurol., 65(9):1196-1201 (2008).
Thiruvengadam et al., "Anoctamin 5 Knockout Mouse Model Recapitulates LGMD2L Muscle Pathology and Offers Insight Into in vivo Functional Deficits," Journal of Neuromuscular Diseases, 2021, vol. 8 (S243-S255).
Torella, et al., "Cardiovascular development: towards biomedical applicability; Resident cardiac stem cells", CMLS Cellular and Molecular Life Sciences 64(6): 661-673 (2007).
Tsai et al., "GUIDE-seq enables genome-wide profiling of off-target cleavage by CRISPR-Cas nucleases," Nature Biotechnology, Feb. 2015, vol. 33, No. 2 (pp. 187-197).
Tsai et al., Dimeric CRISPR RNA-guided FokI nucleases for highly specific genome editing, Nat. Biotechnol. 32:569-76 (2014).

(56) References Cited

OTHER PUBLICATIONS

Van Akkooi et al., Isolated limb perfusion for an irresectable melanoma recurrence in a Jehovah's witness, Eur. J. Cardiothorac. Surg., 2006, vol. 30, Issue 2, pp. 408-410.
Voikar et al., Long-term individual housing in C57BU6J and DBA/2 mice: assessment of behavioral consequences, Genes Brain Behav., 4(4):240-52 (2005).
Volkov et al., Selective protection of nuclease-sensitive sites in siRNA prolongs silencing effect, Oligonucleotides. 19:191-202 (2009).
Wang et al., Loss of miR-29 in myoblasts contributes to dystrophic muscle pathogenesis, Mol. Ther., 20(6):1222-33 (2012).
Wang et al., Rapid and efficient assembly of transcription activator-like effector genes by USER cloning, J. Genet. Genomics. 41:339-47 (2014).
Wang et al., Recombinant AAV serotype 1 transduction efficiency and tropism in the murine brain, Gene Ther., 2003, vol. 10, Issue 17, pp. 1528-1534.
Watson et al., "Recombinant DNA," Scientific American, Second Edition, 2001 (pp. 153-154).
Weber et al., "A Modular Cloning System for Standardized Assembly of Multigene Constructs," Feb. 2011, vol. 6, No. 2, e16765 (11 pages).
Whitehead et al., Silencing or stimulation? siRNA delivery and the immune system, Annual Review of Chemical and Biomolecular Engineering. 2:77-96 (2011).
Wikipedia, "Adeno-associated virus," downloaded Dec. 29, 2017 (pp. 1-18).
Wikipedia, "Limb-girdle muscular dystrophy," 11 pages, Retrieved Oct. 26, 2023, from https://en.wikipedia.org/wiki/Limb-girdle_muscular_dystrophy (11 pages).
Winkler, Oligonucleotide conjugates for therapeutic applications, Ther. De/iv. 4:791-809 (2013).
Witting et al: "Anoctamin 5 muscular dystrophy in Denmark: prevalence, genotypes, phenotypes, cardiac findings, and muscleprotein expression", Case Reports, May 14, 2013, PMID: 23670307 DOI: 10.1007/s00415-013-6934-y.
Wolfs et al., MegaTevs: single-chain dual nucleases for efficient gene disruption, Nucliec Acids Res. 42:8816-29 (2014).
Wong-Kisiel et al., Two siblings with limb-girdle muscular dystrophy type 2E responsive to deflazacort, Neuromusc. Disord. 20:122-124 (2010).
Wu et al., Mutational analysis of the adeno-associated virus type 2 (AAV2) capsid gene and construction of AAV2 vectors with altered tropism, J. Viral., 74(18):8635-47 (Sep. 2000).
Xiao et al. "Production of High-Titer Recombinant Adeno-Associated Virus Vectors in the Absence of Helper Adenovirus," Journal of Virology, Mar. 1998, vol. 72 No. 3 (pp. 2224-2232).
Xiao et al., "Efficient long-term gene transfer into muscle tissue of immunocompetent mice by adeno-associated virus vector," Journal of virology, 1996, vol. 70, Issue 11, pp. 8098-8108.
Xu et al., "An Isolated Limb Infusion Method Allows for Broad Distribution of rAAVrh74.MCK.GALGT2 to Leg Skeletal Muscles in the Rhesus Macaque," Molecular Therapy—Methods & Clinical Develop, 10:89-104 (Sep. 2018).
Xu et al., "Genetic disruption of Ano5 in mice does not recapitulate human ANO5-deficient muscular dystrophy," Skeletal Muscle, 2015, vol. 5, No. 43 (pp. 1-14).
Xu et al., Postnatal overexpression of the CT GalNAc transferase inhibits muscular dystrophy in mdx mice without altering muscle growth or neuromuscular development: evidence for a utrophin-independent mechanism, Neuromuscul. Disord., 2007, vol. 17, Issue 3, pp. 209-220.
Yan et al., Inverted terminal repeat sequences are important for intermolecular recombination and circularization of adeno-associated virus genomes, J. Viral., 79(1):364-79 (Jan. 2005).
Yuasa et al., "Gene therapy of muscular dystrophy: Systemic gene delivery to skeletal muscles" Jan. 2007, Drug Delivery System 22(2):140-147, doi.org/10.2745/dds.22.140 (English Abstract).

Zanotti et al., Opposing roles of miR-21 and miR-29 in the progression of fibrosis in Duchenne muscular dystrophy., Biochem. Biophys. Acta., 1852:1451-4 (2015).
Zetsche at el., "Cpf1 Is a Single RNA-Guided Endonuclease of a Class 2 CRISPR-Cas System," Cell, Oct. 22, 2015, vol. 163, No. 3 (pp. 759-771).
Zhang et al., Dual AAV therapy ameliorates exercise-induced muscle injury and functional ischemia in murine models of Duchenne muscular dystrophy, Hum. Mal. Genet. 22:3720-9 (2013).
Zhao et al., BPV1 E2 protein enhances packaging of full-length plasmid DNA in BPV1 pseudovirions, Virology, 272(2):382-93 (Jul. 2000).
Zhou et al., Pressure Overload by Transverse Aortic Constriction Induces Maladaptive Hypertrophy in a Titin-Truncated Mouse Model, Biomed. Res. Int. 2015:163564 (2015).
Zou et al., "An internal promoter underlies the difference in disease severity between N- and C-terminal truncation mutations of Titin in zebrafish", eLife, Oct. 16, 2015, vol. 4, pp. e09406. DOI:https://doi.org/10.7554/eLife.09406.
Dorange et al., "Analytical approaches to characterize AAV vector production & purification: Advances and challenges," Cell & Gene Therapy Insights, 4(2):119-129 (2018).
Hou et al., "Serious Overestimation in Quantitative PCR by Circular (Supercoiled) Plasmid Standard: Microalgal pcna as the Model Gene," PLoS One 5(3):e9545, 8 pages (Mar. 5, 2010) doi:10.1371/journal.pone.0009545.
Martinez-Fernandez de la Camara et al., "The accurate quantification of AAV genomic titre depends on the conformation of the plasmid reference," ARVO Annual Meeting Abstract, 3 pages, Jul. 2018.
Thomas et al., "B4GALNT2 (GALGT2) Gene Therapy Reduces Skeletal Muscle Pathology in the FKRP P448L Mouse Model of Limb Girdle Muscular Dystrophy 2I", Am. J_ Pathol., 186(9):2429-2448 (2016).
Werling et al., "Systematic comparison and validation of quantitative real-time PCR methods for the quantitation of adeno-associated viral products," Human Gene Therapy Methods, 26.3:82-92 (Jun. 2015).
Pozsgai et al., "506. [beta]—Sarcoglycan Gene Transfer Prevents Muscle Fibrosis and Inflammation in an Aged LGMD2E Mouse Model," Molecular Therapy, vol. 23 Supplement 1, May 2015, 2 pages.
Chu et al., "The limb-girdle muscular dystrophies: is treatment on the horizon?" Neurotherapeutics, 15(4):849-862 (Oct. 2018).
Monies et al., "A first-line diagnostic assay for limb-girdle muscular dystropy and other nyopathies", Human Genomics, 10(1):32, pp. 1-7 (Sep. 27, 2016).
Theadom et al., "Prealence of muscular dystrophies: a systematic literature review," Neuroepidemiology 43(3-4):259-68 (2014).
Wagner et al., "A novel method for the quantification of adeno-associated virus vectors for RNA interference applications using quantitative polymerase chain reaction and purified genomic adeno-associated virus DNA as a standard," Human Gene Therapy Methods, 24(6):355-63 (Dec. 2013).
Walter et al., "Recent developments in Duchenne muscular dystrophy: facts and numbers," Journal of Cachexia, Sarcopenia and Muscle, 8(5):681-685 (Oct. 2017).
Hartigan-O'Connor et al., "Developments in gene therapy for muscular dystrophy," Microscopy Research and Technique 48:223-238 (2000).
Pozsgai, E.R., Adeno-Associated Virus Mediated β-Sarcoglycan Gene Replacement Therapy for the Treatmentof Limb Girdle Muscular Dystrophy Type 2E [Doctoral dissertation, Ohio State University]. OhioLink Electronic Theses and Dissertations Center. (2016) http://rave.ohiolink.edu/etdc/view?acc_num=osu147697211337827.
Agbandje-McKenna et al., "AAV Capsid Structure and Cell Interactions", Adeno-Associated Virus: Methods and Protocols, in Methods in Molecular Biology, Ch. 3, 807:47-92 (2011).

\* cited by examiner

RECOMBINANT ADENO-ASSOCIATED VIRUS PRODUCTS AND METHODS FOR TREATING LIMB GIRDLE MUSCULAR DYSTROPHY 2A

This application is a U.S. 371 National Stage Application of PCT International Application No. PCT/US19/39893, filed Jun. 28, 2019, which claims priority to U.S. Provisional Patent Application No. 62/691,934, filed Jun. 29, 2018 and U.S. Provisional Patent Application No. 62/865,081, filed Jun. 21, 2019, the contents of each of which are incorporated herein by reference in their entirety.

Provided herein are products and methods for treating limb girdle muscular dystrophy 2A. In the methods, recombinant adeno-associated viruses deliver DNA encoding a protein with calpain3 (CAPN3) activity.

INCORPORATION BY REFERENCE OF THE SEQUENCE LISTING

This application contains, as a separate part of disclosure, a Sequence Listing in computer-readable form (filename: 52684P2_SeqListing.txt; 23,755 bytes—ASCII text file created Jun. 26, 2019) which is incorporated by reference herein in its entirety.

BACKGROUND

Muscular dystrophies (MDs) are a group of genetic diseases. The group is characterized by progressive weakness and degeneration of the skeletal muscles that control movement. Some forms of MD develop in infancy or childhood, while others may not appear until middle age or later. The disorders differ in terms of the distribution and extent of muscle weakness (some forms of MD also affect cardiac muscle), the age of onset, the rate of progression, and the pattern of inheritance.

One group of MDs is the limb girdle group (LGMD) of MDs. LGMDs are rare conditions and they present differently in different people with respect to age of onset, areas of muscle weakness, heart and respiratory involvement, rate of progression and severity. LGMDs can begin in childhood, adolescence, young adulthood or even later. Both genders are affected equally. LGMDs cause weakness in the shoulder and pelvic girdle, with nearby muscles in the upper legs and arms sometimes also weakening with time. Weakness of the legs often appears before that of the arms. Facial muscles are usually unaffected. As the condition progresses, people can have problems with walking and may need to use a wheelchair over time. The involvement of shoulder and arm muscles can lead to difficulty in raising arms over head and in lifting objects. In some types of LGMD, the heart and breathing muscles may be involved.

There are at least nineteen forms of LGMD, and the forms are classified by their associated genetic defects.

| Type | Pattern of Inheritance | Gene or Chromosome |
| --- | --- | --- |
| LGMD1A | Autosomal dominant | Myotilin gene |
| LGMD1B | Autosomal dominant | Lamin A/C gene |
| LGMD1C | Autosomal dominant | Caveolin gene |
| LGMD1D | Autosomal dominant | Chromosome 7 |
| LGMD1E | Autosomal dominant | Desmin gene |
| LGMD1F | Autosomal dominant | Chromosome 7 |
| LGMD1G | Autosomal dominant | Chromosome 4 |
| LGMD2A | Autosomal recessive | Calpain-3 gene |
| LGMD2B | Autosomal recessive | Dysferlin gene |
| LGMD2C | Autosomal recessive | Gamma-sarcoglycan gene |
| LGMD2D | Autosomal recessive | Alpha-sarcoglycan gene |
| LGMD2E | Autosomal recessive | Beta-sarcoglycan gene |
| LGMD2F | Autosomal recessive | Delta-sarcoglycan gene |
| LGMD2G | Autosomal recessive | Telethonin gene |
| LGMD2H | Autosomal recessive | TRIM32 |
| LGMD2I | Autosomal recessive | FKRP gene |
| LGMD2J | Autosomal recessive | Titin gene |
| LGMD2K | Autosomal recessive | POMT1 gene |
| LGMD2L | Autosomal recessive | Fukutin gene |

Specialized tests for LGMD are now available through a national scheme for diagnosis, the National Commissioning Group (NCG).

Mutations in calpain3 gene (CAPN3) lead to one of the most common limb-girdle muscular dystrophies worldwide, LGMD2A. At present, there is no treatment for this inherited disease. Previous studies have demonstrated the potential for CAPN3 gene transfer to correct the pathological signs in CAPN3-deficient mice. However expression of CAPN3 driven by desmin promoter resulted in cardiotoxicity [Bartoli et al., *Mol. Ther.*, 13: 250-259 (2006)]. In follow up studies, skeletal muscle expression of the gene was studied [Roudaut et al., *Circulation*, 128: 1094-1104 (2013)].

Adeno-associated virus (AAV) is a replication-deficient parvovirus, the single-stranded DNA genome of which is about 4.7 kb in length including two 145 nucleotide inverted terminal repeat (ITRs). There are multiple serotypes of AAV. The nucleotide sequences of the genomes of AAV serotypes are known. For example, the complete genome of AAV-1 is provided in GenBank Accession No. NC_002077; the complete genome of AAV-2 is provided in GenBank Accession No. NC_001401 and Srivastava et al., *J. Virol.*, 45: 555-564 {1983); the complete genome of AAV-3 is. provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_00 1862; at least portions of AAV-7 and AAV-8 genomes are provided in GenBank Accession Nos. AX753246 and AX753249, respectively; the AAV-9 genome is provided in Gao et al., J. Virol., 78: 6381-6388 (2004); the AAV-10 genome is provided in *Mol. Ther.*, 13(1): 67-76 (2006); and the AAV-11 genome is provided in *Virology*, 330(2): 375-383 (2004). The sequence of the AAV rh.74 genome is provided in see U.S. Pat. No. 9,434,928, incorporated herein by reference. Cis-acting sequences directing viral DNA replication (rep), encapsidation/packaging and host cell chromosome integration are contained within the AAV ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, *Current Topics in Microbiology and Immunology*, 158: 97-129 (1992).

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is inserted as cloned DNA in plasmids, which makes construction of recombinant genomes feasible. Furthermore, because the signals directing AAV replication and genome encapsidation are contained within the ITRs of the AAV genome, some or all of the internal approximately 4.3 kb of the genome (encoding replication and structural capsid proteins, rep-cap) may be replaced with foreign DNA. To generate AAV vectors, the rep and cap proteins may be provided in trans. Another significant feature of AAV is that it is an extremely stable and hearty virus. It easily withstands the conditions used to inactivate adenovirus (56° to 65° C. for several hours), making cold preservation of AAV less critical. AAV may even be lyophilized. Finally, AAV-infected cells are not resistant to superinfection.

There remains a need in the art for treatments for LGMD2A.

SUMMARY

Methods and products for delivering DNA encoding a protein with calpain3 (CAPN3) activity are provided herein. Such methods and products can be used to treat various diseases, for example, LGMD2A.

Recombinant adeno-associated viruses (rAAVs) are provided encoding a protein with calpain 3 (CAPN3) activity. The recombinant adeno-associated viruses comprise a polynucleotide that comprises a nucleotide sequence encoding the protein with CAPN3 activity. The nucleotide sequence encoding the protein with CAPN3 activity, for example, is at least 90% identical to SEQ ID NO: 2 or comprises the sequence of SEQ ID NO: 2.

For example, the provided rAAV comprise a polynucleotide which comprises a first AAV inverted terminal repeat (ITR), a promoter, a nucleotide sequence encoding a protein with calpain 3 (CAPN3) activity and a second AAV ITR. The nucleotide sequence encoding the protein with CAPN3 activity, for example, is at least 90% identical to SEQ ID NO: 2, or at least 91% identical to SEQ ID NO: 2, at least 92% identical to SEQ ID NO: 2, at least 93% identical to SEQ ID NO: 2, at least 94% identical to SEQ ID NO: 2, at least 95% identical to SEQ ID NO: 2, at least 96% identical to SEQ ID NO: 2, at least 97% identical to SEQ ID NO: 2, at least 98% identical to SEQ ID NO: 2, or at least 99% identical to SEQ ID NO: 2. The rAAV comprises a nucleotide sequence encoding a protein with CAPN3 activity comprises the sequence of SEQ ID NO: 2.

In addition, the provided rAAV comprises a nucleotide sequence encoding a protein with CAPN3 activity that comprises an amino acid sequence that is at least 90% identical to SEQ ID NO:7, at least 91% identical to SEQ ID NO:7, at least 92% identical to SEQ ID NO:7, at least 93% identical to SEQ ID NO:7, at least 94% identical to SEQ ID NO:7, at least 95% identical to SEQ ID NO:7, at least 96% identical to SEQ ID NO:7, at least 97% identical to SEQ ID NO:7, at least 98% identical to SEQ ID NO:7, or at least 99% identical to SEQ ID NO: 7. The rAAV comprises a nucleotide sequence encoding a protein with CAPN3 activity comprising the amino acid sequence of SEQ ID NO: 7.

The provided rAAV comprise a polynucleotide sequence which is at least 90% identical to SEQ ID NO: 1, at least 91% identical to SEQ ID NO: 1, at least 92% identical to SEQ ID NO: 1, at least 93% identical to SEQ ID NO: 1, at least 94% identical to SEQ ID NO: 1, at least 95% identical to SEQ ID NO: 1, at least 96% identical to SEQ ID NO: 1, at least 97% identical to SEQ ID NO: 1, at least 98% identical to SEQ ID NO: 1, or at least 99% identical to SEQ ID NO: 1. The rAAV comprises a polynucleotide sequence of SEQ ID NO: 1.

The nucleotide sequence, in one embodiment, is under the transcription control of a muscle-specific promoter. For example, the muscle-specific promoter comprises one or more of a human skeletal actin gene element, a cardiac actin gene element, a desmin promoter, a skeletal alpha-actin (ASKA) promoter, a troponin I (TNNI2) promoter, a myocyte-specific enhancer binding factor mef binding element, a muscle creatine kinase (MCK) promoter, a truncated MCK (tMCK) promoter, a myosin heavy chain (MHC) promoter, a hybrid a-myosin heavy chain enhancer-/MCK enhancer-promoter (MHCK7) promoter, a C5-12 promoter, a murine creatine kinase enhancer element, a skeletal fast-twitch troponin c gene element, a slow-twitch cardiac troponin c gene element, a slow-twitch troponin i gene element, hypoxia-inducible nuclear factor (HIF)-response element (HRE), a steroid-inducible element, and a glucocorticoid response element (gre). In one embodiment, the muscle-specific promoter is a tMCK promoter, which comprises a sequence of SEQ ID NO: 3.

For example, the rAAV comprises a polynucleotide which comprises, in one embodiment, a first AAV inverted terminal repeat (ITR), a tMCK promoter, the nucleotide sequence encoding the protein with calpain 3 activity, and a second AAV inverted terminal repeat (ITR). The AAV ITR (e.g., the first and/or second AAV ITRs) is, for example, an AAV2 inverted terminal repeat. The capsid proteins of the rAAV comprise, for example, an AAV rh.74 capsid protein or an AAV9 capsid protein.

The provided rAAV comprises one or more of AAV-1, AAV-2, AAV-3, AAV-4, AAV-5, AAV-6, AAV-7, AAV-8, AAV-9, AAV-10, AAV-11, AAV-12, AAV-13, AAV rh.74 and AAV rh.10 capsid proteins.

In another embodiment, compositions comprising any of the disclosed rAAV are provided. For example, the compositions are formulated for intramuscular injection or intravenous injection.

Methods of treating limb girdle muscular dystrophy 2A in a subject comprising administering to the subject a therapeutically effective amount of any of the disclosed rAAV or any composition comprising a disclosed rAAV are also provided. In any of the provided methods, the rAAV are administered by intramuscular injection or intravenous injection.

For example, in these methods treatment results in one or more of: (a) an increased muscle fiber diameter, (b) a decreased number of small lobulated muscle fibers, (c) a decreased number of fibers with internal nuclei, (d) a decreased endomysial connective tissue content, (e) correction of muscle atrophy, and (f) a increased muscle force generation. The muscle fiber affected by the treatment comprise one or more of slow twitch oxidative (STO) muscle fiber, fast twitch oxidative (FTO) muscle fiber, and fast twitch glycolytic (FTG) fiber.

In addition, in any of the provided methods, the treatment results in one or more of: (a) at least a 5%, 10%, 15%, 20%, 25%, 30%, or 35%, or 40% decrease of total muscle fiber number per mm$^2$ by 4 weeks after administration; (b) at least a 5%, 10%, 15%, 20%, or 25% increase of muscle fiber diameter by 4 weeks after administration; (c) at least a 5%, 10%, 15%, 20%, 25%, 30%, 35%, or 42% decrease of STO muscle fiber number per mm$^2$ by 4 weeks after administration; (d) at least a 5%, 10%, 15%, 20%, or 25% increase of STO muscle fiber diameter by 4 weeks after administration; (e) at least a 5%, 10%, 15%, or 20% decrease of FTO muscle fiber number per mm$^2$ by 4 weeks after administration; (f) at least a 5%, 10%, 15%, or 20% increase of FTO muscle fiber diameter by 4 weeks after administration; (g) at least a 5%, 10%, 15%, 20%, 25%, 30%, or 35% decrease of FTG muscle fiber number per mm$^2$ by 4 weeks after administration; and (h) at least a 5%, 10%, 15%, 20%, or 25% increase of FTG muscle fiber diameter by 4 weeks after administration.

In any of the provided methods, the heart muscle of the subject shows minimum or low calpain 3 protein expressed from any of the provided rAAV, or a composition comprising any of the provided rAAV. The muscle fiber affected by the treatment with the composition comprise one or more of slow twitch oxidative (STO) muscle fiber, fast twitch oxidative (FTO) muscle fiber, and fast twitch glycolytic (FTG) fiber.

Compositions for treating limb girdle muscular dystrophy 2A comprising a therapeutically effective amount of any of the disclosed rAAV or a composition comprising any of the disclosed rAAV are provided. These composition for treating treating limb girdle muscular dystrophy 2A are formulated for administration by intramuscular injection or intravenous injection. In addition, treatment with any of the disclosed compositions limb girdle muscular dystrophy 2A results in one or more of: (a) an increased muscle fiber diameter, (b) a decreased number of small lobulated muscle fibers, (c) a decreased number of fibers with internal nuclei, (d) a decreased endomysial connective tissue content, (e) correction of muscle atrophy, and (f) a increased muscle force generation. The muscle fiber affected by the treatment with the composition comprise one or more of slow twitch oxidative (STO) muscle fiber, fast twitch oxidative (FTO) muscle fiber, and fast twitch glycolytic (FTG) fiber.

In addition, the treatment with any of the disclosed compositions for treating limb girdle muscular dystrophy 2A results in one or more of: (a) at least a 5%, 10%, 15%, 20%, 25%, 30%, or 35%, or 40% decrease of total muscle fiber number per mm$^2$ by 4 weeks after administration; (b) at least a 5%, 10%, 15%, 20%, or 25% increase of muscle fiber diameter by 4 weeks after administration; (c) at least a 5%, 10%, 15%, 20%, 25%, 30%, 35%, or 42% decrease of STO muscle fiber number per mm$^2$ by 4 weeks after administration; (d) at least a 5%, 10%, 15%, 20%, or 25% increase of STO muscle fiber diameter by 4 weeks after administration; (e) at least a 5%, 10%, 15%, or 20% decrease of FTO muscle fiber number per mm$^2$ by 4 weeks after administration; (f) at least a 5%, 10%, 15%, or 20% increase of FTO muscle fiber diameter by 4 weeks after administration; (g) at least a 5%, 10%, 15%, 20%, 25%, 30%, or 35% decrease of FTG muscle fiber number per mm$^2$ by 4 weeks after administration; and (h) at least a 5%, 10%, 15%, 20%, or 25% increase of FTG muscle fiber diameter by 4 weeks after administration.

Further, treatment with any of the provided compositions for treatment of limb girdle muscular dystrophy 2A results in the heart muscle of the subject showing minimum or low calpain 3 protein expressed from any of the provided rAAV, or a composition comprising any of the provided rAAV. The heart muscle, after administration with the rAAV, shows no or little toxic effect, e.g., inflammation, necrosis and/or regeneration.

The disclosure also provides for use of a therapeutically effective amount of any of the disclosed rAAV or a composition comprising any of the disclosed rAAV for the preparation of a medicament for the treatment of limb girdle muscular dystrophy 2A. For example, the medicament is formulated for administration by intramuscular injection or intravenous injection.

In any of the uses, treatment with the medicament results in one or more of: (a) an increased muscle fiber diameter, (b) a decreased number of small lobulated muscle fibers, (c) a decreased number of fibers with internal nuclei, (d) a decreased endomysial connective tissue content, (e) correction of muscle atrophy, and (f) a increased muscle force generation. The muscle fiber affected by treatment with the medicament is one or more of slow twitch oxidative (STO) muscle fiber, fast twitch oxidative (FTO) muscle fiber, and fast twitch glycolytic (FTG) fiber.

In addition, in any of the uses of a therapeutically effective amount of any of the disclosed rAAV or a composition provided, treatment with the medicament results in one or more of: (a) at least a 5%, 10%, 15%, 20%, 25%, 30%, or 35%, or 40% decrease of total muscle fiber number per mm$^2$ by 4 weeks after administration; (b) at least a 5%, 10%, 15%, 20%, or 25% increase of muscle fiber diameter by 4 weeks after administration; (c) at least a 5%, 10%, 15%, 20%, 25%, 30%, 35%, or 42% decrease of STO muscle fiber number per mm$^2$ by 4 weeks after administration; (d) at least a 5%, 10%, 15%, 20%, or 25% increase of STO muscle fiber diameter by 4 weeks after administration; (e) at least a 5%, 10%, 15%, or 20% decrease of FTO muscle fiber number per mm$^2$ by 4 weeks after administration; (f) at least a 5%, 10%, 15%, or 20% increase of FTO muscle fiber diameter by 4 weeks after administration; (g) at least a 5%, 10%, 15%, 20%, 25%, 30%, or 35% decrease of FTG muscle fiber number per mm$^2$ by 4 weeks after administration; and (h) at least a 5%, 10%, 15%, 20%, or 25% increase of FTG muscle fiber diameter by 4 weeks after administration.

The any of the uses of a therapeutically effective amount of any of the disclosed rAAV or a composition provided, after treatment with the medicament, the heart muscle of the subject shows no, minimum or low calpain 3 protein expressed from the disclosed or disclosed composition.

BRIEF DESCRIPTION OF THE DRAWINGS

In FIG. 1D, lobulated fibers with a pattern of subsarcolemmal organelle, mitochondria distribution (arrows) suggest partial myotube fusion in the untreated CAPN3-KO muscle at higher magnification. Scale bar=20 μm for B-D. In FIG. 1E, the muscle fiber size distribution histograms (mean±SEM/mm² area; derived from 3 mice in each group) of the treated and untreated TA muscle from CAPN3-KO mice show a shift to larger diameter fibers with the treatment and an increase in the small diameter subpopulation present in the untreated group. In FIG. 1F, the Slow twiTch Oxidative (STO) fiber size distribution histograms show a larger number of small fibers (e.g., fiber diameters equal to or less than 30 μm) in the untreated CAPN3-KO muscle as compared to treated CAPN3-KO muscle.

FIG. 8 provides the data for the run-to-exhaustion test.

DETAILED DESCRIPTION

Figure 1:
FIGS. 1A-1F show that gene therapy restored impaired regeneration in CAPN3-KO muscle. Schematic diagram of single-stranded AAV9.CAPN3 rAAV is shown in FIG. 1A. In between the 5' and 3' single strand ITRs (inverted terminal repeats), the muscle creatine kinase (MCK) promoter (563 bp) drives the expression of CAPN3 open reading frame (2466 bp). Also labeled is polyadenylation site (Poly A, 53 bp). Tibialis anterior (TA) muscles from CAPN3-KO mice were first injected with CTX, and 2 weeks later with $1 \times 10^{11}$ vg of AAV.CAPN3 to left TA (FIG. 1B) or PBS to right TA (FIG. 1C). Four weeks after rAAV injection, the muscle diameter increased and the lobulated fibers were less common compared to the untreated CAPN3-KO muscle.
Figure 1:
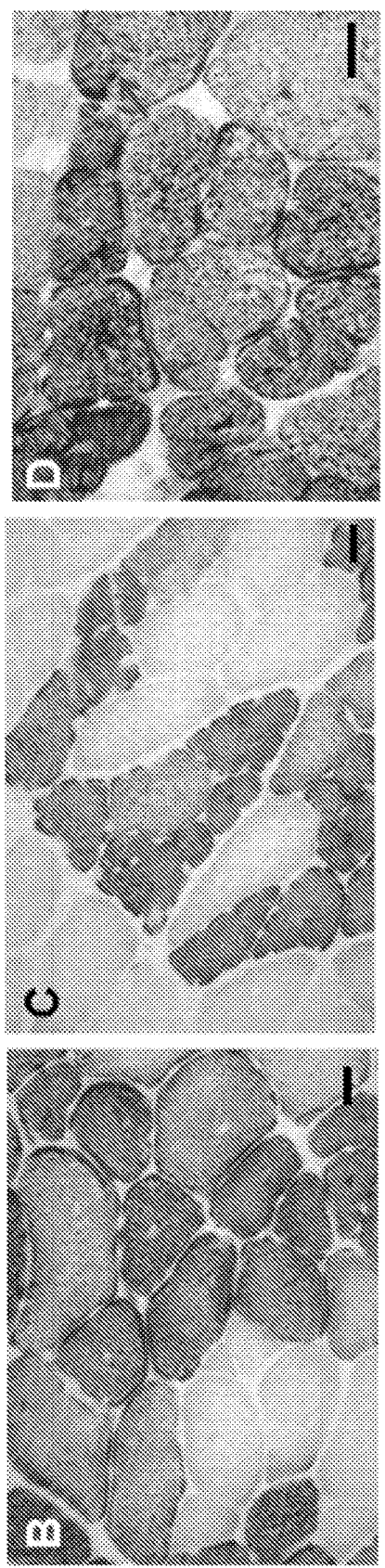
Figure 1:
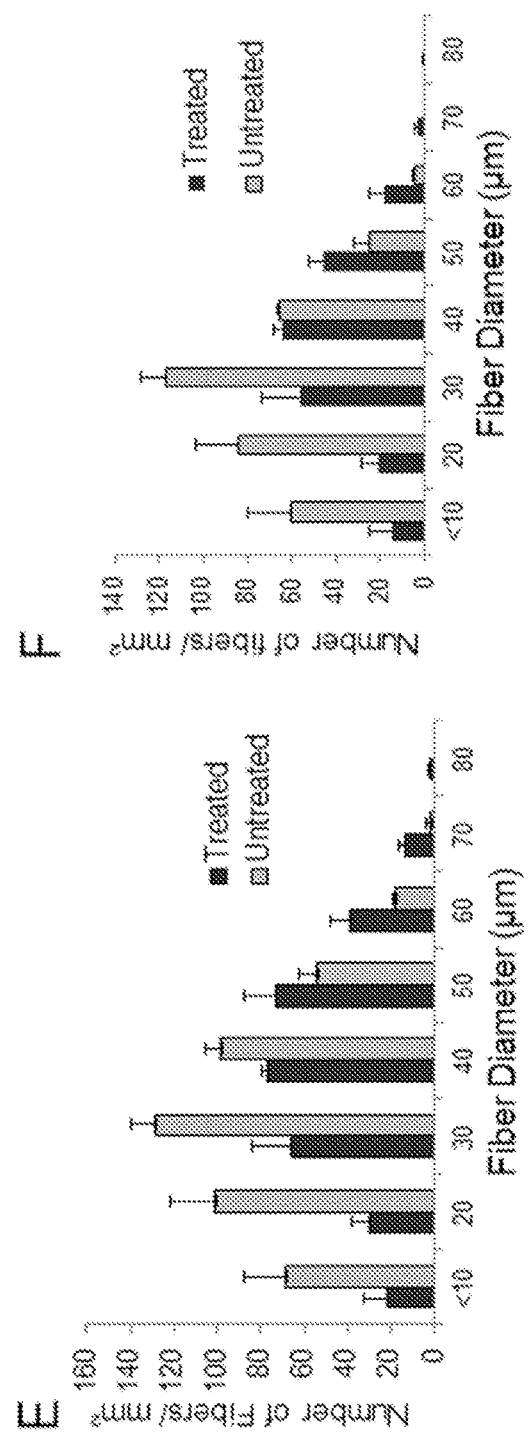

Recombinant AAVs (rAAVs) provided herein comprise a polynucleotide that comprises a first AAV inverted terminal repeat (ITR), a promoter, a nucleotide sequence encoding a protein with calpain 3 (CAPN3) activity and a second AAV ITR. In one embodiment, the nucleotide encodes CAPN3. Embodiments include, but are not limited to, an rAAV comprising a nucleotide sequence encoding CAPN3 or a protein with CAPN3 activity, wherein the nucleotide sequence is at least 65%, at least 70%, at least 75%, at least 80%, 81%, 82%, 83%, 84%, 85%, 86%, 87%, 88%, or 89% identical to the nucleotide sequence of SEQ ID NO: 2. Additional embodiments include, but are also not limited to, rAAV comprising a nucleotide sequence at least 90%, 91%, 92%, 93%, 94%, 95%, 96%, 97%, 98%, 99% identical to the nucleotide sequence set forth in SEQ ID NO: 2 and encodes a polypeptide with a CAPN3 proteolytic activity. The CAPN3 proteolytic activity is understood in the art as the activity of proteolyzing potential substrates such as fodrin and HSP60, and/or to the activity of autolytically self-cleaving. Thus, as used herein, the term "a protein with calpain 3 (CAPN3) activity" refers to a protein with CAPN3 proteolytic activity, which includes but is not limited to the activity of proteolyzing substrates such as fodrin and HSP60, and/or to the activity of autolytically self-cleaving. The protein with CAPN3 activity can have the full or partial activity of a full length calpain 3 protein. In one embodiment, the protein with CAPN3 activity has at least 60%, 70%, 80%, 90%, 95%, or 99% of activity of a full length CAPN3 protein. In another embodiment, the protein with CAPN3 activity comprises an amino acid sequence with at least 90%, 91%, 92%, 93%, 94%, 95%, 96%, 97%, 98%, or 99% identical to SEQ ID NO: 7.

In some embodiments, the nucleotide sequence encoding the protein with CAPN3 activity comprises a sequence of SEQ ID NO: 2. In another embodiment, the protein with CAPN3 activity comprises an amino acid sequence with at least 90%, 91%, 92%, 93%, 94%, 95%, 96%, 97%, 98%, or 99% identical to SEQ ID NO: 7. In another embodiment, the protein with CAPN3 activity comprises the amino acid sequence of SEQ ID NO: 7. In another embodiment, the polynucleotide of the rAAV comprises a sequence which is at least 90%, 91%, 92%, 93%, 94%, 95%, 96%, 97%, 98%, or 99% identical to SEQ ID NO: 1. In another embodiment, the polynucleotide comprises a sequence at least 95% identical to SEQ ID NO: 1. In one embodiment, the polynucleotide comprises the sequence of SEQ ID NO: 1.

In another aspect, described herein is a recombinant AAV comprising a nucleotide sequence that encodes a protein with CAPN3 activity and/or that comprises a nucleotide sequence that hybridizes under stringent conditions to the nucleic acid sequence of SEQ ID NO: 2, or the complement thereof. The term "stringent" is used to refer to conditions that are commonly understood in the art as stringent. Hybridization stringency is principally determined by temperature, ionic strength, and the concentration of denaturing agents such as formamide. Examples of stringent conditions for hybridization and washing are 0.015 M sodium chloride, 0.0015 M sodium citrate at 65-68° C. or 0.015 M sodium chloride, 0.0015M sodium citrate, and 50% formamide at 42° C. See Sambrook et al., Molecular Cloning: A Laboratory Manual, 2nd Ed., Cold Spring Harbor Laboratory, (Cold Spring Harbor, N.Y. 1989).

In recombinant genomes described herein, the CAPN3 polynucleotide is operatively linked to transcriptional control elements (including, but not limited to, promoters, enhancers and/or introns), specifically transcriptional control elements functional in target cells of interest. For example, various embodiment provide methods of transducing muscle cells using muscle-specific transcriptional control elements, including, but not limited to, those derived from the actin and myosin gene families, such as from the myoD gene family [See Weintraub et al., Science, 251: 761-766 (1991)], the myocyte-specific enhancer binding factor MEF-2 [Cserjesi and Olson, Mol Cell Biol, 11: 4854-4862 (1991)], control elements derived from the human skeletal actin gene [Muscat et al., Mol Cell Biol, 7: 4089-4099 (1987)], muscle creatine kinase sequence elements [See Johnson et al., Mol Cell Biol, 9:3393-3399 (1989)] and the murine creatine kinase enhancer (mCK) element, control elements derived from the skeletal fast-twitch troponin C gene, the slow-twitch cardiac troponin C gene and the slow-twitch troponin I gene: hypozia-inducible nuclear factors [Semenza et al., Proc Natl Acad Sci USA, 88: 5680-5684 (1991)], steroid-inducible elements and promoters including the glucocorticoid response element (GRE) [See Mader and White, Proc. Natl. Acad. Sci. USA, 90: 5603-5607 (1993)], the tMCK promoter [see Wang et al., Gene Therapy, 15: 1489-1499 (2008)], the CK6 promoter [see Wang et al., supra] and other control elements. In one embodiment, the nucleotide sequence encoding a protein with calpain 3 (CAPN3) activity is operably linked to a muscle-specific promoter. In one embodiment, the muscle-specific promoter comprises one or more of a human skeletal actin gene element, a cardiac actin gene element, a desmin promoter, a skeletal alpha-actin (ASKA) promoter, a troponin I (TNNI2) promoter, a myocyte-specific enhancer binding factor mef binding element, a muscle creatine kinase (MCK) promoter, a truncated MCK (tMCK) promoter, a myosin heavy chain (MHC) promoter, a hybrid a-myosin heavy chain enhancer-/MCK enhancer-promoter (MHCK7) promoter, a C5-12 promoter, a murine creatine kinase enhancer element, a skeletal fast-twitch troponin c gene element, a slow-twitch cardiac troponin c gene element, a slow-twitch troponin i gene element, hypoxia-inducible nuclear factor (HIF)-response element (HRE), a steroid-inducible element, a glucocorticoid response element (gre). In another embodiment, the muscle-specific promoter is an MCK promoter, a tMCK promoter, or an MHCK7 promoter. In some embodiments, the muscle-specific promoter is tMCK that comprises a nucleotide sequence of SEQ ID NO: 3.

Previous studies showed that expression of CAPN3 driven by desmin promoter resulted in cardiotoxicity. In follow up studies, selective skeletal muscle expression of the gene eliminated the cardiac defects. The AAV genomes disclosed herein comprise a muscle specific promoter, tMCK to restrict CAPN3 expression to the skeletal muscle and showed no cardiac toxicity following systemic delivery of the virus at 6E12 vg (twice the proposed initial high dose) 4 weeks after gene injection.

The rAAV genomes described herein lack AAV rep and cap DNA. rAAV genomes provided comprise a CAPN3 polynucleotide as described above and one or more AAV ITRs flanking the polynucleotide. AAV DNA in the rAAV genomes may be from any AAV serotype for which a recombinant virus can be derived including, but not limited to, AAV serotypes AAV-1, AAV-2, AAV-3, AAV-4, AAV-5, AAV-6, AAV-7, AAV-8, AAV-9, AAV-10, AAV-11, AAV-12, AAV-13, AAV rh.74 and AAV rh.10. Other types of rAAV variants, for example rAAV with capsid mutations, are also contemplated. See, for example, Marsic et al., Molecular Therapy, 22(11): 1900-1909 (2014). As noted in the Background section above, the nucleotide sequences of the genomes of various AAV serotypes are known in the art. To promote skeletal muscle specific expression, AAV1, AAV5, AAV6, AAV8 or AAV9 may be used.

DNA plasmids provided comprise rAAV genomes. The DNA plasmids are transferred to cells permissible for infection with a helper virus of AAV (including, but not limited to, adenovirus, E1-deleted adenovirus or herpesvirus) for assembly of the rAAV genome into infectious viral particles. Techniques to produce rAAV particles, in which an AAV genome to be packaged, rep and cap genes, and helper virus functions are provided to a cell are standard in the art. Production of rAAV requires that the following components are present within a single cell (denoted herein as a packaging cell): a rAAV genome, AAV rep and cap genes separate from (i.e., not in) the rAAV genome, and helper virus functions. The AAV ITRs and rep and cap genes may be from any AAV serotype for which recombinant virus can be derived and may be from a different AAV serotype than the rAAV genome ITRs, including, but not limited to, AAV serotypes AAV-1, AAV-2, AAV-3, AAV-4, AAV-5, AAV-6, AAV-7, AAV-8, AAV-9, AAV-10, AAV-11, AAV-12, AAV-13, AAV rh. 10 and AAV rh.74. Production of pseudotyped rAAV is disclosed in, for example, WO 01/83692 which is incorporated by reference herein in its entirety. Thus, in one embodiment, the rAAV comprises one or more of AAV-1, AAV-2, AAV-3, AAV-4, AAV-5, AAV-6, AAV-7, AAV-8, AAV-9, AAV-10, AAV-11, AAV-12, AAV-13, AAV rh.74 or AAV rh. 10 capsid proteins. In another embodiment, the rAAV comprises an AAV rh.74 capsid protein or an AAV9 capsid protein.

A method of generating a packaging cell is to create a cell line that stably expresses all the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing [Samulski et al., Proc. Natl. Acad. S6. USA, 79:2077-2081 (1982)], addition of synthetic linkers containing restriction endonuclease cleavage sites [Laughlin et al., Gene, 23:65-73 (1983)] or by direct, blunt-end ligation [Senapathy & Carter, J. Biol. Chem., 259:4661-4666 (1984)]. The packaging cell line is then infected with a helper virus such as adenovirus. The advantages of this method are that the cells are selectable and are suitable for large-scale production of rAAV. Other examples of suitable methods employ adenovirus or baculovirus rather than plasmids to introduce rAAV genomes and/or rep and cap genes into packaging cells.

General principles of rAAV production are reviewed in, for example, Carter, Current Opinions in Biotechnology, 1533-1539 (1992); and Muzyczka, Curr. Topics in Microbial. and Immunol., 158:97-129 (1992). Various approaches are described in Ratschin et al., Mol. Cell. Biol., 4:2072 (1984); Hermonat et al., Proc. Natl. Acad. Sci. USA, 81:6466 (1984); Tratschin et al., Mol. Cell. Biol., 5:3251 (1985); McLaughlin et al., J. Virol., 62:1963 (1988); Lebkowski et al., Mol. Cell. Biol., 7:349 (1988); Samulski et al., J. Virol., 63:3822-3828 (1989); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al., Vaccine, 13:1244-1250 (1995); Paul et al., Human Gene Therapy, 4:609-615 (1993); Clark et al., Gene Therapy 3:1124-1132 (1996); U.S. Pat. Nos. 5,786,211; 5,871,982; 6,258,595; and McCarty, Mol. Ther., 16(10): 1648-1656 (2008). The foregoing documents are hereby incorporated by reference in their entirety herein, with particular emphasis on those sections of the documents relating to rAAV production.

Thus packaging cells are provided that produce infectious rAAV. In one embodiment, packaging cells may be stably transformed cancer cells such as HeLa cells, and PerC.6 cells (a cognate 293 line). In another embodiment, packaging cells are cells that are not transformed cancer cells, such as low passage 293 cells (human fetal kidney cells transformed with E1 of adenovirus), MRC-5 cells (human fetal fibroblasts), WI-38 cells (human fetal fibroblasts), Vero cells (monkey kidney cells) and FRhL-2 cells (rhesus fetal lung cells).

Recombinant AAV provided herein are thus replication-deficient, infectious, encapsidated viral particles which comprise a recombinant genome. Examples include, but are not limited to, a rAAV including a genome comprising the sequence set out in SEQ ID NO: 1 encoding CAPN3, a rAAV including a genome consisting essentially of the sequence set out in SEQ ID NO: 1 encoding CAPN3, and a rAAV (named "AAVrh.74.tMCK.CAPN3") including a genome consisting of the sequence set out in SEQ ID NO: 1 encoding CAPN3. The genomes of the rAAV lack AAV rep and cap DNA, that is, there is no AAV rep or cap DNA between the ITRs of the rAAV genome.

The sequence of the AAVrh.74.tMCK.CAPN3 sequence is set out in SEQ ID NO: 1, in which an AAV2 ITR spans nucleotides 1-128, the tMCK promoter spans nucleotides 165-884, a chimeric intron spans nucleotides 937-1069, a Kozak Sequence spans nucleotides 1101-1106, the CAPN3 polynucleotide spans nucleotides 1107-3572, a poly A signal spans nucleotides 3581-3780, and a second AAV2 ITR spans nucleotides 3850-3977.

The rAAV may be purified by methods known in the art such as by column chromatography or cesium chloride gradients. Methods for purifying rAAV vectors from helper virus are known in the art and include methods disclosed in, for example, Clark et al., Hum. Gene Ther., 10(6): 1031-1039 (1999); Schenpp and Clark, Methods Mol. Med., 69: 427-443 (2002); U.S. Pat. No. 6,566,118; and WO 98/09657.

In another embodiment, compositions comprising rAAV described herein are provided. Compositions provided comprise rAAV in a pharmaceutically acceptable carrier. The compositions may also comprise other ingredients such as diluents and adjuvants. Acceptable carriers, diluents and adjuvants are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics or polyethylene glycol (PEG).

Titers of rAAV to be administered in methods described herein can vary depending, for example, on the particular rAAV, the mode of administration, the treatment goal, the individual, and the cell type(s) being targeted, and may be determined by methods standard in the art. Titers of rAAV may range from about $1\times10^{10}$, about $1\times10^{11}$, about $1\times10^{12}$, about $1\times10^{13}$, to about $1\times10^{14}$, or more DNase resistant particles (DRPs) per ml. Dosages may also be expressed in units of viral genomes (vg). Exemplary disclosed doses include 1E11 vg, 3E12 vg and 6E12 vg.

Methods of transducing a target cell such as a muscle cell with rAAV, in vivo or in vitro, are contemplated herein. The in vivo methods comprise the step of administering an effective dose, or effective multiple doses, of a composition comprising a rAAV provided herein to subject (e.g., an animal including but not limited to a human patient) in need thereof. If the dose is administered prior to development of a disorder/disease, the administration is prophylactic. If the dose is administered after the development of a disorder/disease, the administration is therapeutic. An effective dose is a dose that alleviates (eliminates or reduces) at least one symptom associated with the disorder/disease state being treated, that slows or prevents progression to a disorder/disease state, that slows or prevents progression of a disorder/disease state, that diminishes the extent of disease, that results in remission (partial or total) of disease, and/or that prolongs survival. In comparison to the subject before treatment, methods herein result in one or more of: an increased muscle fiber diameter, a decreased number of small lobulated muscle fibers, a decreased number of fibers with internal nuclei, a decreased endomysial connective tissue content, correction of muscle atrophy, and an increased muscle force generation. In one embodiment, the muscle fiber comprises one or more of slow twitch oxidative (STO) muscle fiber, fast twitch oxidative (FTO) muscle fiber, and fast twitch glycolytic (FTG) fiber. In one embodiment, the treatment results in one or more of (a) at least a 5%, 10%, 15%, 20%, 25%, 30%, or 35%, or 40% decrease of total muscle fiber number per $mm^2$ by 4 weeks after administration; (b) at least a 5%, 10%, 15%, 20%, or 25% increase of muscle fiber diameter by 4 weeks after administration; (c) at least a 5%, 10%, 15%, 20%, 25%, 30%, 35%, or 42% decrease of STO muscle fiber number per $mm^2$ by 4 weeks after administration; (d) at least a 5%, 10%, 15%, 20%, or 25% increase of STO muscle fiber diameter by 4 weeks after administration; (e) at least a 5%, 10%, 15%, or 20% decrease of FTO muscle fiber number per $mm^2$ by 4 weeks after administration; (f) at least a 5%, 10%, 15%, or 20% increase of FTO muscle fiber diameter by 4 weeks after administration; (g) at least a 5%, 10%, 15%, 20%, 25%, 30%, or 35% decrease of FTG muscle fiber number per $mm^2$ by 4 weeks after administration; and (h) at least a 5%, 10%, 15%, 20%, or 25% increase of FTG muscle fiber diameter by 4 weeks after administration. The method of this disclosure, in one embodiment, leads to no, minimum or low calpain 3 protein expressed from the rAAV in the heart muscle of the subject administered with the rAAV.

Assays to examine these results are understood in the art and/or are described in the examples herein. Use of the methods described herein to prevent or treat disorders/diseases (e.g., muscular dystrophies) caused by defects in CAPN3 activity or defects in expression of CAPN3 is contemplated. LGMD2A is an example of a disease contemplated for prevention or treatment according to the methods.

Combination therapies are also contemplated. Combination as used herein includes both simultaneous treatment or sequential treatments. Combinations of methods described herein with standard medical treatments (e.g., corticosteroids) are specifically contemplated, as are combinations with novel therapies.

Administration of an effective dose of the compositions may be by routes standard in the art including, but not limited to, intramuscular, parenteral, intravenous, intrathecal, oral, buccal, nasal, pulmonary, intracranial, intraosseous, intraocular, rectal, or vaginal. Route(s) of administration and serotype(s) of AAV components of the rAAV (in particular, the AAV ITRs and capsid protein) may be chosen and/or matched by those skilled in the art taking into account the infection and/or disease state being treated and the target cells/tissue(s) that are to express the CAPN3. In one embodiment, the rAAV is administered by intramuscular injection, intravenous injection, intraperitoneal injection, subcutaneous injection, epicutaneous administration, intravaginal injection, intradermal administration, or nasal administration. In another embodiment, the rAAV is administered by intramuscular injection or intravenous injection.

In particular, actual administration of rAAV described herein may be accomplished by using any physical method that will transport the rAAV recombinant vector into the target tissue of an animal. Administration includes, but is not limited to, injection into muscle, the bloodstream, and/or directly into the liver. Simply resuspending a rAAV in phosphate buffered saline has been demonstrated to be sufficient to provide a vehicle useful for muscle tissue expression, and there are no known restrictions on the carriers or other components that can be co-administered with the rAAV. Capsid proteins of a rAAV may be modified so that the rAAV is targeted to a particular target tissue of interest such as muscle. See, for example, WO 02/053703, the disclosure of which is incorporated by reference herein. Pharmaceutical compositions can be prepared as injectable formulations or as topical formulations to be delivered to the muscles by transdermal transport. Numerous formulations for both intramuscular injection and transdermal transport have been previously developed and can be used in the practice of the methods. The rAAV can be used with any pharmaceutically acceptable carrier for ease of administration and handling.

For purposes of intramuscular injection, solutions in an adjuvant such as sesame or peanut oil or in aqueous propylene glycol can be employed, as well as sterile aqueous solutions. Such aqueous solutions can be buffered, if desired, and the liquid diluent first rendered isotonic with saline or glucose. Solutions of rAAV as a free acid (DNA contains acidic phosphate groups) or a pharmacologically acceptable salt can be prepared in water suitably mixed with a surfactant such as hydroxypropylcellulose. A dispersion of rAAV can also be prepared in glycerol, liquid polyethylene glycols and mixtures thereof and in oils. Under ordinary conditions of storage and use, these preparations contain a preservative to prevent the growth of microorganisms. In this connection, the sterile aqueous media employed are all readily obtainable by standard techniques well-known to those skilled in the art.

The pharmaceutical forms suitable for systemic (e.g., intravenous) injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating actions of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating rAAV in the required amount in the appropriate solvent with various other ingredients enumerated above, as required, followed by filter sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the methods of preparation, in some embodiments, comprises vacuum drying and/or the freeze drying technique, each of which can yield a powder of the active ingredient plus any additional desired ingredient from the previously sterile-filtered solution thereof.

Transduction with rAAV may also be carried out in vitro. In one embodiment, desired target muscle cells are removed from the subject, transduced with rAAV and reintroduced into the subject. Alternatively, syngeneic or xenogeneic muscle cells can be used where those cells will not generate an inappropriate immune response in the subject.

Suitable methods for the transduction and reintroduction of transduced cells into a subject are known in the art. In one embodiment, cells can be transduced in vitro by combining rAAV with muscle cells, e.g., in appropriate media, and screening for those cells harboring the DNA of interest using conventional techniques such as Southern blots and/or PCR, or by using selectable markers. Transduced cells can then be formulated into pharmaceutical compositions, and the composition introduced into the subject by various techniques, such as by intramuscular, intravenous, subcutaneous and intraperitoneal injection, or by injection into smooth and cardiac muscle, using e.g., a catheter.

Transduction of cells with rAAV by methods described herein results in sustained expression of CAPN3 or a protein with CAPN3 activity. Methods are thus provided for administering rAAV which expresses CAPN3 or a protein with CAPN3 activity to a subject, preferably a human being. The subject of this disclosure includes but is not limited to human, a dog, a cat, a horse, a cow, a pig, a sheep, a goat, a chicken, a rodent (e.g., rats and mice), and a primate. These methods include transducing tissues (including, but not limited to, tissues such as muscle, organs such as liver and brain, and glands such as salivary glands) with one or more rAAV described herein.

Muscle tissue is an attractive target for in vivo DNA delivery, because it is not a vital organ and is easy to access. The methods herein provide sustained expression of CAPN3 from transduced muscle cells.

By "muscle cell," "muscle fiber," or "muscle tissue" is meant a cell or group of cells derived from muscle of any kind [for example, skeletal muscle and smooth muscle (e.g., from the digestive tract, urinary bladder, blood vessels or cardiac tissue)]. Such muscle cells may be differentiated or undifferentiated, such as myoblasts, myocytes, myotubes, cardiomyocytes and cardiomyoblasts.

The term "transduction" is used to refer to the administration/delivery of CAPN3 to a recipient cell either in vivo or in vitro, via a rAAV described resulting in expression of CAPN3 by the recipient cell.

Thus, methods are provided of administering an effective dose (or doses, administered essentially simultaneously or doses given at intervals) of rAAV that encode CAPN3 to a subject in need thereof.

As noted above, the methods described herein result in the subject, in comparison to the subject before treatment, one or more of: increased muscle fiber diameter, decreased number of small lobulated slow twitch oxidative (STO) muscle fibers, decreased number of fibers with internal nuclei, decreased endomysial connective tissue content, correction of muscle atrophy, and increased muscle force generation.

EXAMPLES

Aspects and embodiments are illustrated by the following examples. Example 1 describes production of AAV9.MCK.CAPN3. Example 2 describes intramuscular administration of AAV9.MCK.CAPN3. Example 3 describes production of AAVrh.74.tMCK.CAPN3. Example 4 describes intramuscular administration of AAVrh.74.tMCK.CAPN3. Example 5 describes intravenous administration of AAVrh.74.tMCK.CAPN3. Example 6 describes end point studies. Example 7 describes toxicology and biodistribution studies. Example 8 describes in vivo biopotency testing following intramuscular injection. Example 9 describes in vivo biopotency testing following systemic injection. Example 10 describes assessment of systemic AAVrh.74.tMCK.CAPN3 gene delivery. Example 11 describes assessment of cardiac toxicity following systemic injection of AAVrh.74.tMCK.CAPN3 vector. Example 12 describes in vivo physiological analysis.

Example 1

Production of AAV9.MCK.CAPN3

An AAV vector (named AAV.CAPN3) carrying the CAPN3 gene under the muscle specific MCK promoter (FIG. 1A) was produced. A DNA including the open reading frame of mouse CAPN3 (NM_007601.3) between two Not1 restriction sites was synthesized by Eurofin Genomics, USA, and then subcloned into a single strand AAV.MCK (muscle creatine kinase) vector previously described in Rodino-Klapac et al., *Journal of Translational Medicine*, 5:45-55 (2007)]. rAAV vectors were produced by a modified cross-packaging approach whereby the AAV type 2 vector genome can be packaged into multiple AAV capsid serotypes. [Rabinowitz et al., *J Virol.* 76 (2):791-801 (2002)]. Production was accomplished using a standard three-plasmid DNA/CaPO4 precipitation method using HEK293 cells. 293 cells were maintained in DMEM supplemented with 10% fetal bovine serum (FBS) and penicillin and streptomycin. The production plasmids were: (i) pAAV.MCK.microdys, (ii) rep2-capX modified AAV helper plasmids encoding cap serotypes 1, 6, or an 8-like isolate, and (iii) an adenovirus type 5 helper plasmid (pAdhelper) expressing adenovirus E2A, E4 ORF6, and VA I/II RNA genes. To allow comparisons between serotypes, a quantitative PCR-based titration method was used to determine an encapsidated vector genome (vg) titer utilizing a Prism 7500 Taqman detector system (PE Applied Biosystems). [Clark et al., *Hum Gene Ther.* 10 (6): 1031-1039 (1999)] The primer and fluorescent probe targeted the MCK promoter and were as follows: MCK forward primer, 5-CCCGAGATGCCTGGT-TATAATT-3 (SEQ ID NO: 4); MCK reverse primer, 5-GCTCAGGCAGCAGGTGTTG-3 (SEQ ID NO: 5); and MCK probe, 5-FAM-CCAGACATGTGGCTGCTCCCCC-TAMRA-3 (SEQ ID NO: 6). The final titer (vg ml-1) was determined by quantitative reverse transcriptase PCR using the specific primers and probes for MCK promoter utilizing a Prism 7500 Real-time detector system (PE Applied Biosystems, Grand Island, NY, USA). Aliquoted viruses were kept at −80° C. until use.

Example 2

Intramuscular Administration of AAV9.MCK.CAPN3

To demonstrate if WT CAPN3 can restore the impaired regeneration process in CAPN3 knockout (CAPN3-KO) mice, TA muscles from CAPN3-KO mice (n=4) [Kramerova et al., *Hum Mol Genet* 13(13):1373-1388 (2004)]] under anesthesia were first injected with 30 μl CTX, and 2 weeks later were transduced to express wild type CAPN3 using AAV9.MCK.CAPN3 at $1\times10^{11}$ vg in 20 μl volume via intramuscular injection. TA muscles from another cohort of CAPN3-KO (n=4), served as controls received the same volume of PBS 2 weeks post-CTX injection.

Mice were killed at 6 weeks post-CTX injection, and TA muscles were removed and processed for cryostat sectioning. Twelve μm thick cross sections were first stained with H&E for routine histopathological evaluation; muscle fiber type specific diameter measurements were obtained from SDH stained cross sections of the TA from 3 mice in each group. Three random images of the TA (per section per animal) was photographed at X20 magnification and the fiber diameter measurements and fiber type specific histograms were generated.

Succinic dehydrogenase (SDH) enzyme histochemistry was used to assess metabolic fiber type differentiation [slow twitch oxidative (STO), fast twitch oxidative (FTO) and fast twitch glycolytic (FTG)]. Muscle fiber type specific diameter measurements were obtained using 12 μm thick-SDH stained cross sections at 4 and 12 weeks after final cardiotoxin injection. Three images, each representing three distinct zones of the gastrocnemius muscle (a deep zone predominantly composed of STO, intermediate zone showing a checkerboard appearance of STO and FTO or FTG and the superficial zone predominantly composed of FTG fibers) along the midline axis (per section per animal) was photographed at X20 magnification using an Olympus BX41 microscope and SPOT camera (Olympus BX61, Japan). This approach was chosen to capture the alterations in the oxidative state of fibers in each zone in response to metabolic changes during regeneration. Diameters of dark (STO), intermediate (FTO) and light (FTG) fibers were determined by measuring the shortest distance across the muscle fiber using Zeiss Axiovision LE4 software (v.4.8). The fiber diameter histograms were generated separately for STO; FTG and FTO were combined to represent the total fast twitch fiber population (FTG/O), derived from 3 animals and expressed as number per $mm^2$ of endomysial area (mean±SEM). The mean fiber diameter was derived from combining all 3 fiber types. An average of 900-1700 fibers were measured per group. TA muscles were used for assessment of fibrosis (see below)

Four weeks after AAV9.MCK.CAPN3 injection, a significant increase in muscle diameter with an apparent decrease of internal nuclei and far less number of small fibers with lobulated pattern was observed (FIG. 1B). The untreated CAPN3-KO muscle had 31.6% more fibers per mm$^2$ area, mostly composed of small and lobulated STO fibers indicating that the treatment improved myotube fusion, therefore decreased individual small fiber number per unit area (FIGS. 1, C and D; Table 1).

TABLE 1

Tibialis anterior muscle fiber size

|  | Untreated Number per mm$^2$ | Untreated Diameter | AAV.CAPN3-treated Number per mm$^2$ | AAV.CAPN3-treated Diameter |
|---|---|---|---|---|
| STO | 355 | 32.72 ± 0.4 | 233 | 39.81 ± 0.6* |
| FTG/O | 116 | 44.26 ± 0.9 | 99 | 50.40 ± 1.2* |
| All fibers | 471 | 35.55 ± 0.4 | 322 | 43.08 ± 0.6* |

*p < 0.0001 compared to same wild type parameter

The fiber size distribution histograms of the treated TA muscle showed a shift to larger diameter fibers with treatment and the excessive number of small fibers in the untreated CAPN3-KO control muscle are of STO histochemical fiber type (FIGS. 1E and 1F). Collectively, these findings show that CAPN3 replacement via gene therapy in the CAPN3-KO muscle rescued defective regeneration, evidenced by toward normalization of fiber size and a decrease in the number of STO fiber population.

Example 3

Production of AAVrh.74.tMCK.CAPN3

Figure 2:
FIG. 2 shows a schematic diagram of the rAAV of this disclosure, named as "AAVrh.74.tMCK.CAPN3."

An AAV vector (named AAVrh74.tMCK.CAPN3) carrying the CAPN3 gene under a truncated muscle specific MCK promoter (tMCK promoter) was produced. A DNA including the open reading frame of mouse CAPN3 (NM_007601.3) between two Not1 restriction sites was synthesized by Eurofin Genomics, USA, and then inserted in an AAV production plasmid. A map of the plasmid is shown in FIG. 2.

rAAV vectors were then produced by the approach described in Example 1.

Example 4

Intravenous Administration of AAVrh.74.tMCK.CAPN3

CAPN3-KO mice, 6 months of age, received AAVrh.74.tMCK.CAPN3 at low ($3 \times 10^{12}$ vg) and high doses ($6 \times 10^{12}$ vg) via injection into tail vein. The mice were killed at 20 weeks post gene injection for endpoint studies. Age matched vehicle treated CAPN3-KO mice served as controls.

TABLE 2

Treatment cohorts

| Cohorts | Treatment | Total # of mice | Age at start of treatment | Treatment Dose (AAVrh.74.tMCK.CAPN3) | Treatment Duration | Age at End Point |
|---|---|---|---|---|---|---|
| CAPN3-KO |  | 40 |  |  |  |  |
| Low dose | AAV.CAPN3 | 8 | 24 wks | 3e12 vg in 300 µl saline, i.v. | 20 wks | 44 wks |
|  | Saline treatment | 8 | 24 wks |  | 20 wks | 44 wks |
| High Dose | AAV.CAPN3 | 8 | 24 wks | 6e12 vg in 300 µl saline, i.v. | 20 wks | 44 wks |
|  | Saline treatment | 8 | 24 wks |  | 20 wks | 44 wks |
| Wild type Controls | Saline treatment | 8 | 24 wks |  | 20 wks | 44 wks |

End point studies performed as described in Example 7 below include muscle physiology (TA force generation or in vivo muscle contractibility assay, and protection from eccentric contractions), muscle histopathology, hCAPN3 detection using qPCR, and Western blot analysis.

Example 5

Intramuscular Administration of AAVrh.74.tMCK.CAPN3

Regenerative responses are measured in old and young CAPN3-KO muscle to cardiotoxin (CTX)-induced synchronized necrosis following the introduction of CAPN3 into regenerating muscle via rAAV treatment.

In cohorts of young (at 2 months of age) and old mice (at 6 months of age), CTX is injected into both TA muscles to induce synchronized necrosis 2 weeks prior to rAAV injection to the left TA muscle. AAVrh.74.tMCK.CAPN3 at $1 \times 10^{11}$ vg in 20 µl volume is administered via intramuscular injection. Endpoint studies are performed at 8 weeks post gene transfer (at $1 \times 10^{11}$ vg dose with efficacy established in our previous studies) to assess the correction of regeneration defect by comparing quantitative histology and physiological outcomes from the left TA to untreated right TA.

euthanized, and the TA muscle is dissected out, weighed and frozen for analysis. Analysis of the data is performed blindly but not randomly.

In Vivo Muscle Contractibility Assay

This assay measures the aggregate torque produced by either the plantar or dorsiflexor muscles of the lower limb

TABLE 3

Treatment cohorts

| Cohorts | Treatment | Total # of mice | CTX inj-bilateral TA muscle; age/delivery route/dose | Age at start of gene therapy | Treatment Dose (AAVrh.74.tMCK.CAPN3) Left TA | Treatment Duration | Age at End Point |
|---|---|---|---|---|---|---|---|
| CAPN3-KO | CTX + AAV.CAPN3 | 16 | | | | | |
| Young | | 8 | 6 wks/i.m./30 µl | 8 wks | 1e11 vg in 30 µl PBS, i.m. | 8 wks | 16 wks |
| Old | | 8 | 22 wks/i.m./30 µl | 24 wks | 1e11 vg in 30 µl PBS, i.m. | 8 wks | 32 wks |
| Wild type | CTX only | 18 | | | | | |
| Young | | 8 | 6 wks/i.m./30 µl | 8 wks | 30 µl PBS | 8 wks | 16 wks |
| Old | | 8 | 22 wks/i.m./30 µl | 24 wks | 30 µl PBS | 8 wks | 32 wks |

Eight weeks post-rAAV injection, end point studies carried out as described in Example 6 below include muscle physiology (TA force generation and protection from eccentric contractions), quantitative muscle histopathology, hCAPN3 detection using qPCR and western blot analysis.

Example 6

End Point Studies

TA Force Generation and Protection from Eccentric Contractions

A protocol to assess functional outcomes in the TA muscle is performed on muscles extracted from mice [Wein et al., *Nature Medicine*, 20(9):992-1000 (2014)]. Mice are anesthetized using ketamine/xylazine mixture. Using a dissecting scope, the hind limb skin is removed to expose the TA muscle and the patella. The distal TA tendon is dissected out and a double square knot is tied around the tendon with 4-0 suture as close to the muscle as possible, and the tendon is cut. The exposed muscle is constantly dampened with saline. Mice are then transferred to a thermal-controlled platform and maintained at 37 degrees. The knee is secured to the platform with a needle through the patella tendon, the distal TA tendon suture to the level arm of the force transducer (Aurora Scientific, Aurora, ON, Canada), and the foot is secured with tape. The TA muscle contractions are elicited by stimulating the sciatic nerve via bipolar platinum electrodes. Once the muscle is stabilized, the optimal length was determined by incrementally stretching the muscle until the maximum twitch force was achieved. After a 3 min rest period, the TA is stimulated at 50,100,150 and 200 Hz, allowing a 1 min rest period between each stimulus to determine maximum tetanic force. Muscle length is measured. Following a 5 min rest, the susceptibility of the TA muscle to contraction induced damage is assessed. After 500 ms of stimulation, the muscle is lengthened by 10% of the optimal length. This includes stimulating the muscle at 150 Hz for 700 ms. After the stimulation, the muscle is returned to the optimal length. The cycle is repeated every minute for a total of 10 cycles. Specific force is calculated by dividing the maximum tetanic force by the TA muscle cross-sectional area. After the eccentric contractions, the mice are then and is carried out using muscle physiology apparatus (Aurora Scientific, ON, Canada). The animal is anesthetized with isoflurane. Once the animal is anesthetized, the hair from the back and the hind limb will be removed as needed with clippers. If hair removal with clippers is insufficient, a thin layer of hair-removal cream (Nair) is applied, and the site thoroughly cleaned with warm water to prevent discomfort. The hindlimb to be measured is attached to the foot plate with adhesive tape. The limb is held rigid in a blunt clamp. Either the tibial or peroneal component of the sciatic nerve will be stimulated with two sterile, disposable 28 gauge monopolar electrodes inserted through the skin, subcutaneously near the nerve. Mouse temperature will be maintained by conductive thermoregulated heating pad (set at 37° C.) or radiant heat source and monitored by temperature probe.

Histopathology

For histological analysis all muscles and organs are embedded in 7% gum tragacanth and flash frozen in liquid nitrogen cooled isopentane. Frozen sections (12 µm) are collected for immunohistochemistry and western blot analysis.

Western Blot Analysis for Detection of Human CAPN3

CAPN3 protein quantification in mouse muscle tissues is assessed using a Western blotting method. The CAPN3 enzyme is resolved by sodium dodecyl sulfate polyacrylamide gel electrophoresis (SDS-PAGE) and migrates as a 94 kDa band with an autolytic product at approximately 60 kDa using Novocastra's clinical-grade antibody recognizing the N-terminus, NCL-CALP-12A2. Additionally, NCL-CALP-2C4 antibody recognizes this same CAPN3 molecular weight (94 kD), and an additional fragment (30 kD) in skeletal muscle; both antibodies are suitable for protein detection. A semi-quantitative measure of CAPN3 protein expression levels within the calpain-knockout mouse samples following delivery of the therapeutic rAAV vector is performed and compared with untreated controls.

Quantitative Muscle Histology

Cross sections of TA and quad muscles from treated with AAVrh.74.tMCK.CAPN3 versus control uninjected, are stained with hematoxylin and eosin, and photographed using Zeiss Axiovision L4 software (4 random 20× images per section per animal). Fiber size diameters are compared between treated and controls.

Statistical Analysis

Student's t-test or one-way ANOVA multiple comparison tests are performed where applicable.

Example 7

Toxicology/Biodistribution Studies

Toxicology/biodistribution studies are carried out using the established efficacious dose and one log higher dose. Toxicology studies are done by systemic (tail vein) delivery of rAAV to 6-8 week old CAPN3-KO mice including comparison to normal C57B16 normal mice. Cohorts of 6-10 mice are included and full necropsies are done using GLP-like methods.

Serum collected from blood samples is used for Clinical Chemistries: Alanine aminotransferase, Alkaline Phosphatase, Aspartate aminotransferase, Bilirubin (Total and Direct), Blood Urea nitrogen, Creatinine, Creatine Kinase, Glucose, and Total Protein.

A full necropsy is performed with a thorough and systematic examination and dissection of the animal viscera and carcass. The tissues/organs are collected include gonads, brain, spleen, kidneys, jejunum, colon, pancreas, heart, lung, stomach, liver, inguinal lymp nodes, spinal cord gastocnemius and quadriceps. Tissues/organs for histopathology studies are collected and fixed in 10% neutral buffered formalin (10% NBF), with the exception of all skeletal muscle specimens which are mounted on blocks with OCT, and flash frozen in liquid nitrogen-cooled methyl-butane for cryosections.

Example 8

In Vivo Biopotency Testing Following Intramuscular Injection

In vivo biopotency testing was carried out following intramuscular (IM) injection of AAVrh.74.tMCK.CAPN3 (1E11 vg) into the tibialis anterior (TA) muscle in CAPN3 KO mice (n=3) as described above in Example 5.

Figure 3:
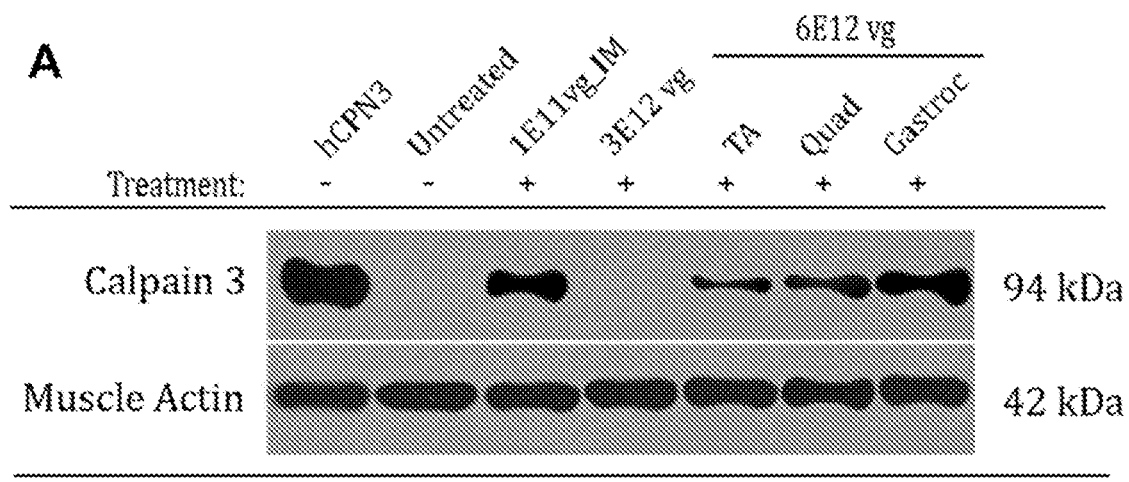
FIGS. 3A-3B provide Western Blot (panel A) and RT-PCR (panel B) data after AAVrh.74.tMCK.CAPN3 administration via intramuscular injection (1E11 vg) and systemic injection (3E12 vg and 6E12 vg). This data was compared with normal human muscle lysate (Gel load of 60% total protein as compared to mouse lysates) and untreated CAPN3-KO mice.
Figure 3:
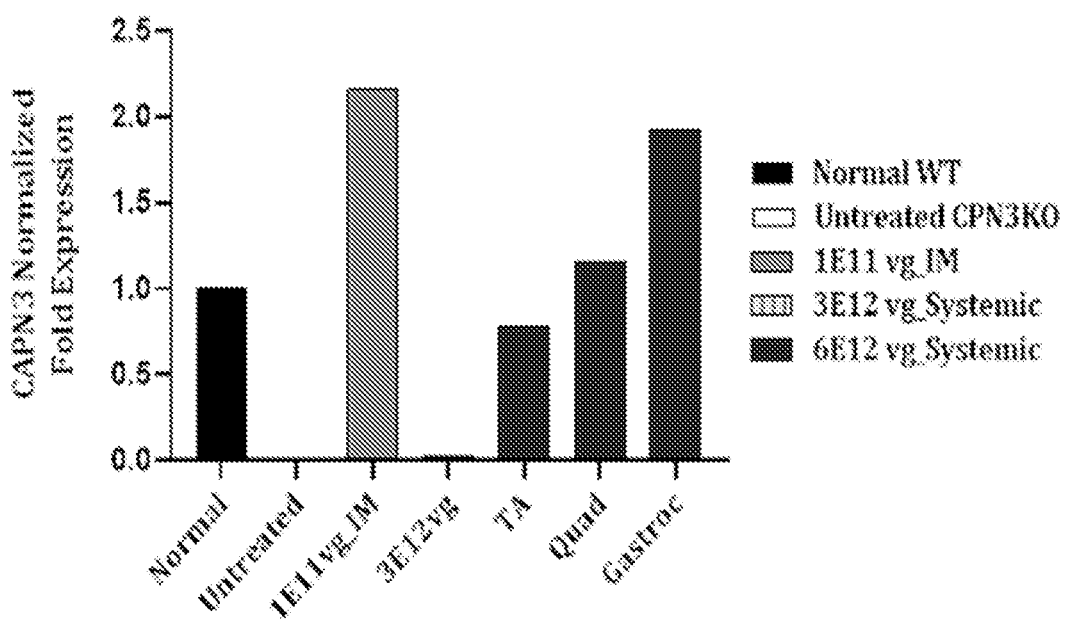
Figure 4:
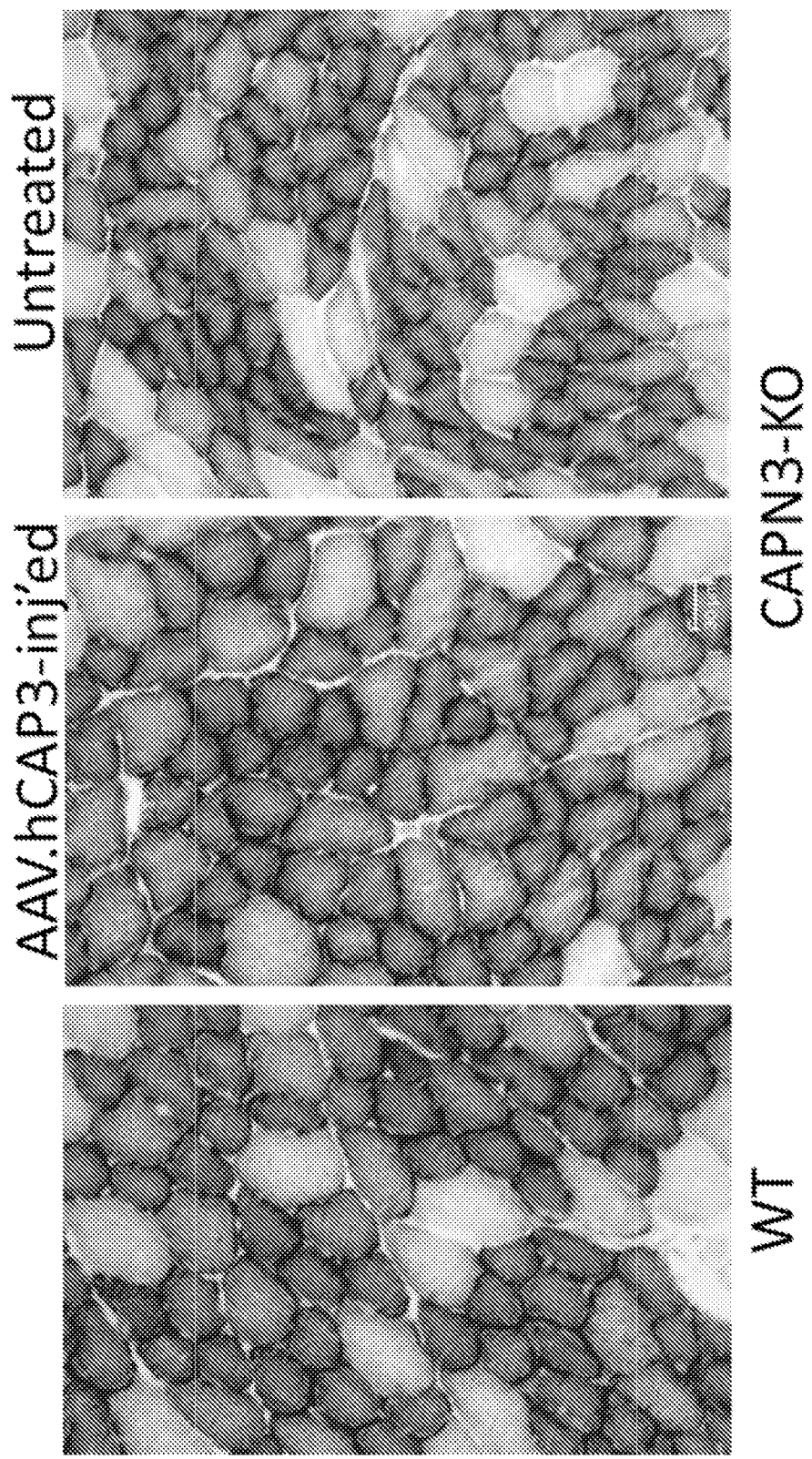
FIG. 4 provides representative images of SDH-stained tissue sections of CAPN3 KO (AAV.hCAPN3 gene injected and untreated) and wild type (WT) TA muscles. Mean fiber size of slow twitch oxidative (STO, dark), fast twitch oxidative (FTO, intermediate) and fast twitch glycolytic (FTG, light) fibers appeared normalized towards WT values in the TA muscle of mice treated with AAVrh.74.tMCK.CAPN3. Fiber type sizes with and without treatment are illustrated in the Table 4.

At 4 weeks post-administration, gene delivery was analyzed by reverse transcription quantitative PCR (RT-qPCR) and western blot analyses. For the Western blot analysis, samples corresponding to 50 μg of whole muscle protein extracts were separated on a 3-8% acrylamide, Tris-Acetate SDS gel and transferred to a PVDF membrane. Immunodetection was performed with a monoclonal antibody raised against s synthetic peptide containing AAs 1-19 of the human Calpain 3 sequence (Leica), and muscle specific actin antibody (Leica) as a loading control. FIG. 3A demonstrates that the presence of the 94 kD calpain 3 protein in the TA muscle after intramusclular injection. The RT-qPCR analysis demonstrated relative expression levels of human Calpain 3 gene 4 weeks post-gene transfer return to normalized levels as compared to WT mice (see FIG. 3B).

Mouse GAPDH was used as a reference gene and WT C57BL/6 was used to calibrate the RT-qPCR data.

In addition, quantitative histopathological analysis was carried out after intramuscular administration. As shown in, the diameter of the TA muscle fiber of the treated CAPN3 KO mice was compared to that of the untreated control (ringer lactate injected TA) muscle. Mean fiber size of slow twitch oxidative (STO, dark), fast twitch oxidative (FTO, intermediate) and fast twitch glycolytic (FTG, light) fibers appeared normalized towards WT values in the AAV.hCAPN3 injected TA muscle. The quantification of the fiber type size is provided in Table 4 and illustrates an increase with treatment.

TABLE 4

| | WT (z18-14) | | Treated (z18-11) | | Untreated (z18-22 L) | |
|---|---|---|---|---|---|---|
| | number | diameter (μm) | number | diameter (μm) | number | diameter (μm) |
| STO | 246 | 28.06 ± 0.27 | 142 | 28.89 ± 0.32 | 240 | 25.57 ± 0.27 |
| FTO | 63 | 36.65 ± 0.53 | 86 | 36.71 ± 0.58 | 110 | 32.19 ± 0.48 |
| FTG | 82 | 42.55 ± 0.53 | 86 | 43.68 ± 0.66 | 128 | 35.49 ± 0.50 |
| All fiber | 391 | 32.45 ± 0.38 | 314 | 35.08 ± 0.45 | 478 | 29.75 ± 0.30 |

In summary, the in vivo biopotency testing following IM injection of the vector (1E11 vg) into tibialis anterior (TA) muscle in CAPN3 KO mice (n=2) demonstrated that 4 weeks post-gene delivery 1) RT-qPCR and western blot analyses showed expressions of CAPN3 transcripts and 94 kDa full-length calpain 3 protein and 2) histological analysis showed an increase in the muscle fiber diameter of TA compared to the control (Ringer's lactate injected TA) muscle.

Example 9

In Vivo Biopotency Testing Following Systemic Injection

In vivo biopotency testing was carried out following systemic injection of AAVrh.74.tMCK.CAPN3 (3E12 vg or 6E12 vg) via the tail vein of CAPN3-KO mice. The low dose CAPN3KO cohort (n=5; mice were denoted as Z18-13, Z18-15, Z18-16, Z18-17, Z18-18) received 3E12 vg in 300 μl Ringer's lactate. At 4 weeks post-gene injection, mice were evaluated for running fatigue by the run-to-exhaustion treadmill test and then euthanized for tissue collection. Muscles from upper and lower limbs (TA, gastrocnemius (GAS), quadriceps, triceps), heart, liver spleen, lung, ovaries and testicles were removed, and tissue samples were frozen in isopentane, and cooled in liquid nitrogen.

RT-qPCR CAPN3 expression was evaluated in TA muscles. For the 3E12 vg low dose, CAPN3 mRNA expression levels were low as observed by high CT values, >27. Western blot analysis showed undetectable corresponding protein bands. Even though low expression data was observed in this tissue for the low dose, both functional and histological benefits were demonstrated with the systemic administration of 3E12 vg.

Subsequently, a higher dose (6E12 vg) was systemically administered to investigate whether protein expression could be detected at a higher dose of vector delivery. The high dose cohort (mice denoted as Z18-20, Z18-21, Z18-23 and Z18-24) CAPN3-KO mice received 6E12 vg AAVrh7.4.tMCK.hCAPN3 vector (twice the dose used in the low dose cohort via systemic injection to the tail vein), and were euthanized 4 weeks post-injection. RT-qPCR showed variable levels of CAPN3 expression in the quad, triceps, GAS, TA and cardiac muscle.

To determine relative expression of the CAPN3 mRNA, muscle tissue samples were collected from CAPN3 KO mice treated with tMCK.hCAPN3 vector at the dose of 3E12 vg (low dose cohort 1) and 6E12 vg (high dose cohort 2). Total RNA was isolated from both cohorts and qPCR of CAPN3 vs. mouse GAPDH were assayed along with the previous samples from the cohort that received the vector via IM injection (1E11 vg; see above in Example 8).

The relative expression of CAPN3 was determined by the method below:

$$CT = CT_{CAPN3} - CT_{mGAPDH}$$

$$\Delta\Delta CT = \Delta CT - \Delta CT_{Calibrator}$$

Relative Expression of $CAPN3 = 2^{-\Delta\Delta CT}$

Figure 5:
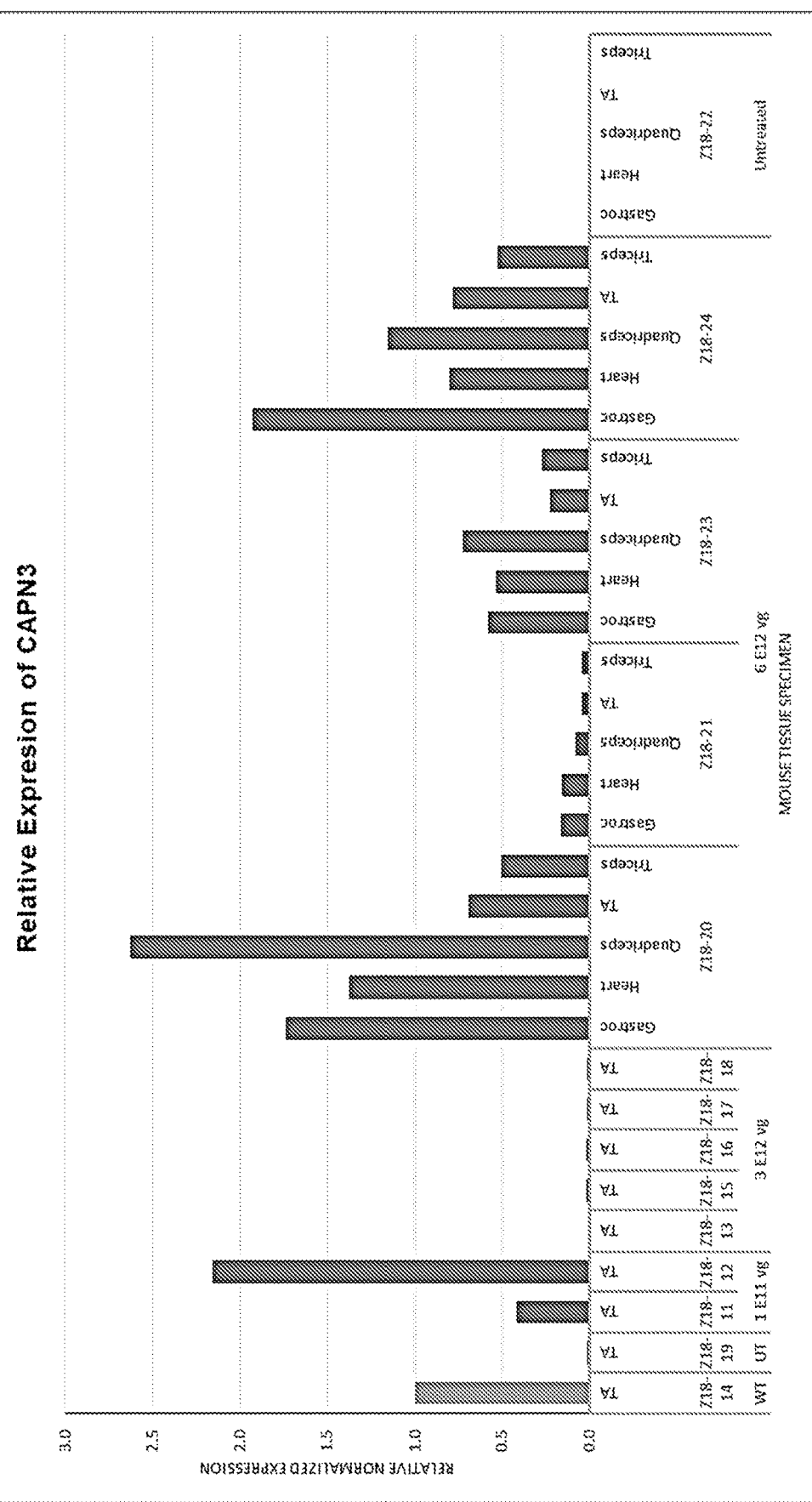
FIG. 5 provides relative CAPN3 protein expression levels in WT (Z18-14) and TA muscles from the low dose cohort (3E12 vg, Z18-13, Z18-15, Z18-16, Z18-17, Z18-18), and gastrocnemius (gastroc), heart, quadriceps, tibialis anterior (TA) and triceps from the high dose cohort (6E12 vg, Z18-20, Z18-21, Z18-23, Z18-24, Z18-22) are shown (UT: untreated).

The relative expression of CAPN3 in each tissue and the original CT value were shown in the Table 5 below and in FIG. 5. Table 5 provides data for IM delivery (mice nos. Z18-11 and Z18-12) and for systemic delivery specific variability and lower relative expression as compared to the IM delivery at 1E11 vg (<1% of IM delivery); this was especially true for the 3E12 low dose cohort. Accordingly, the full-length 94 kDa protein was below the limit of detection by Western blot. However, robust gene expression and prominent amounts of full-length Calpain 3 protein were exhibited following systemic injection of 6E12 vg systemic dosage in the high dose cohort.

Example 10

Assessment of Systemic AAVrh74.tMCK.hCAPN3 Gene Delivery

Gene transfer efficiency was assessed by qPCR, calculating vector genome copies within CAPN3 KO mouse tissue samples following systemic delivery of AAVrh74.tMCK.hCAPN3 at 6E12 vg. The vector genome load of the lower and upper extremity skeletal muscles (quad, TA, gastroc, triceps), heart and liver was determined. Genomic DNA was isolated from frozen tissue samples. The qPCR assay was performed on an ABI 7500 (Applied Biosystems) using the following primer set: "5'-CG-

TABLE 5

CAPTN3 RT-PCR:

| Mice No. | Tissue | Genotype | Dose of Treatment (DRAPs per Mice) | CAPN3 | | mGAPDH | | ΔCT | ΔΔCT | $2^{(-\Delta\Delta CT)}$ |
|---|---|---|---|---|---|---|---|---|---|---|
| Z18-14* | TA | WT | 0 | 22.437 | 22.456 | 15.234 | 15.274 | 7.193 | 0.000 | 1.0003 |
| Z18-19 | TA | CAPN3 | 0 | 35.259 | 32.705 | 15.159 | 15.176 | 18.814 | 11.621 | 0.0003 |
| Z18-11 | TA | KO | 1E11 | 24.338 | 24.217 | 15.800 | 15.835 | 8.460 | 1.267 | 0.4155 |
| Z18-12 | TA | | | 21.030 | 21.104 | 14.906 | 15.058 | 6.085 | -1.108 | 2.1548 |
| Z18-13 | TA | | 3E12 | 32.376 | 32.430 | 15.236 | 15.203 | 17.183 | 9.990 | 0.0010 |
| Z18-15 | TA | | | 27.407 | 27.443 | 14.510 | 14.520 | 12.910 | 5.717 | 0.0190 |
| Z18-16 | TA | | | 28.609 | 28.333 | 15.229 | 15.259 | 13.227 | 6.034 | 0.0153 |
| Z18-17 | TA | | | 28.675 | 28.670 | 14.997 | 15.005 | 13.671 | 6.478 | 0.0112 |
| Z18-18 | TA | | | 27.869 | 28.128 | 14.522 | 14.544 | 13.466 | 6.273 | 0.0129 |
| Z18-20 | Gastroc | | 6E12 | 22.271 | 22.439 | 15.939 | 15.974 | 6.398 | -0.795 | 1.7347 |
| | Heart | | | 21.996 | 22.051 | 15.267 | 15.315 | 6.732 | -0.461 | 1.3762 |
| | Quadriceps | | | 21.008 | 21.202 | 15.203 | 15.407 | 5.800 | -1.393 | 2.6262 |
| | TA | | | 23.806 | 24.173 | 16.169 | 16.385 | 7.713 | 0.520 | 0.6975 |
| | Triceps | | | 24.083 | 24.361 | 15.978 | 16.097 | 8.185 | 0.992 | 0.5027 |
| Z18-21 | Gastroc | | | 25.330 | 25.221 | 15.461 | 15.462 | 9.814 | 2.621 | 0.1625 |
| | Heart | | | 25.024 | 24.819 | 15.032 | 15.097 | 9.857 | 2.664 | 0.1577 |
| | Quadriceps | | | 26.278 | 26.108 | 15.285 | 15.370 | 10.866 | 3.673 | 0.0784 |
| | TA | | | 26.649 | 26.697 | 15.017 | 15.010 | 11.659 | 4.466 | 0.0452 |
| | Triceps | | | 27.040 | 27.134 | 15.321 | 15.343 | 11.755 | 4.562 | 0.0423 |
| Z18-23 | Gastroc | | | 24.150 | 24.144 | 16.225 | 16.117 | 7.976 | 0.783 | 0.5812 |
| | Heart | | | 22.799 | 22.495 | 14.593 | 14.502 | 8.099 | 0.906 | 0.5335 |
| | Quadriceps | | | 24.248 | 24.076 | 16.511 | 16.504 | 7.655 | 0.462 | 0.7262 |
| | TA | | | 25.554 | 25.338 | 16.124 | 16.054 | 9.357 | 2.164 | 0.2231 |
| | Triceps | | | 24.396 | 24.383 | 15.363 | 15.277 | 9.070 | 1.877 | 0.2723 |
| Z18-24 | Gastroc | | | 24.444 | 24.165 | 18.083 | 18.036 | 6.245 | -0.948 | 1.9297 |
| | Heart | | | 22.769 | 22.425 | 15.100 | 15.077 | 7.508 | 0.315 | 0.8037 |
| | Quadriceps | | | 22.754 | 22.521 | 15.637 | 15.672 | 6.983 | -0.210 | 1.1568 |
| | TA | | | 23.491 | 23.555 | 15.979 | 15.974 | 7.547 | 0.354 | 0.7826 |
| | Triceps | | | 24.554 | 24.403 | 16.370 | 16.329 | 8.128 | 0.935 | 0.5229 |
| Z18-22 | Gastroc | | 0 | 31.878 | 31.962 | 15.433 | 15.527 | 16.440 | 9.247 | 0.0016 |
| | Heart | | | 31.407 | 32.964 | 16.006 | 15.972 | 16.197 | 9.004 | 0.0019 |
| | Quadriceps | | | 32.332 | 33.464 | 16.528 | 16.468 | 16.400 | 9.207 | 0.0017 |
| | TA | | | 35.584 | 33.917 | 16.451 | 16.372 | 18.339 | 11.146 | 0.0004 |
| | Triceps | | | 33.615 | 32.786 | 15.742 | 15.628 | 17.516 | 10.323 | 0.0008 |
| Human Tissue | Muscle | | | 23.547 | 23.539 | 37.743 | 38.262 | | | |
| pAAV.tMCK. hCAPN3 | | | 1 pg/uL | 16.328 | 16.413 | UD | 38.302 | | | |

*Calibrator

Overall, the CAPN3 mRNA expression in the CAPN3 KO muscle following systemic delivery had animal- and tissue- GAGAGCAACTGCATAAG-3' (Forward; SEQ ID NO: 8); "5'-GGCTGATGATGGCTGAATAG-3' (Reverse; SEQ ID NO: 9). The primer pair exclusively amplifies a product from the 5' region of the hCAPN3 ORF, and region downstream unique to the expression vector, including portions of an intronic element. The final results are reported as mean copy number of AAVrh74 vector per microgram of genomic DNA.

Figure 6:
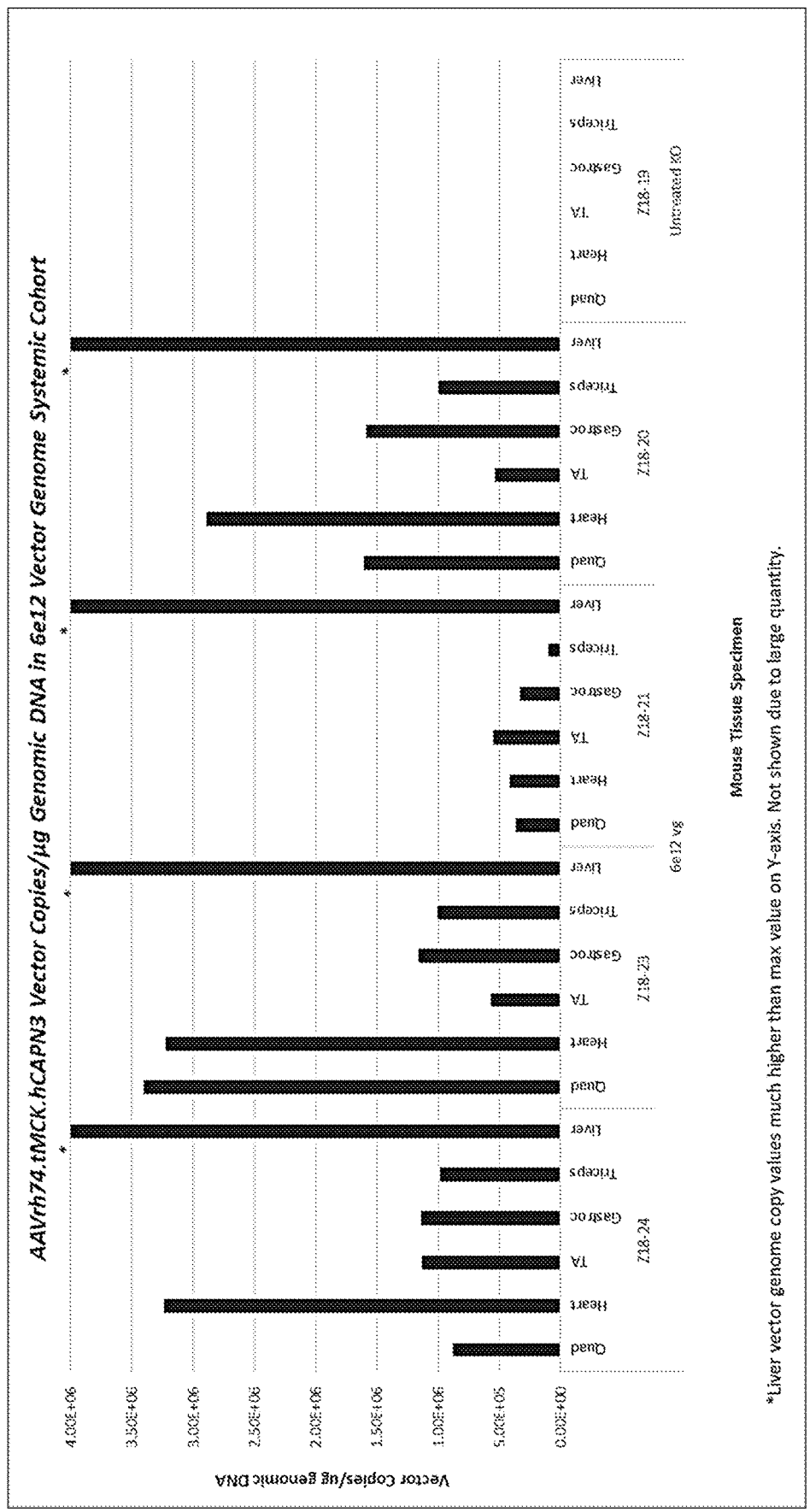
FIG. 6 provides AAVrh74.tMCK.hCAPN3 vector copies/μg genomic DNA in 6E12 vector genome systemic high dose cohort in the following muscles: quadriceps (quad), heart, tibialis anterior (TA), gastrocnemius (gastroc) triceps, and the liver.

As shown in FIG. 6, the highest vector genome copy number was present in the liver following systemic vector delivery. Vector genome distribution was variable between the muscle groups. Overall the values were higher in the quadriceps and heart tissue compared to other muscles. Experimental variability was also noted; as the case with Mouse no. Z18-21 which showed relatively lower copy numbers in all muscle groups compared to other 3 mice.

Improvement in both functional and histological features were observed in the 3E12 vg systemically treated CAPN3 KO mice, however, only low levels of muscle Calpain 3 expression were detected in total RNA isolates by RT-qPCR and the full-length 94 kDa protein was undetectable by Western blot for the particular muscle tissue (See FIG. 3A). However, robust gene expression and prominent amounts of full-length Calpain 3 protein were exhibited following the 6E12 vg systemic dosage (see FIG. 3B). The data demonstrates that Calpain 3 gene expression returned to normalized levels as compared to WT mice after 4 weeks post-gene transfer of the AAVrh74.tMCK.hCAPN3 particles. Mouse GAPDH was used as a reference gene and WT C57BL/6 to calibrate the RT-qPCR data.

Histopathology

Figure 7:
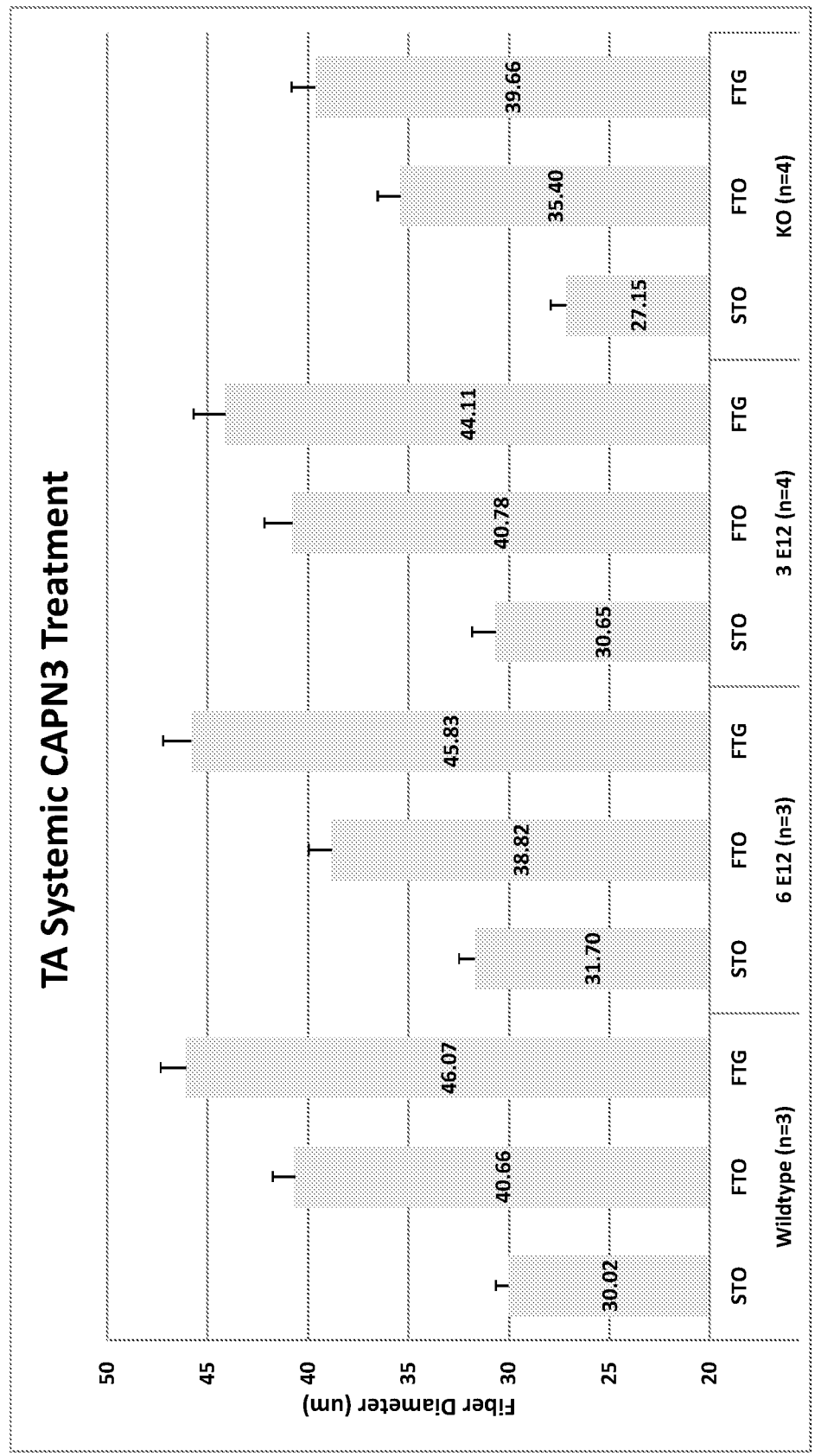
FIG. 7 provides the mean fiber diameters of slow twitch oxidative (STO, dark), fast twitch oxidative (FTO, intermediate) and fast twitch glycolytic (FTG, light) fibers from left TA muscle following systemic administration of AAVrh.74.tMCK.CAPN3 at 3E12 and 6E12 vg. Data from untreated CAPN3KO and WT mice was included.

As discussed above, an efficacy trend at 4 weeks post-injection was observed. A significant increase in fiber size was observed in the TA muscle from CAPN3 KO mice following systemic delivery of AAVrh.74.tMCK.hCAPN3 at 4 week-post injection in both cohorts (3E12 and 6E12). As shown in FIG. 7, total fiber diameter was significantly increased in both of the treated cohorts compared to untreated KO counterparts ($p<0.00001$). Treatment resulted in normalization of fiber size and there was no dose-related difference between the treatment cohorts ($p=0.78058$). Table 6 provides the muscle fiber sizes in wild type and CAPN3 KO mice following systemic AAV.hCAPN3 gene therapy at 3E12 and 6E12 vg.

determined when the mouse sits on the rest pad for at least 15 seconds. The time, speed and distance to exhaustion were recorded.

Figure 8A:
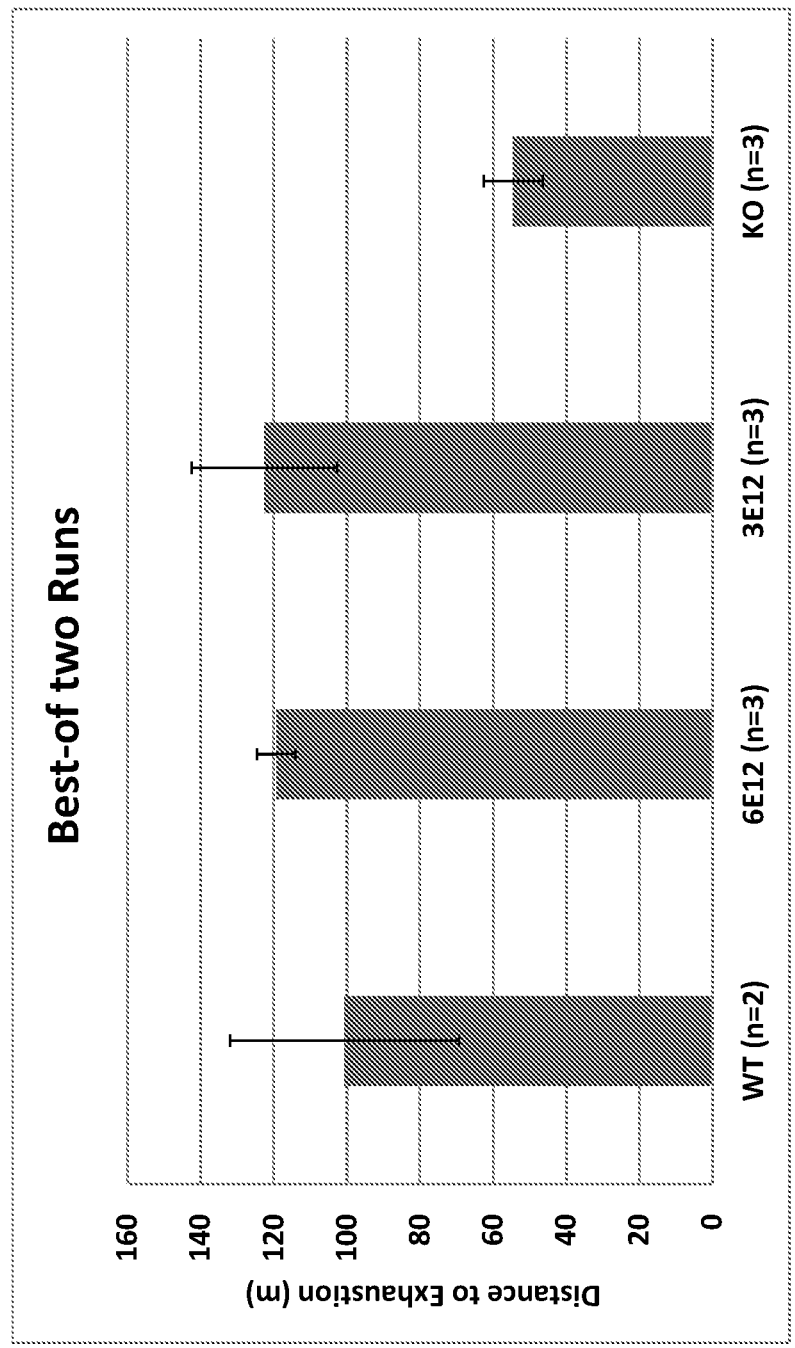
FIG. 8A provides data for the low dose cohort, which received 3E12 vg of AAVrh.74.tMCK.CAPN3, and the high dose cohort, which received 6E12 vg of AAVrh.74.tMCK.CAPN3 4 weeks after systemic administration. Treated CAPN3 KO mice performed better on Run-to-Exhaustion test compared to untreated counterparts.

FIG. 8A provides data for the run-to-exhaustion test for the low dose cohort, which received 3E12 vg of AAVrh7.4.tMCK.hCAPN3, and the high dose cohort 2, which received 6E12 vg of AAVrh7.4.tMCK.hCAPN3 as assessed 4 weeks after systemic administration. Treated CAPN3 KO mice in both cohorts performed better on the Run-to-Exhaustion test compared to untreated counterparts. There was no apparent dose-related difference in the Run-to-Exhaustion test performance or statistical difference in muscle fiber diameter between the low and high dose cohorts.

Figure 8B:
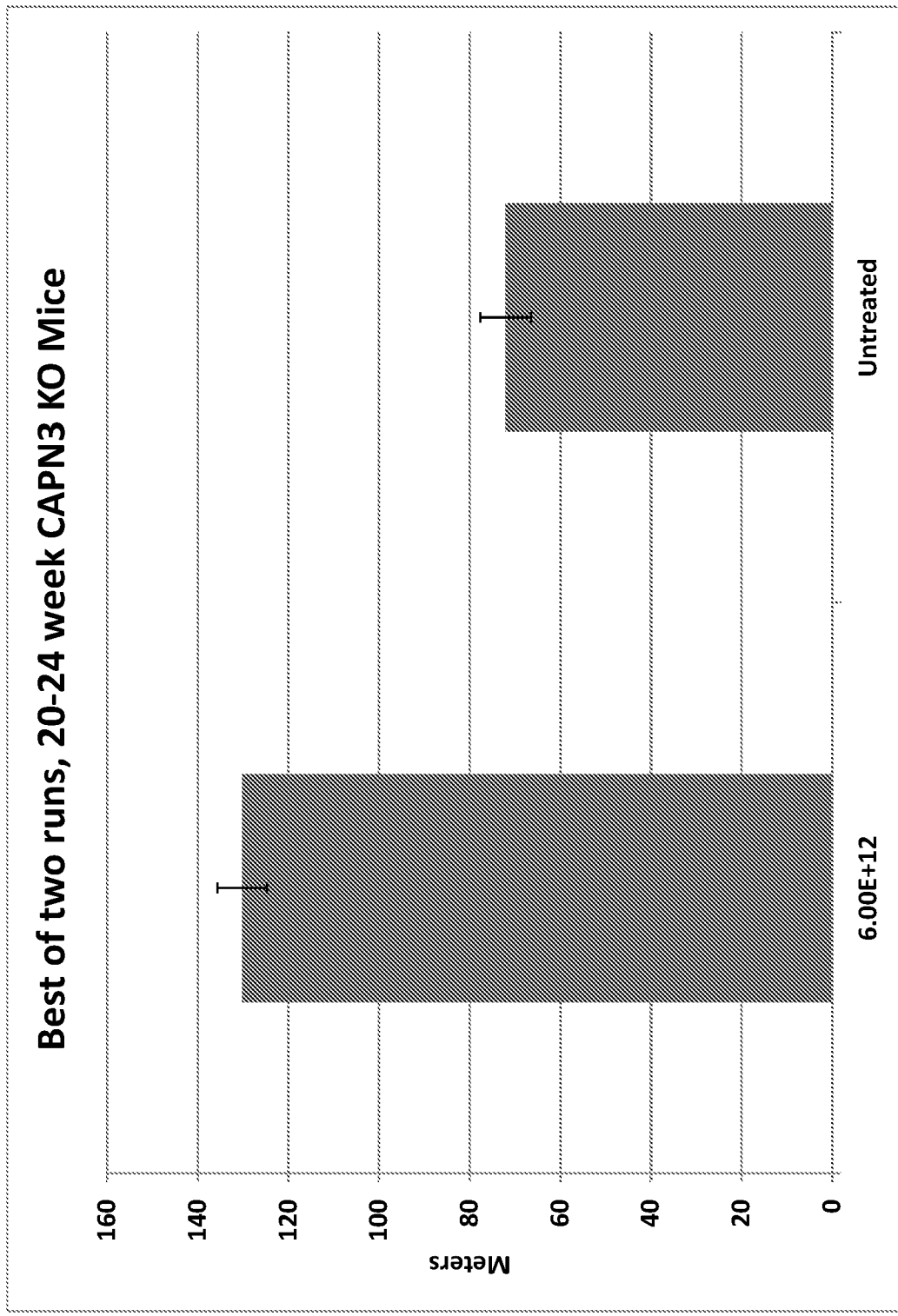
FIG. 8B provides data for the high dose cohort, in which the mice were tested 20-24 weeks after systemic administration of 6E12 vg of AAVrh.74.tMCK.CAPN3 (n=5) and untreated counterparts (n=16)

Mice from the high dose cohort 2 (n=16) were further analyzed 20-24 weeks after administration of 6E12 vg of AAVrh7.4.tMCK.hCAPN3. As shown in FIG. 8B, the treated CAPN3 KO mice continued to perform better on the Run-to-Exhaustion test compared to untreated counterparts ($p<0.00001$).

Example 11

Assessment of Cardiac Toxicity Following Systemic Injection of AAVrh7.4.tMCK.hCAPN3 Vector After the mice of the cohorts were euthanized at 4 weeks post injection, serum and organ samples were collected. The low dose cohort 1 CAPN3KO cohort (n=5) received 3E12 vg in 300 µl Ringer's lactate of AAVrh.74.tMCK.hCAPN3 vector via tail vein injection. The high dose cohort 2CAPN3-KO mice received 6E12 vg AAVrh7.4.tMCK.hCAPN3 vector via tail vein, and both cohorts were euthanized 4 weeks post-injection. Two sections through the apex of the heart, superficial and deep regions of ventricles were examined. No inflammation, necrosis or regeneration was found in the tissue sections indicating no toxic effects were observed on the heart muscle from the systemic delivery of AAVrh7.4.tMCK.hCAPN3 vector at two different doses at 4 weeks post-injection. Mice nos. Z18-19 and Z18-22 (Ringer's lactate-injected/untreated) served as control KO animal.

TABLE 6

| | WT (n = 3) | | 6 E12 CAPN3 (n = 3) | | 3E12 CAPN3 (n = 4) | | KO (n = 4) | |
|---|---|---|---|---|---|---|---|---|
| | number | diameter (µm) | number | diameter (µm) | number | diameter (µm) | number | diameter (µm) |
| STO | 532 | 30.0 ± 0.6 | 441 | 31.7 ± 0.8 | 464 | 30.7 ± 1.2 | 858 | 27.2 ± 0.8 |
| FTO | 278 | 40.7 ± 1.1 | 345 | 38.8 ± 1.1 | 447 | 40.8 ± 1.4 | 364 | 35.4 ± 1.1 |
| FTG | 275 | 46.1 ± 1.3 | 226 | 45.8 ± 1.4 | 403 | 44.1 ± 1.6 | 455 | 39.7 ± 1.2 |
| All fiber | 1085 | 38.9 ± 1.8 | 1012 | 38.8 ± 2.0 | 1314 | 38.5 ± 2.4 | 1677 | 34.1 ± 1.8 |

There was no histopathological evidence of cardiac toxicity following systemic injection of AAVrh7.4.tMCK.hCAPN3 vector at 4 weeks in either cohort. There were variable amounts of virus found in the heart tissue, however no protein bands were detected in the heart tissue by Western blot in either cohort.

Functionality Study: Run-to-Exhaustion Test

Figure 9:
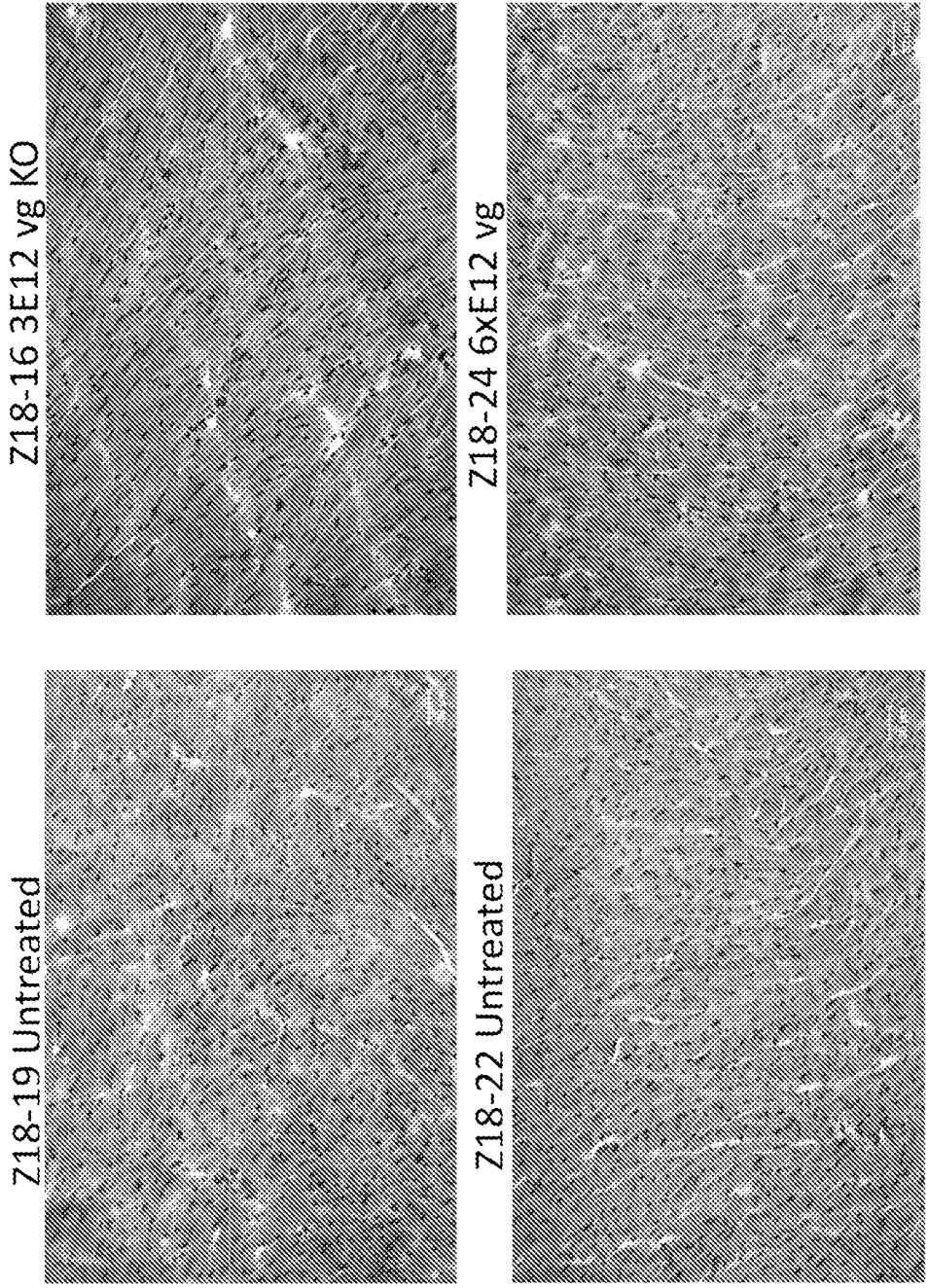
FIG. 9 provides hematoxylin & eosin(H&E) stained fresh frozen sections of the left ventricles from representative heart samples of CAPN3 KO mice at 4 weeks post-systemic injection of the AAVrh7.4.tMCK.hCAPN3 vector at 3E12 vg and 6E12 vg doses with matching untreated controls.
Figure 10:
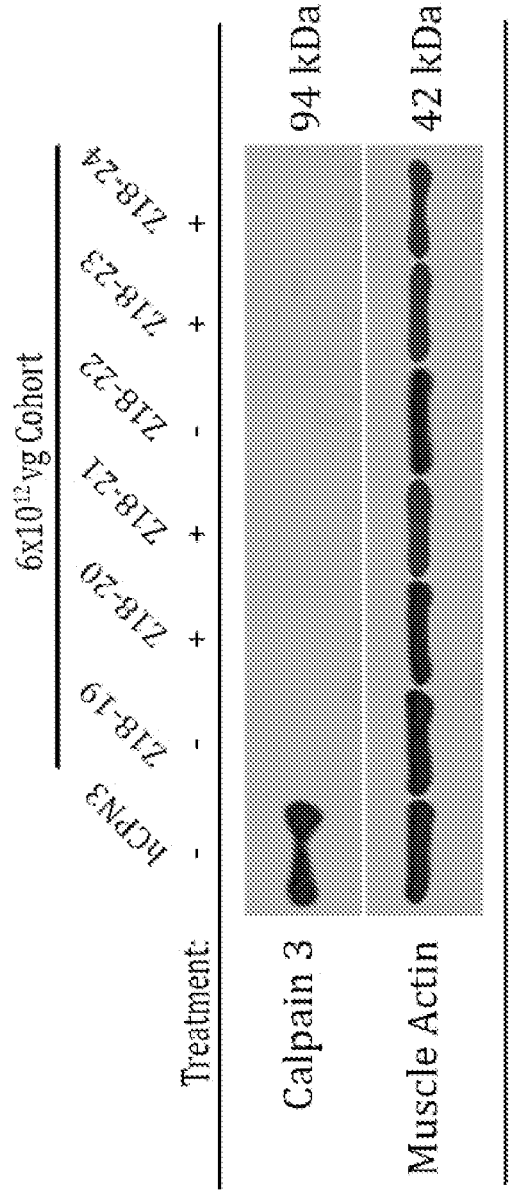
FIG. 10 provides Western blot analysis of the cardiac tissues from the high dose cohort (which received 6E12 vg of AAVrh7.4.tMCK.hCAPN3. This analysis showed no or minimum detectable calpain 3 protein in the heart of the treated animal. Animal identification numbers Z18-19 and 22 represent the lysates from the untreated CAPN3 KO mice.

Mice were accustomed to the treadmill (Columbus Instruments) with a 15-minute run once per day at 10 m/min for 3 days prior to data acquisition for Run-to-Exhaustion test. The protocol used required having mice on a treadmill that is at a 15-degree incline. The treadmill was turned on at a speed at 1m/min and the speed was increased by 1m every minute until the mouse got exhausted. Exhaustion was FIG. 9 provides H&E stained fresh frozen sections from the heart. Muscle fiber necrosis, regeneration or inflammation was not seen. Even though there were variable amounts of viruses present in the heart tissue, no protein bands were detected by Western blot in either cohort. FIG. 10 provides the Western blot analysis which shows the full-length Calpain 3 protein is below the limit of detection in the heart tissues after the transduction.

Example 12

In Vivo Physiological Analysis

Physiological assessment is carried out after IM or systemic administration of the AAVrh7.4.tMCK.hCAPN3 vector. During the in vivo physiological assessments, the mice are anesthetized with inhaled isoflurane. Once the animal is anesthetized, the hair from the back and the hind limb is removed as needed with clippers. If hair removal with clippers is insufficient, a thin layer of hair-removal cream is applied. During in vivo physiological force measurements, torque from the hind limb is measured with a non-invasive force foot plate connected to force detecting motor (Aurora Scientific, Canada) following supramaximal stimulations of the sciatic nerve. The hind limb to be measured is attached to the foot plate with adhesive tape. The limb is held rigid in a blunt clamp. Either the tibial or peroneal component of the sciatic nerve is stimulated with two sterile disposable 28 gauge monopolar electrodes inserted subcutaneously near the nerve. Mouse temperature is maintained by conductive thermoregulated heating plate (set at 37° C.) or radiant heat source and monitored by infrared temperature probe.

While the present disclosure provides specific embodiments, it is understood that variations and modifications will occur to those skilled in the art. Accordingly, only such limitations as appear in the claims should be placed on the invention.

All documents referred to in this application are hereby incorporated by reference in their entirety.

I claim:

1. A recombinant adeno-associated virus (rAAV) comprising a polynucleotide which comprises nucleotides 1 to 3977 of SEQ ID NO: 1, wherein the rAAV comprises an AAV-8, an AAV-9, or an AAV rh.74 capsid protein, or a variant of each thereof.

2. The rAAV of claim 1, wherein the rAAV comprises an rh.74 capsid protein.

3. A composition comprising the rAAV of claim 1.

4. A composition comprising the rAAV of claim 2.

* * * * *

SEQUENCE LISTING

```
<160> NUMBER OF SEQ ID NOS: 9

<210> SEQ ID NO 1
<211> LENGTH: 7629
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: AAVrh.74.tMCK.CAPN3 recombinant genome
<220> FEATURE:
<221> NAME/KEY: misc_feature
<222> LOCATION: (1)..(128)
<223> OTHER INFORMATION: AAV2 ITR
<220> FEATURE:
<221> NAME/KEY: misc_feature
<222> LOCATION: (165)..(884)
<223> OTHER INFORMATION: tMCK promoter
<220> FEATURE:
<221> NAME/KEY: misc_feature
<222> LOCATION: (937)..(1069)
<223> OTHER INFORMATION: chimeric intron
<220> FEATURE:
<221> NAME/KEY: misc_feature
<222> LOCATION: (1101)..(1106)
<223> OTHER INFORMATION: Kozak Sequence
<220> FEATURE:
<221> NAME/KEY: misc_feature
<222> LOCATION: (1107)..(3572)
<223> OTHER INFORMATION: CAPN3 polynucleotide
<220> FEATURE:
<221> NAME/KEY: misc_feature
<222> LOCATION: (3581)..(3780)
<223> OTHER INFORMATION: poly A signal
<220> FEATURE:
<221> NAME/KEY: misc_feature
<222> LOCATION: (3850)..(3977)
<223> OTHER INFORMATION: second AAV2 ITR

<400> SEQUENCE: 1
gcgcgctcgc tcgctcactg aggccgcccg ggcaaagccc gggcgtcggg cgacctttgg      60
tcgcccggcc tcagtgagcg agcgagcgcg cagagaggga gtggccaact ccatcactag     120
gggttcctta atacgactca ctatagggcc gcaccggtaa gcttccacta cgggtctagg    180
ctgcccatgt aaggaggcaa ggcctgggga cacccgagat gcctggttat aattaacccc    240
aacacctgct gccccccccc ccccaacacc tgctgcctga gcctgagcgg ttaccccacc    300
ccggtgcctg ggtcttaggc tctgtacacc atggaggaga agctcgctct aaaaataacc    360
ctgtccctgg tggatccact acgggtctag gctgcccatg taaggaggca aggcctgggg    420
acacccgaga tgcctggtta taattaaccc caacacctgc tgccccccc ccccaacac     480 ctgctgcctg agcctgagcg gttacccac cccgtgcct gggtcttagg ctctgtacac     540
catggaggag aagctcgctc taaaaataac cctgtccctg gtggatccac tacgggtcta    600
```

```
ggctgcccat gtaaggaggc aaggcctggg gacacccgag atgcctggtt ataattaacc      660
ccaacacctg ctgccccccc cccccaaca cctgctgcct gagcctgagc ggttacccca      720
ccccggtgcc tgggtcttag gctctgtaca ccatggagga aagctcgct ctaaaaataa      780 ccctgtccct ggtggatcct ccctggggac agccctcct ggctagtcac accctgtagg      840
ctcctctata taacccaggg gcacagggc tgccccggg tcacggtgga tatccctgca      900
ggtaccacgc gctgtaattg aactgggagt ggacacctgt ggagagaaag gcaaagtgga      960
tgtcagtaag accaataggt gcctatcaga aacgcaagag tcttctctgt ctcgacaagc     1020 ccagttcta ttggtctcct taaacctgtc ttgtaacctt gatacttacg gagagcaact     1080
gcataagggc tagcctcgag gccaccatgc cgaccgtcat tagcgcatct gtggctccaa     1140
ggacagcggc tgagcccgg tccccagggc cagttcctca cccggcccag agcaaggcca     1200
ctgaggctgg gggtggaaac ccaagtggca tctattcagc catcatcagc cgcaattttc     1260
ctattatcgg agtgaaagag aagacattcg agcaacttca aagaaatgt ctagaaaaga     1320 aagttcttta tgtggaccct gagttccccac cggatgagac ctctctcttt tatagccaga     1380
agttccccat ccagttcgtc tggaagagac ctccggaaat ttgcgagaat ccccgattta     1440
tcattgatgg agccaacaga actgacatct gtcaaggaga gctaggggac tgctggttc     1500 tcgcagccat tgcctgcctg accctgaacc agcaccttct tttccgagtc atacccatg     1560 atcaaagttt catcgaaaac tacgcaggga tcttccactt ccagttctgg cgctatggag     1620
agtgggtgga cgtggttata gatgactgcc tgccaacgta caacaatcaa ctggtttca     1680 ccaagtccaa ccaccgcaat gagttctgga gtgctctgct ggagaaggct tatgctaagc     1740
tccatggttc ctacgaagct ctgaaaggtg ggaacaccac agaggccatg gaggacttca     1800
caggaggggt ggcagagttt ttgagatca gggatgctcc tagtgacatg tacaagatca     1860
tgaagaaagc catcgagaga ggctccctca tgggctgctc cattgatgat ggcacgaaca     1920
tgacctatgg aacctctcct tctggtctga acatggggga gttgattgca cggatggtaa     1980
ggaatatgga taactcactg ctccaggact cagacctcga ccccagaggc tcagatgaaa     2040
gaccgacccg gacaatcatt ccggttcagt atgagacaag aatggcctgc gggctggtca     2100
gaggtcacgc ctactctgtc acggggctgg atgaggtccc gttcaaaggt gagaaagtga     2160
agctggtgcg gctgcggaat ccgtgggcc aggtggagtg gaacggttct tggagtgata     2220
gatggaagga ctggagcttt gtggacaaag atgagaaggc ccgtctgcag caccaggtca     2280
ctgaggatgg agagttctgg atgtcctatg aggatttcat ctaccatttc acaaagttgg     2340
agatctgcaa cctcacggcc gatgctctgc agtctgacaa gcttcagacc tggacagtgt     2400
ctgtgaacga gggccgctgg gtacgggtt gctctgccgg aggctgccgc aacttcccag     2460
atactttctg gaccaaccct cagtaccgtc tgaagctcct ggaggaggac gatgaccctg     2520
atgactcgga ggtgatttgc agcttcctgg tggccctgat gcagaagaac cggcggaagg     2580
accggaagct agggccagt ctcttcacca ttggcttcgc catctacgag gttcccaaag     2640
agatgcacgg gaacaagcag cacctgcaga aggacttctt cctgtacaac gcctccaagg     2700
ccaggagcaa aacctacatc aacatgcggg aggtgtccca gcgcttccgc ctgcctccca     2760
gcgagtacgt catcgtgccc tccacctacg agccccacca ggaggggaa ttcatcctcc     2820 gggtcttctc tgaaaagagg aacctctctg aggaagttga aaataccatc tccgtggatc     2880
ggccagtgaa aaagaaaaaa accaagccca tcatcttcgt ttcggacaga gcaaacagca     2940
acaaggagct gggtgtggac caggagtcag aggagggcaa aggcaaaaca agccctgata     3000
```

```
agcaaaagca gtccccacag ccacagcctg gcagctctga tcaggaaagt gaggaacagc   3060
aacaattccg gaacattttc aagcagatag caggagatga catggagatc tgtgcagatg   3120
agctcaagaa ggtccttaac acagtcgtga acaaacacaa ggacctgaag acacacgggt   3180
tcacactgga gtcctgccgt agcatgattg cgctcatgga tacagatggc tctggaaagc   3240
tcaacctgca ggagttccac cacctctgga caagattaa ggcctggcag aaattttca    3300 aacactatga cacagaccag tccggcacca tcaacagcta cgagatgcga aatgcagtca   3360
acgacgcagg attccacctc aacaaccagc tctatgacat cattaccatg cggtacgcag   3420
acaaacacat gaacatcgac tttgacagtt tcatctgctg cttcgttagg ctggagggca   3480
tgttcagagc ttttcatgca tttgacaagg atggagatgg tatcatcaag ctcaacgttc   3540
tggagtggct gcagctcacc atgtatgcct gagcggccgc ggggatccag acatgataag   3600
atacattgat gagtttggac aaaccacaac tagaatgcag tgaaaaaaat gctttatttg   3660
taaaatttgt gatgctattg ctttatttgt aaccattata agctgcaata aacaagttaa   3720
caacaacaat tgcattcatt ttatgtttca ggttcagggg gaggtgtggg aggttttttc   3780
ggatcctcta gagtcgacca gagcatggct acgtagataa gtagcatggc gggttaatca   3840
ttaactacaa ggaacccta gtgatggagt tggccactcc ctctctgcgc gctcgctcgc    3900
tcactgaggc cgggcgacca aggtcgccc gacgcccggg ctttgcccgg gcggcctcag    3960
tgagcgagcg agcgcgcagc tgcattaatg aatcggccaa cgcgcgggga gaggcggttt   4020
gcgtattggg cgctcttccg cttcctcgct cactgactcg ctgcgctcgg tcgttcggct   4080
gcggcgagcg gtatcagctc actcaaaggc ggtaatacgg ttatccacag aatcagggga   4140
taacgcagga aagaacatgt gagcaaaagg ccagcaaaag gccaggaacc gtaaaaaggc   4200
cgcgttgctg gcgtttttcc ataggctccg ccccctgac gagcatcaca aaaatcgacg    4260
ctcaagtcag aggtggcgaa acccgacagg actataaaga taccaggcgt ttccccctgg   4320
aagctccctc gtgcgctctc ctgttccgac cctgccgctt accggatacc tgtccgcctt   4380
tctcccttcg ggaagcgtgg cgctttctca tagctcacgc tgtaggtatc tcagttcggt   4440
gtaggtcgtt cgctccaagc tgggctgtgt gcacgaaccc cccgttcagc ccgaccgctg   4500
cgccttatcc ggtaactatc gtcttgagtc aacccggta agacacgact tatcgccact    4560
ggcagcagcc actggtaaca ggattagcag agcgaggtat gtaggcggtg ctacagagtt   4620
cttgaagtgg tggcctaact acggctacac tagaaggaca gtatttggta tctgcgctct   4680
gctgaagcca gttaccttcg gaaaaagagt ggtagctct tgatccggca aacaaaccac    4740
cgctggtagc ggtggttttt tgtttgcaa gcagcagatt acgcgcagaa aaaaggatc    4800 tcaagaagat cctttgatct tttctacggg gtctgacgct cagtggaacg aaaactcacg   4860
ttaagggatt ttggtcatga gattatcaaa aaggatcttc acctagatcc ttttaaatta   4920
aaaatgaagt tttaaatcaa tctaaagtat atatgagtaa aatattccg gaattgccag    4980 ctggggcgcc ctctggtaag gttgggaagc cctgcaaagt aaactggatg ctttcttgc    5040 cgccaaggat ctgatggcgc aggggatcaa gatctgatca agagacagga tgaggatcgt   5100
ttcgcatgat tgaacaagat ggattgcacg caggttctcc ggccgcttgg gtggagaggc   5160
tattcggcta tgactgggca acagacaa tcggctgctc tgatgccgcc gtgttccggc     5220
tgtcagcgca gggcgcccg gttcttttg tcaagaccga cctgtccggt gccctgaatg     5280
aactgcagga cgaggcagcg cggctatcgt ggctggccac gacgggcgtt ccttgcgcag   5340
```

-continued

```
ctgtgctcga cgttgtcact gaagcgggaa gggactggct gctattgggc gaagtgccgg      5400
ggcaggatct cctgtcatcc caccttgctc ctgccgagaa agtatccatc atggctgatg      5460
caatgcggcg gctgcatacg cttgatccgg ctacctgccc attcgaccac caagcgaaac      5520
atcgcatcga gcgagcacgt actcggatgg aagccggtct tgtcgatcag gatgatctgg      5580
acgaagagca tcaggggctc gcgccagccg aactgttcgc caggctcaag gcgcgcatgc      5640
ccgacgcgca ggatctcgtc gtgacccatg gcgatgcctg cttgccgaat atcatggtgg      5700
aaaatggccg cttttctgga ttcatcgact gtggccggct gggtgtggcg gaccgctatc      5760
aggacatagc gttggctacc cgtgatattg ctgaagagct tggcggcgaa tgggctgacc      5820
gcttcctcgt gctttacggt atcgccgctc ccgattcgca gcgcatcgcc ttctatcgcc      5880
ttcttgacga gttcttctga accgtaata ttattgaagc atttatcagg gttattgtct      5940
catgagcgga tacatatttg aatgtattta gaaaaataaa caaatagggg ttccgcgcac      6000
atttccccga aaagtgccac ctgacgtcta agaaaccatt attatcatga cattaaccta      6060
taaaaatagg cgtatcacga ggcccttcg tctcgcgcgt ttcggtgatg acggtgaaaa      6120
cctctgacac atgcagctcc cggagacggt cacagcttgt ctgtaagcgg atgccgggag      6180
cagacaagcc cgtcagggcg cgtcagcggg tgttggcggg tgtcggggct ggcttaacta      6240
tgcggcatca gagcagattg tactgagagt gcaccatatg cggtgtgaaa taccgcacag      6300
atgcgtaagg agaaaatacc gcatcaggaa cttccaacat ccaataaatc atacaggcaa      6360
ggcaaagaat tagcaaaatt aagcaataaa gcctcagagc ataaagctaa atcggttgta      6420
ccaaaaacat tatgaccctg taatactttt gcgggagaag cctttatttc aacgcaagga      6480
taaaattttt tagaaccctc atatatttta aatgcaatgc ctgagtaatg tgtaggtaaa      6540
gattcaaacg ggtgagaaag gccggagaca gtcaaatcac catcaatatg atattcaacc      6600
gttctagctg ataaattcat gccggagagg gtagctattt ttgagaggtc tctacaaagg      6660
ctatcaggtc attgcctgag agtctggagc aaacaagaga atcgatgaac ggtaatcgta      6720
aaactagcat gtcaatcata tgtaccccgg ttgataatca gaaaagcccc aaaaacagga      6780
agattgtata agcaaatatt taaattgtaa acgttaatat tttgttaaaa ttcgcgttaa      6840
atttttgtta aatcagctca ttttttaacc aataggccga atcggcaaa atcccttata      6900 aatcaaaaga atagaccgag ataggggttga gtgttgttcc agtttggaac aagagtccac      6960
tattaaagaa cgtggactcc aacgtcaaag ggcgaaaaac cgtctatcag ggcgatggcc      7020
cactacgtga accatcaccc taatcaagtt ttttggggtc gaggtgccgt aaatcactaa      7080
atcggaaccc taagggagc ccccgattta gagcttgacg gggaaagccg gcgaacgtgg      7140
cgagaaagga agggaagaaa gcgaaaggag cgggcgctag ggcgctggca agtgtagcgg      7200
tcacgctgcg cgtaaccacc acacccgccg cgcttaatgc gccgctacag ggcgcgtact      7260
atggttgctt tgacgagcac gtataacgtg ctttcctcgt tagaatcaga gcgggagcta      7320
aacaggaggc cgattaaagg gattttagac aggaacggta cgccagaatc ctgagaagtg      7380
tttttataat cagtgaggcc accgagtaaa agagtctgtc catcacgcaa attaaccgtt      7440
gtcgcaatac ttctttgatt agtaataaca tcacttgcct gagtagaaga actcaaacta      7500
tcggccttgc tggtaatatc cagaacaata ttaccgccag ccattgcaac ggaatcgcca      7560
ttcgccattc aggctgcgca actgttggga agggcgatcg gtgcgggcct cttcgctatt      7620
acgccagct                                                             7629
```

```
<210> SEQ ID NO 2
<211> LENGTH: 2466
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: CAPN3 polynucleotide

<400> SEQUENCE: 2
atgccgaccg tcattagcgc atctgtggct ccaaggacag cggctgagcc ccggtcccca      60
gggccagttc ctcacccggc ccagagcaag gccactgagg ctggggggtgg aaacccaagt    120 ggcatctatt cagccatcat cagccgcaat tttcctatta tcggagtgaa agagaagaca    180
ttcgagcaac ttcacaagaa atgtctagaa aagaaagttc tttatgtgga ccctgagttc    240
ccaccggatg agacctctct cttttatagc cagaagttcc ccatccagtt cgtctggaag    300
agacctccgg aaatttgcga gaatcccga tttatcattg atggagccaa cagaactgac    360
atctgtcaag gagagctagg ggactgctgg ttttctcgcag ccattgcctg cctgaccctg    420
aaccagcacc ttcttttccg agtcataccc catgatcaaa gtttcatcga aaactacgca    480
gggatcttcc acttccagtt ctggcgctat ggagagtggg tggacgtggt tatagatgac    540
tgcctgccaa cgtacaacaa tcaactggtt ttcaccaagt ccaaccaccg caatgagttc    600
tggagtgctc tgctggagaa ggcttatgct aagctccatg ttcctacga agctctgaaa    660 ggtgggaaca ccacagaggc catggaggac ttcacaggag gggtggcaga gttttttgag    720
atcagggatg ctcctagtga catgtacaag atcatgaaga agccatcga gagaggctcc    780 ctcatgggct gctccattga tgatggcacg aacatgacct atggaacctc tccttctggt    840
ctgaacatgg gggagttgat tgcacggatg gtaaggaata tggataactc actgctccag    900
gactcagacc tcgaccccag aggctcagat gaaagaccga cccggacaat cattccggtt    960
cagtatgaga caagaatggc ctgcgggctg gtcagaggtc acgcctactc tgtcacgggg   1020
ctggatgagg tcccgttcaa aggtgagaaa gtgaagctgg tgcggctgcg gaatccgtgg   1080
ggccaggtgg agtggaacgg ttcttggagt gatagatgga aggactggag cttttgtggac   1140 aaagatgaga aggcccgtct gcagcaccag gtcactgagg atggagagtt ctggatgtcc   1200
tatgaggatt tcatctacca tttcacaaag ttggagatct gcaacctcac ggccgatgct   1260
ctgcagtctg acaagcttca gacctggaca gtgtctgtga acgagggccg ctgggtacgg   1320
ggttgctctg ccggaggctg ccgcaacttc ccagatactt tctggaccaa ccctcagtac   1380
cgtctgaagc tcctggagga ggacgatgac cctgatgact cggaggtgat ttgcagcttc   1440
ctggtggccc tgatgcagaa gaaccggcgg aaggaccgga agctagggggc cagtctcttc   1500 accattggct tcgccatcta cgaggttccc aaagagatgc acgggaacaa gcagcacctg   1560
cagaaggact tcttcctgta caacgcctcc aaggccagga gcaaaaccta catcaacatg   1620
cgggaggtgt cccagcgctt ccgcctgcct cccagcgagt acgtcatcgt gcctccacc   1680 tacgagcccc accaggaggg ggaattcatc ctccgggtct tctctgaaaa gaggaacctc   1740
tctgaggaag ttgaaaatac catctccgtg atcggccag tgaaaaagaa aaaaaccaag   1800
cccatcatct tcgtttcgga cagagcaaac agcaacaagg agctgggtgt ggaccaggag   1860
tcagaggagg gcaaaggcaa aacaagcct gataagcaaa agcagtcccc acagccacag   1920
cctggcagct ctgatcagga aagtgaggaa cagcaacaat tccggaacat tttcaagcag   1980
atagcaggag atgacatgga gatctgtgca gatgagctca gaaggtcct taacacagtc   2040
```

```
gtgaacaaac acaaggacct gaagacacac gggttcacac tggagtcctg ccgtagcatg    2100
attgcgctca tggatacaga tggctctgga aagctcaacc tgcaggagtt ccaccacctc    2160
tggaacaaga ttaaggcctg gcagaaaatt ttcaaacact atgacacaga ccagtccggc    2220
accatcaaca gctacgagat gcgaaatgca gtcaacgacg caggattcca cctcaacaac    2280
cagctctatg acatcattac catgcggtac gcagacaaac acatgaacat cgactttgac    2340
agtttcatct gctgcttcgt taggctggag ggcatgttca gagcttttca tgcatttgac    2400
aaggatggag atggtatcat caagctcaac gttctggagt ggctgcagct caccatgtat    2460
gcctga                                                                2466

<210> SEQ ID NO 3
<211> LENGTH: 720
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: tMCK promoter

<400> SEQUENCE: 3
ccactacggg tctaggctgc ccatgtaagg aggcaaggcc tggggacacc cgagatgcct      60
ggttataatt aaccccaaca cctgctgccc ccccccccc aacacctgct gcctgagcct     120
gagcggttac cccaccccgg tgcctgggtc ttaggctctg tacaccatgg aggagaagct    180
cgctctaaaa ataaccctgt ccctggtgga tccactacgg gtctaggctg ccatgtaag    240 gaggcaaggc ctggggacac ccgagatgcc tggttataat taaccccaac acctgctgcc    300 ccccccccc caacacctgc tgcctgagcc tgagcggtta ccccaccccg gtgcctgggt    360
cttaggctct gtacaccatg gaggagaagc tcgctctaaa ataaccctg tcctggtgg     420 atccactacg ggtctaggct gcccatgtaa ggaggcaagg cctggggaca cccgagatgc    480
ctggttataa ttaaccccaa cacctgctgc ccccccccc caacacctg ctgcctgagc     540 ctgagcggtt accccacccc ggtgcctggg tcttaggctc tgtacaccat ggaggagaag    600
ctcgctctaa aataaccct gtccctggtg gatcctccct ggggacagcc cctcctggct    660
agtcacaccc tgtaggctcc tctatataac caggggcac aggggctgcc cccgggtcac     720

<210> SEQ ID NO 4
<211> LENGTH: 22
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: MCK forward primer

<400> SEQUENCE: 4
cccgagatgc ctggttataa tt                                               22

<210> SEQ ID NO 5
<211> LENGTH: 19
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: MCK reverse primer
```

<400> SEQUENCE: 5
gctcaggcag caggtgttg                                                19

<210> SEQ ID NO 6
<211> LENGTH: 22
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: MCK probe

<400> SEQUENCE: 6
ccagacatgt ggctgctccc cc                                            22

<210> SEQ ID NO 7
<211> LENGTH: 821
<212> TYPE: PRT
<213> ORGANISM: Homo Sapiens

<400> SEQUENCE: 7

```
Met Pro Thr Val Ile Ser Ala Ser Val Ala Pro Arg Thr Ala Ala Glu
1               5                   10                  15

Pro Arg Ser Pro Gly Pro Val Pro His Pro Ala Gln Ser Lys Ala Thr
            20                  25                  30

Glu Ala Gly Gly Gly Asn Pro Ser Gly Ile Tyr Ser Ala Ile Ile Ser
        35                  40                  45

Arg Asn Phe Pro Ile Ile Gly Val Lys Glu Lys Thr Phe Glu Gln Leu
50                  55                  60

His Lys Lys Cys Leu Glu Lys Val Leu Tyr Val Asp Pro Glu Phe
65                  70                  75                  80

Pro Pro Asp Glu Thr Ser Leu Phe Tyr Ser Gln Lys Phe Pro Ile Gln
                85                  90                  95

Phe Val Trp Lys Arg Pro Pro Glu Ile Cys Glu Asn Pro Arg Phe Ile
            100                 105                 110

Ile Asp Gly Ala Asn Arg Thr Asp Ile Cys Gln Gly Glu Leu Gly Asp
        115                 120                 125

Cys Trp Phe Leu Ala Ala Ile Ala Cys Leu Thr Leu Asn Gln His Leu
130                 135                 140

Leu Phe Arg Val Ile Pro His Asp Gln Ser Phe Ile Glu Asn Tyr Ala
145                 150                 155                 160

Gly Ile Phe His Phe Gln Phe Trp Arg Tyr Gly Glu Trp Val Asp Val
                165                 170                 175

Val Ile Asp Asp Cys Leu Pro Thr Tyr Asn Asn Gln Leu Val Phe Thr
            180                 185                 190

Lys Ser Asn His Arg Asn Glu Phe Trp Ser Ala Leu Leu Glu Lys Ala
        195                 200                 205

Tyr Ala Lys Leu His Gly Ser Tyr Glu Ala Leu Lys Gly Gly Asn Thr
    210                 215                 220

Thr Glu Ala Met Glu Asp Phe Thr Gly Gly Val Ala Glu Phe Phe Glu
225                 230                 235                 240

Ile Arg Asp Ala Pro Ser Asp Met Tyr Lys Ile Met Lys Lys Ala Ile
                245                 250                 255

Glu Arg Gly Ser Leu Met Gly Cys Ser Ile Asp Asp Gly Thr Asn Met
            260                 265                 270
```

```
Thr Tyr Gly Thr Ser Pro Ser Gly Leu Asn Met Gly Glu Leu Ile Ala
            275                 280                 285

Arg Met Val Arg Asn Met Asp Asn Ser Leu Leu Gln Asp Ser Asp Leu
        290                 295                 300

Asp Pro Arg Gly Ser Asp Glu Arg Pro Thr Arg Thr Ile Ile Pro Val
305                 310                 315                 320

Gln Tyr Glu Thr Arg Met Ala Cys Gly Leu Val Arg Gly His Ala Tyr
                    325                 330                 335

Ser Val Thr Gly Leu Asp Glu Val Pro Phe Lys Gly Glu Lys Val Lys
                340                 345                 350

Leu Val Arg Leu Arg Asn Pro Trp Gly Gln Val Glu Trp Asn Gly Ser
            355                 360                 365

Trp Ser Asp Arg Trp Lys Asp Trp Ser Phe Val Asp Lys Asp Glu Lys
        370                 375                 380

Ala Arg Leu Gln His Gln Val Thr Glu Asp Gly Glu Phe Trp Met Ser
385                 390                 395                 400

Tyr Glu Asp Phe Ile Tyr His Phe Thr Lys Leu Glu Ile Cys Asn Leu
                    405                 410                 415

Thr Ala Asp Ala Leu Gln Ser Asp Lys Leu Gln Thr Trp Thr Val Ser
                420                 425                 430

Val Asn Glu Gly Arg Trp Val Arg Gly Cys Ser Ala Gly Gly Cys Arg
            435                 440                 445

Asn Phe Pro Asp Thr Phe Trp Thr Asn Pro Gln Tyr Arg Leu Lys Leu
        450                 455                 460

Leu Glu Glu Asp Asp Pro Asp Asp Ser Glu Val Ile Cys Ser Phe
465                 470                 475                 480

Leu Val Ala Leu Met Gln Lys Asn Arg Arg Lys Asp Arg Lys Leu Gly
                485                 490                 495

Ala Ser Leu Phe Thr Ile Gly Phe Ala Ile Tyr Glu Val Pro Lys Glu
                    500                 505                 510

Met His Gly Asn Lys Gln His Leu Gln Lys Asp Phe Phe Leu Tyr Asn
                515                 520                 525

Ala Ser Lys Ala Arg Ser Lys Thr Tyr Ile Asn Met Arg Glu Val Ser
            530                 535                 540

Gln Arg Phe Arg Leu Pro Pro Ser Glu Tyr Val Ile Val Pro Ser Thr
545                 550                 555                 560

Tyr Glu Pro His Gln Glu Gly Glu Phe Ile Leu Arg Val Phe Ser Glu
                    565                 570                 575

Lys Arg Asn Leu Ser Glu Glu Val Glu Asn Thr Ile Ser Val Asp Arg
                580                 585                 590

Pro Val Lys Lys Lys Thr Lys Pro Ile Ile Phe Val Ser Asp Arg
            595                 600                 605

Ala Asn Ser Asn Lys Glu Leu Gly Val Asp Gln Gly Ser Glu Glu Gly
        610                 615                 620

Lys Gly Lys Thr Ser Pro Asp Lys Gln Lys Gln Ser Pro Gln Pro Gln
625                 630                 635                 640

Pro Gly Ser Ser Asp Gln Glu Ser Glu Glu Gln Gln Phe Arg Asn
                    645                 650                 655

Ile Phe Lys Gln Ile Ala Gly Asp Asp Met Glu Ile Cys Ala Asp Glu
                660                 665                 670

Leu Lys Lys Val Leu Asn Thr Val Val Asn Lys His Lys Asp Leu Lys
            675                 680                 685

Thr His Gly Phe Thr Leu Glu Ser Cys Arg Ser Met Ile Ala Leu Met
```

```
                690                  695                   700
Asp Thr Asp Gly Ser Gly Lys Leu Asn Leu Gln Glu Phe His His Leu
705                 710                 715                 720

Trp Asn Lys Ile Lys Ala Trp Gln Lys Ile Phe Lys His Tyr Asp Thr
                725                 730                 735

Asp Gln Ser Gly Thr Ile Asn Ser Tyr Glu Met Arg Asn Ala Val Asn
                740                 745                 750

Asp Ala Gly Phe His Leu Asn Asn Gln Leu Tyr Asp Ile Ile Thr Met
                755                 760                 765

Arg Tyr Ala Asp Lys His Met Asn Ile Asp Phe Asp Ser Phe Ile Cys
                770                 775                 780

Cys Phe Val Arg Leu Glu Gly Met Phe Arg Ala Phe His Ala Phe Asp
785                 790                 795                 800

Lys Asp Gly Asp Gly Ile Ile Lys Leu Asn Val Leu Glu Trp Leu Gln
                805                 810                 815

Leu Thr Met Tyr Ala
                820

<210> SEQ ID NO 8
<211> LENGTH: 19
<212> TYPE: DNA
<213> ORGANISM: Artificial Sequence
<220> FEATURE:
<223> OTHER INFORMATION: Synthetic Primer

<400> SEQUENCE: 8
cggagagcaa ctgcataag                                              19

<210> SEQ ID NO 9
<211> LENGTH: 20
<212> TYPE: DNA
<213> ORGANISM: Artificial Sequence
<220> FEATURE:
<223> OTHER INFORMATION: Synthetic Primer

<400> SEQUENCE: 9
ggctgatgat ggctgaatag                                             20
```